(12) United States Patent
Husain

(10) Patent No.: US 10,898,592 B2
(45) Date of Patent: Jan. 26, 2021

(54) COMPOSITIONS AND METHODS FOR REDUCING THE RISK OF POST-IMAGING PANCREATITIS

(71) Applicant: University Of Pittsburgh—Of The Commonwealth System Of Higher Education, Pittsburgh, PA (US)

(72) Inventor: Sohail Husain, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 191 days.

(21) Appl. No.: 15/820,600

(22) Filed: Nov. 22, 2017

(65) Prior Publication Data

US 2018/0110885 A1 Apr. 26, 2018

Related U.S. Application Data

(63) Continuation of application No. PCT/US2016/034841, filed on May 27, 2016.

(60) Provisional application No. 62/167,143, filed on May 27, 2015.

(51) Int. Cl.
| | |
|---|---|
| A61K 49/04 | (2006.01) |
| A61P 1/18 | (2006.01) |
| A61K 38/13 | (2006.01) |
| A61K 31/436 | (2006.01) |
| A61K 45/06 | (2006.01) |
| A61K 31/16 | (2006.01) |
| A61K 31/19 | (2006.01) |
| G01N 33/50 | (2006.01) |

(52) U.S. Cl.
CPC .......... *A61K 49/0438* (2013.01); *A61K 31/16* (2013.01); *A61K 31/19* (2013.01); *A61K 31/436* (2013.01); *A61K 38/13* (2013.01); *A61K 45/06* (2013.01); *A61K 49/0452* (2013.01); *A61P 1/18* (2018.01); *G01N 33/507* (2013.01); *G01N 2800/067* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,060,733 B2 | 6/2006 | Pandol et al. | |
| 7,160,535 B2 | 1/2007 | Ranganathan et al. | |
| 7,833,279 B2 | 11/2010 | Knudson et al. | |
| 7,947,285 B2 | 5/2011 | Fein et al. | |
| 8,192,721 B2 | 6/2012 | Rowe | |
| 8,318,657 B2 | 11/2012 | Saccone et al. | |
| 8,560,053 B2 | 10/2013 | Pasricha | |
| 2003/0133906 A1 | 7/2003 | Deviere et al. | |
| 2009/0042969 A1 | 2/2009 | Lerch et al. | |
| 2012/0171168 A1 | 7/2012 | Song et al. | |
| 2013/0123934 A1 | 5/2013 | Azar | |

FOREIGN PATENT DOCUMENTS

| | | |
|---|---|---|
| CA | 2 603 084 A1 | 10/2006 |
| CN | 101297975 A | 11/2008 |
| CN | 101627987 A | 1/2010 |
| CN | 102144978 A | 8/2011 |
| CN | 103432099 A | 12/2013 |
| EP | 2 574 333 A1 | 4/2013 |
| WO | WO 1996/034645 A1 | 11/1996 |
| WO | WO 02/078627 A2 | 10/2002 |
| WO | WO 2005/004857 A1 | 1/2005 |
| WO | WO 2006/110802 A1 | 10/2006 |
| WO | WO 2008/021550 A2 | 2/2008 |
| WO | WO 2008/057534 A2 | 5/2008 |
| WO | WO 2009/049022 A1 | 4/2009 |
| WO | WO 2009/088860 A2 | 7/2009 |
| WO | WO 2009/137827 A2 | 11/2009 |

OTHER PUBLICATIONS

Carmona-Sánchez et al. Potential harmful effect of iodinated intravenous contrast medium on the clinical course of mild acute pancreatitis. 2000 Arch. Surg. 135: 1280-1284. (Year: 2000).*
Goebel et al., "Frequency of pancreatitis after endoscopic retrograde cholangiopancreatography with iopromid or iotrolan: a randomized trial," European Radiology 10:677-680 (2000).
Supplementary European Search Report dated Dec. 12, 2018 in EP Application No. 16800839.
Abu Jawdeh et al., "Incidence and Risk Factors of Contrast-Induced Nephropathy in Renal Allograft Recipients," [abstract]. Am J Transplant. 2015; 15(suppl 3). https://atcmeetingabstracts.com/abstract/incidence-and-risk-factors-of-contrast-induced-nephropathy-in-renal-allograft-recipients/. Accessed Oct. 18, 2018.
ACT Investigators, "Acetylcysteine for Prevention of Renal Outcomes in Patients Undergoing Coronary and Peripheral Vascular Angiography: Main Results from the Randomized Acetylcysteine for Contrast-Induced Nephropathy Trial (ACT)," Circulation 124:1250-1259 (2011).
Andreucci et al., "Side Effects of Radiographic Contrast Media: Pathogenesis, Risk Factors, and Prevention," BioMed Research International, vol. 2014 (2014), Article ID 741018, 20 pages.
Andreucci et al., "Differential Activation of Signaling Pathways by Low-Osmolar and Iso-Osmolar Radiocontrast Agents in Human Renal Tubular Cells," J Cell Biochem 115:281-289 (2014).

(Continued)

*Primary Examiner* — Jennifer Lamberski
(74) *Attorney, Agent, or Firm* — Baker Botts L.L.P.

(57) ABSTRACT

The present invention relates to compositions and methods for reducing the risk of post-imaging pancreatitis for procedures that employ a radiocontrast medium, particularly procedures that selectively image the pancreas, gallbladder and/or biliary tree. In non-limiting embodiments, the invention provides for a radiocontrast medium comprising: (i) a radiocontrast agent; (ii) a calcineurin inhibitor; and (iii) an antioxidant, and its use in performing imaging of the pancreas and related structures with decreased risk of subsequent pancreatitis relative to conventional radiocontrast agents that lack elements (ii) and (iii).

Figure 1A:
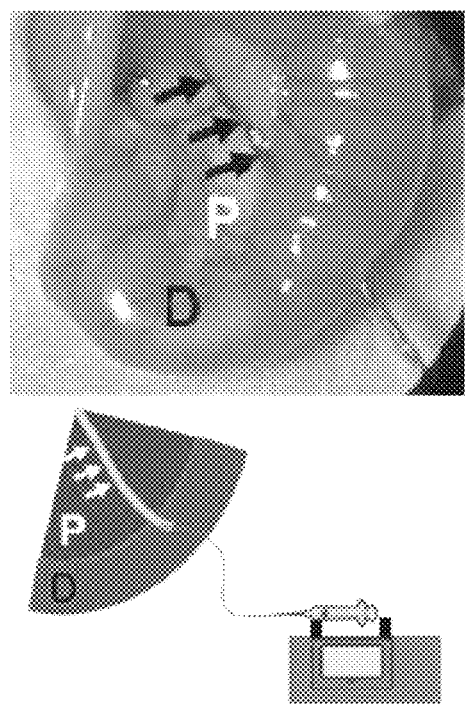

15 Claims, 66 Drawing Sheets
Specification includes a Sequence Listing.

(56) References Cited

OTHER PUBLICATIONS

Andriulli et al., "Incidence Rates of Post-ERCP Complications: A Systematic Survey of Prospective Studies," Am J Gastroenterol 102:1781-1788 (2007).
Asher et al., "New usage for an old drug: Acetylcysteine for contrast-induced nephropathy," Harefuah, 144(9):642-646 (2005) (English abstract only, article in Hebrew).
Bang et al., "Pharmacological approach to acute pancreatitis," World J. Gastroenterol 14(19):2968-2976 (2008).
Baranska-Kosakowska et al., "Role of N-Acetylcysteine on Renal Function in Patients after Orthotopic Heart Transplantation Undergoing Coronary Angiography," Transplant Proc. 39:2853-2855 (2007).
Brown et al., "Control of IκB-α Proteolysis by Site-Specific, Signal-Induced Phosphorylation," Science 267:1485-1488 (1995).
Bueno et al., "Defective T cell development and function in calcineurin Aβ-deficient mice," PNAS 99(14):9398-9403 (2002).
Chutkan et al., "ERCP core curriculum," Gastrointest Endosc 63(3):361-376 (2006).
Darrouzet et al., "The sodium/iodide symporter: State of the art of its molecular characterization," Biochimica et Biophys Acta 1838:244-253 (2014).
De Las Heras-Castano et al., "Pancreatic Fibrosis in Rats and its Response to Antioxidant Treatment," JOP. J Pancreas(Online) 6(4):316-324 (2005).
Demols et al., "N-Acetylcysteine Decreases Severity of Acute Pancreatitis in Mice," Pancreas 20(2):161-169 (2000).
Du et al., "N-Acetylcysteine Improves Pancreatic Microcirculation and Alleviates the Severity of Acute Necrotizing Pancreatitis," Gut Liver 7(3):357-362 (2013).
Durgampudi et al., "Acute Lipotoxicity Regulates Severity of Biliary Acute Pancreatitis without Affecting Its Initiation," Am J Pathol. 184(6):1773-1784 (2014).
Echigo et al., "Effects of Cyclosporine and Tacrolimus (FK 506) on acute pancreatitis in mice," Arch Surg. 130:64-68 (1995).
Elmunzer et al., "A Randomized Trial of Rectal Indomethacin to Prevent Post-ERCP Pancreatitis," N Engl. J Med 366(15):1414-1422 (2012).
Fazel et al., "Does a pancreatic duct stent prevent post-ERCP pancreatitis? A prospective randomized study," Gastrointest Endosc 57:291-294 (2003).
Frank et al., "Post-ERCP pancreatitis and its prevention," Nat Clin Practice Gastroenterol Hepatol 3(12):680-688 (2006).
Freeman et al., "Take 2 Indomethacin (Suppositories) and Call Me in the Morning? The Role of Nonsteroidal Anti-inflammatory Drugs in Protection Against Post-Endoscopic Retrograde Cholangiopancreatography Pancreatitis," Gastroenterology 150:805-808 (2016).
George et al., "Role of Osmolality of Contrast Media in the Development of Post-ERCP Pancreatitis: A Metanalysis," Dig Dis Sci 49(3):503-508 (2004).
Giurisato et al., "The KSR2-calcineurin complex regulates STIM1-ORAI1 dynamics and store-operated calcium entry (SOCE)," Mol. Biol. Cell 25:1769-1781 (2014).
Gukovskaya et al., "Ethanol differentially regulates NF-κB activation in pancreatic acinar cells through calcium and protein kinase C pathways," Am J Physiol Gastrointest Liver Physiol 286:G204-G213 (2004).
Haciahmetoglu et al., "The effects of contrast agent and intraductal pressure changes on the development of pancreatitis in an ERCP model in rats," Langenbecks Arch Surg 393:367-372 (2008).
Heit et al., "Calcineurin/NFAT signalling regulates pancreatic β-cell growth and function," Nature 443:345-349 (2006).
Hogan et al., "Calcineurin," Current Biology 15(12):R442-R443 (2005).
Huang et al., "Activation of Nuclear Factor-κB in Acinar Cells Increases the Severity of Pancreatitis in Mice," Gastroenterology 144:202-210 (2013).
Husain et al., "Caerulein-induced intracellular pancreatic zymogen activation is dependent on calcineurin," Am J Physiol. Gastrointest Liver Physiol 292:G1594-G1599 (2007).
Husain et al., "Ryanodine receptors contribute to bile acid-induced pathological calcium signaling and pancreatitis in mice," Am J Physiol Gastrointest Liver Physiol. 302:G1423-G1433 (2012).
Husain et al., "The ryanodine receptor mediates early zymogen activation in pancreatitis," PNAS USA 102(40):14386-14391 (2005).
Im et al., "Diabetic Ketoacidosis Associated with Acute Pancreatitis in a Heart Transplant Recipient Treated with Tacrolimus," Exp. Clin. Transplant 1:72-74 (2013).
International Search Report dated Aug. 24, 2016 in International Application No. PCT/US2016/034841.
Jin et al., "Exposure to Radiocontrast Agents Induces Pancreatic Inflammation by Activation of Nuclear Factor-κB, Calcium Signaling, and Calcineurin," Gastroenterology 149:753-764 (2015).
Kapturczak et al., "Pharmacology of Calcineurin Antagonists," Transplantation Proceedings 36(Suppl. 2S):25S-32S (2004).
Kruger et al., "The Role of Intracellular Calcium Signaling in Premature Protease Activation and the Onset of Pancreatitis," Am J Pathol 157(1):43-50 (2000).
Lawrence, "The Nuclear Factor NF-κB Pathway in Inflammation," Cold Spring Harb Perspect Biol 1:a001651 (2009).
Lee et al., "Cyclosporin A, but not FK506, Induces Osmotic Lysis of Pancreas Zymogen Granules, Intra-Acinar Enzyme Release, and Lysosome Instability by Activating K+ Channel," Pancreas 41(4):596-604 (2012).
Li et al., "Interaction of calcineurin with substrates and targeting proteins," Trends Cell Biol. 21(2):91-103 (2011).
Liu et al., "Anti-inflammatory Effects of Tacrolimus in a Rat Model of Acute Pancreatitis," Med. Chem. 6:37-43 (2010).
Madisen et al., "A robust and high-throughput Cre reporting and characterization system for the whole mouse brain," Nat Neurosci 13(1):133-140 (2010).
Maranki et al., "Prevention of Post-ERCP Pancreatitis," Curr Gastroenterol Rep 15:352 (2013).
Mayer et al., "Single Doses of FK506 and OKT3 Reduce Severity in Early Experimental Acute Pancreatitis," Eur. J. Surgery 166:734-741 (2000).
Mazen et al., "Trends in the Utilization of Endoscopic Retrograde Cholangiopancreatography (ERCP) in the United States," Am J Gastroenterol 102:966-975 (2007).
McCullough et al., "Minimizing the Renal Toxicity of Iodinated Contrast," Circulation 124:1210-1211 (2011).
Michael et al., "Molecular Mechanisms of Renal Cellular Nephrotoxicity due to Radiocontrast Media," Biomed Res Int 2014:249810, 10 pages (2014).
Mishkin et al. "ASGE Technology Status Evaluation Report: radiographic contrast media used in ERCP," Gastrointest Endosc 62(4):480-484 (2005).
Muallem et al., "Role of Na+/Ca2+ Exchange and the Plasma Membrane Ca2+ Pump in Hormone-Mediated Ca2+ Efflux from Pancreatic Acini," J Membr Biol. 102:153-162 (1988).
Muili et al., "Bile Acids Induce Pancreatic Acinar Cell Injury and Pancreatitis by Activating Calcineurin," J Biol Chem. 288(1):570-580 (2013).
Muili et al., "Calcineurin," The Pancreapedia: Exocrine Pancreas Knowledge Base, 10 pages (2011).
Muili et al., "Pancreatic Acinar Cell Nuclear Factor κB Activation because of Bile Acid Exposure is Dependent on Calcineurin," J Biol. Chem. 288(29):21065-21073 (2013).
Muili et al., "Pharmacological and genetic inhibition of calcineurin protects against carbachol-induced pathological zymogen activation and acinar cell injury," Am J Physiol Gastrointest Liver Physiol 302:G898-G905 (2012).
Nagashio et al., "Action of Antiproteases on Fibrosis in Experimental Chronic Pancreatitis," JOP. J. Pancreas (Online), 8(4 Suppl.):495-500 (2007).
Navina et al., "Lipotoxicity causes Multisystem Organ Failure and Exacerbates Acute Pancreatitis in Obesity," Sci Transl Med 3:107ra110 (2011).
Neuhofer et al., "Deletion of IκBα Activates RelA to Reduce Acute Pancreatitis in Mice Through Up-regulation of Spi2A," Gastroenterology 144:192-201 (2013).

(56) References Cited

OTHER PUBLICATIONS

Nieto et al., "Acute pancreatitis during immunosuppression with tacrolimus following an allogeneic umbilical cord blood transplantation," Bone Marrow Transpl. 26:109-111 (2000).
Noble et al., "A pH-sensitive, neurogenic pathway mediates disease severity in a model of post-ERCP pancreatitis," Gut 57:1566-1571 (2008).
Orabi et al., "Dynamic Imaging of Pancreatic Nuclear Factor κB (NF-κB) Activation in Live Mice Using Adeno-associated Virus (AAV) Infusion and Bioluminescence," the Journal of Biological Chemistry 290(18):11309-11320 (2015).
Pandol, "The Exocrine Pancreas," in Colloquium Series on Integrated Systems Physiology: From Molecule to Function to Disease. San Rafael, CA: Morgan & Claypool Life Sciences, 2011.
Petersen et al., "Ca2+ signalling and pancreatitis: effects of alcohol, bile and coffee," Trends Pharmacol Sci 27(2):113-120 (2006).
Pfau et al., "Comparison of the Effect of Non-Ionic and Ionic Contrast Agents on Pancreatic Histology in a Canine Model," JOP. J Pancreas 7(1):27-33 (2006).
Ramudo et al., "N-acetylcysteine in acute pancreatitis," World J. Gastrointest Pharmacol Ther 1(1):21-26 (2010).
Raraty et al., "Calcium-dependent enzyme activation and vacuole formation in the apical granular region of pancreatic acinar cells," PNAS USA 97(24):13126-13131 (2000).
Rehman et al., "N-Acetylcysteine Effect on Serum Creatinine and Cystatin C Levels in CKD Patients," Clin. J. Am. Soc. Nephrol. 3:1610-1614 (2008).
Ruben et al., "Refinement of Canine Pancreatitis Model: Inducing Pancreatitis by Using Endoscopic Retrograde Cholangiopancreatography," Comp Med 59(1):78-82 (2009).
Sah et al., "New insights into the pathogenesis of pancreatitis," Curr Opin Gastroenterol 29:523-530 (2013).
Saluja et al., "Secretagogue-induced digestive enzyme activation and cell injury in rat pancreatic acini," Am J Physiol 276:G835-G842 (1999).
Sendeski, "Pathophysiology of renal tissue damage by iodinated contrast media," Clin Exp Pharmacol Physiol 38:292-299 (2011).
Shah et al., "Protease Activation during in vivo Pancreatitis is Dependent on Calcineurin Activation," Am J. Physiol. Gastrointest Liver Physiol 297:G967-G973 (2009).
Smithline et al., "Effect of prophylactic main pancreatic duct stenting on the incidence of biliary endoscopic sphincterotomy-induced pancreatitis in high-risk patients," Gastrointest Endosc 39:652-657 (1993).
Sofuni et al., "Prophylaxis of Post-Endoscopic Retrograde Cholangiopancreatography Pancreatitis by an Endoscopic Pancreatic Spontaneous Dislodgement Stent," Clin Gastroenterol Hepatol 5:1339-1346 (2007).
Swift et al., "Structure of the Two Related Elastase Genes Expressed in the Rat Pancreas," J Biol. Chem 259(22):14271-14278 (1984).
Talukdar et al., "Pancreatic stellate cells: New target in the treatment of chronic pancreatitis," J. Gastroenterol. Hepatol. 23:34-41 (2008).
Tarnasky et al., "Pancreatic Stenting Prevents Pancreatitis after Biliary Sphincterotomy in Patients with Sphincter of Oddi Dysfunction," Gastroenterology 115:1518-1524 (1998).
Timmerman et al., "Rapid shuttling of NF-AT in discrimination of Ca2+ signals and immunosuppression," Nature 383:837-840 (1996).
Vaquero et al., "Myofibroblast proliferation, fibrosis, and defective pancreatic repair induced by cyclosporin in rats," Gut 45:269-277 (1999).
Virlos et al., "Intravenous n-acetylcysteine, ascorbic acid and selenium-based anti-oxidant therapy in severe acute pancreatitis," Scandanavia J. Gastroenterol. 38:1262-1267 (2003).
Voll et al., "NF-κB Activation by the Pre-T Cell Receptor Serves as a Selective Survival Signal in T Lymphocyte Development," Immunity 13:677-689 (2000).
Voronina et al., "Effects of Secretagogues and Bile Acids on Mitochondrial Membrane Potential of Pancreatic Acinar Cells: Comparison of Different Modes of Evaluating $\Delta\psi m$," J Biol. Chem. 279(26):27327-27338 (2004).
Wang et al., "Radiographic contrast media induced nephropathy: experimental observations and the protective effect of calcium channel blockers," Br J Radiol 74:1103-1108 (2001).
Wang et al., "Widespread and Stable Pancreatic Gene Transfer by Adeno-Associated Virus Vectors via Different Routes," Diabetes 55:875-884 (2006).
Williams, "Regulation of Acinar Cell Function in the Pancreas," Curr Opin Gastroenterol 26(5):478-483 (2010).
Xu et al., "The Role of Nuclear Factor-κB in Rats of Radiocontrast-Media-Induced Nephropathy," J Biochem Mol. Toxicol 22(6):416-421 (2008).
Yang et al., "Selective Inhibition of the Reverse Mode of Na(+)/Ca(2+) Exchanger Attenuates Contrast-Induced Cell Injury," Am J Nephrol 37:264-273 (2013).
Yang et al., "The physiological roles of primary phospholipase C," Adv Biol. Regul 53:232-241 (2013).
Zhang et al., "IL-6 trans-signaling promotes pancreatitis-associated lung injury and lethality," J Clin Invest 123(3):1019-1031 (2013).

\* cited by examiner

Figure 6A:
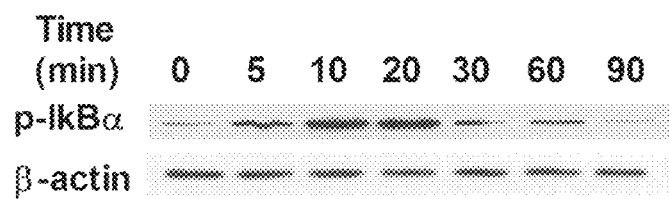
Figure 6A:
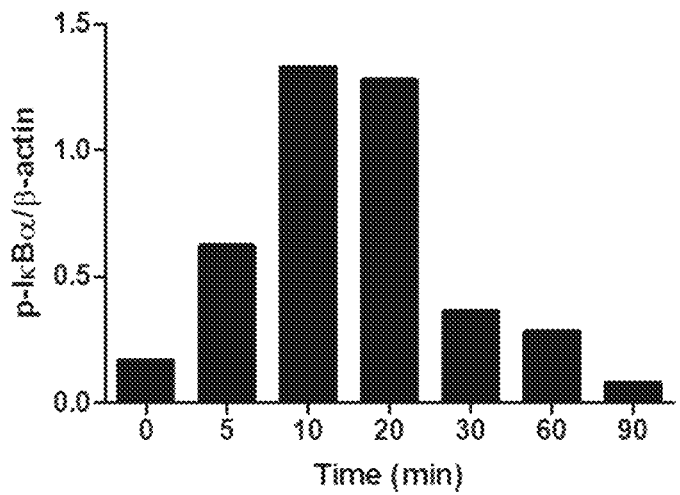
Figure 6A:
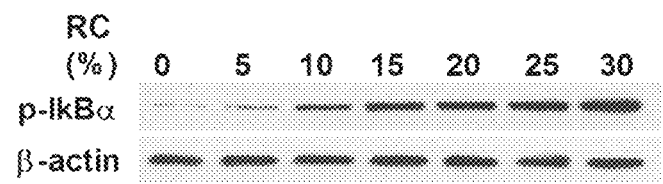
Figure 6A:
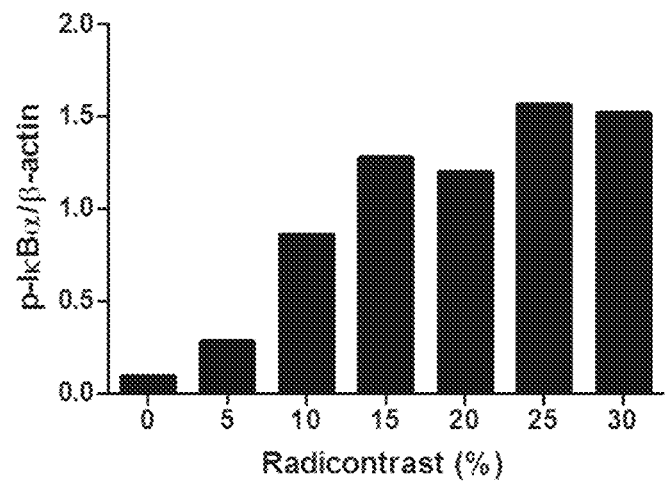

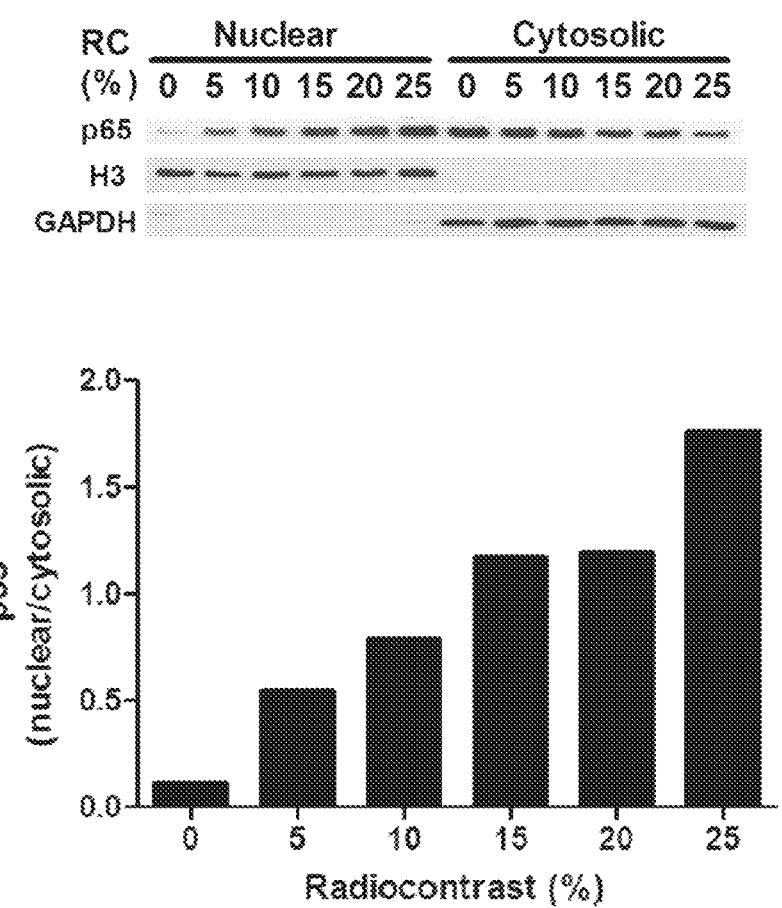
FIG. 6A-CONT.

AR42J

AAV6-Ela-iCre plasmid

COMPOSITIONS AND METHODS FOR REDUCING THE RISK OF POST-IMAGING PANCREATITIS

CROSS-REFERENCE TO RELATED APPLICATIONS

This application is a continuation of the International Application No. PCT/US2016/034841, filed May 27, 2016, which claims priority to U.S. Provisional Patent Application Ser. No. 62/167,143, filed May 27, 2015, both of which are incorporated by reference herein in their entireties.

GRANT INFORMATION

This invention was made with government support under grant numbers DK093491, DK083327 and DK103002 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 22, 2017, is named 072396_0697_SL.txt and is 2,342 bytes in size.

1. INTRODUCTION

The present invention relates to compositions, for use in imaging studies of the pancreas and related structures, which decrease the risk of post-imaging pancreatitis, and corresponding methods of use.

2. BACKGROUND OF THE INVENTION

Endoscopic retrograde cholangiopancreatography (ERCP) is a common gastrointestinal procedure in which an endoscope is inserted up to the duodenum and the ampulla of Vater is cannulated[1]. Radiocontrast (RC) is injected through a catheter in order to radiographically visualize the pancreaticobiliary tree. ERCPs are common procedures with an estimated annual incidence of 60 to 75 performed per 100,000 persons in the United States[2]. They are indispensable for the removal of impacted gall stones in the common bile duct (CBD) and various other therapeutic interventions. However, the most common iatrogenic complication of ERCP is acute pancreatitis, which is a painful, inflammatory disorder of the pancreas. The frequency of post-ERCP pancreatitis (PEP) ranges between 1% and 15% and has an overall average of 3.5%[3,4]. PEP has been attributed to a combination of hydrostatic pressure in the pancreatic duct and exposure of the pancreas to RC. In high risk situations, placement of a pancreatic duct stent or rectal administration of the anti-inflammatory drug indomethacin has been used[5-9]. However, the efficacy of widely accepted strategies to prevent PEP, such as pretreatment with rectal indomethacin[2] has been challenged[3,4]. The search for PEP prevention requires uncovering the fundamental mechanism by which RC induces pancreatic injury leading to pancreatitis, which has not hitherto been elucidated.

3. SUMMARY OF THE INVENTION

The present invention relates to compositions and methods for reducing the risk of post-imaging pancreatitis for procedures that employ a radiocontrast medium, particularly procedures that selectively image the pancreas, gallbladder and/or biliary tree.

In non-limiting embodiments, the invention provides for a radiocontrast medium comprising: (i) a radiocontrast agent; (ii) a calcineurin inhibitor; and (iii) an antioxidant. In related non-limiting embodiments, said radiocontrast medium may be used in performing imaging of the pancreas and related structures with decreased risk of subsequent pancreatitis relative to conventional radiocontrast agents that lack elements (ii) and (iii).

In particular non-limiting embodiments, the radiocontrast medium of the invention may be employed in Endoscopic Retrograde Cholangiopancreatography (ERCP), where it reduces the risk of post-ERCP pancreatitis (PEP).

In related non-limiting embodiments, the radiocontrast medium may be used in imaging of the pancreas and related structures to reduce the magnitude of any pancreatitis which may subsequently occur.

In related non-limiting embodiments, the radiocontrast medium may be introduced directly (e.g., into the biliopancreatic duct) or indirectly (e.g., via intravenous administration) into the biliary tree.

In further non-limiting embodiments, the invention provides for a high-throughput screen for in vitro assays of pancreatitis using a virally mediated reporter system for measuring inflammatory changes and/or injury in an acinar cell line, as well as an in vivo method of assaying pancreatic NF-kB in mice that receive a luciferase reporter through a viral vector.

In further non-limiting embodiments, the invention provides for modulators of pancreatic inflammation, in vitro assays of pancreatitis using a virally mediated reporter system for measuring inflammatory changes and/or injury in an acinar cell line, as well as an in vivo method of assaying pancreatic NFAT in mice that receive a luciferase reporter through a viral vector.

4. BRIEF DESCRIPTION OF DRAWINGS

FIG. 1A-1F. RC infusion causes pancreatitis in vivo and induces $Ca^{2+}$ signals in mouse pancreatic acinar cells. (A) Schema for RC infusion into the distal common bile duct (arrows) using a perfusion pump (P, pancreas; D, duodenum). (B) Representative HE sections of the pancreatic head from NS sham control and RC-infused (at 20 µl/min, 100 µl volume) mice. A combination of intra-ductal RC along with an increased rate and volume induced greater histological severity and higher serum amylase levels. (n=5 animals per condition). *, P<0.05 relative to NS sham. (C) Mouse pancreatic acinar cells are loaded onto a custom-made perifusion chamber and imaged using a confocal microscope. (D) Phase contrast image and pseudo-colored images of acini loaded with the $Ca^{2+}$ dye Fluo-4AM at baseline, during the initial rise in $Ca^{2+}$ fluorescence, and peak fluorescence during perfusion with RC. An individual acinar cell is outlined in the dashed white line, and the red arrows indicate the progression of the $Ca^{2+}$ signal from the apical to basal region of the cell. (E) Summation of whole cell tracings of $Ca^{2+}$ flux with increasing concentrations of RC. (F) Amplitude and area under the curve measurements of the $Ca^{2+}$ signal. Acinar cells were perfused with RC (25%) in the presence or absence of $Ca^{2+}$ containing media (n=20-30 cells per condition). *, P<0.05 compared to 17% RC.

FIG. 2A-2F. Histological subscore following infusion with iohexol (Omnipaque 300), and evidence that iopamidol (Isovue 300) also induces pancreatitis. (A) HE-stained sections of the pancreatic head were collected 24 hr after the surgical procedure. Histological severity of pancreatitis was graded by the presence of edema, inflammatory infiltrate, and necrosis. (n=5 animals per group). *, P<0.05 relative to NS sham. (B) Representative HE sections of the pancreatic head from NS sham, iopamidol, and iohexol-infused mice. (C, E) Histological severity, (D) serum amylase levels, and (F) serum IL-6 were measured 24 hr after the surgical procedure. (n=5 animals per group). *, P<0.05 relative to NS sham.

FIG. 3A-3E. RC induces $Ca^{2+}$ signals and calcineurin activation in human pancreatic acinar cells but fails to induce sizeable $Ca^{2+}$ signals in nonpancreatic cell lines. (A) Summation of whole cell tracings from human acinar cells loaded with Fluo-4AM and perifused with RC (10-50%). (B) Quantification of amplitude and area under the cure. (n=20-30 cells per condition). *, P<0.05 relative to 10% RC. (C) Human acinar cells were infected with Ad-NFAT-luciferase and stimulated with RC at increasing concentrations. RC (25%)-induced NFAT-luciferase activity was prevented by the intracellular $Ca^{2+}$ chelator BAPTA. (n=3). *, #, P<0.05, relative to the control or RC alone, respectively. Summation of whole cell tracings from (D) HEK293 or (E) COS7 cells loaded with Fluo-4AM and perifused with RC (25-75%). In these graphs, the terminal portion of the experiment is shown, in which carbachol (1 mM) is perifused to confirm the cells' ability to mobilize $Ca^{2+}$ (n=20-30 cells per condition).

FIG. 4A-4D. RC induces acinar cell calcineurin activation via $Ca^{2-}$ mobilization and IP3Rs. Mouse acinar cells were infected with Ad-NFAT-luciferase and stimulated with RC (A) for varying time periods (25% RC) or (B) with increasing concentrations for 5 hr. RC (9%)-induced NFAT-luciferase activity was prevented by (C) 30 min pre-treatment with the calcineurin inhibitors FK506 (24 μM) and cyclosporine (CsA; 16 μM) or (D) 30 min pre-treatment with the IP3R inhibitor 2-APB (100 μM) or the intracellular $Ca^{2+}$ chelator BAPTA-AM (64 μM). (n=3). *, #, P<0.05, relative to the control or RC alone, respectively.

Figure 5:
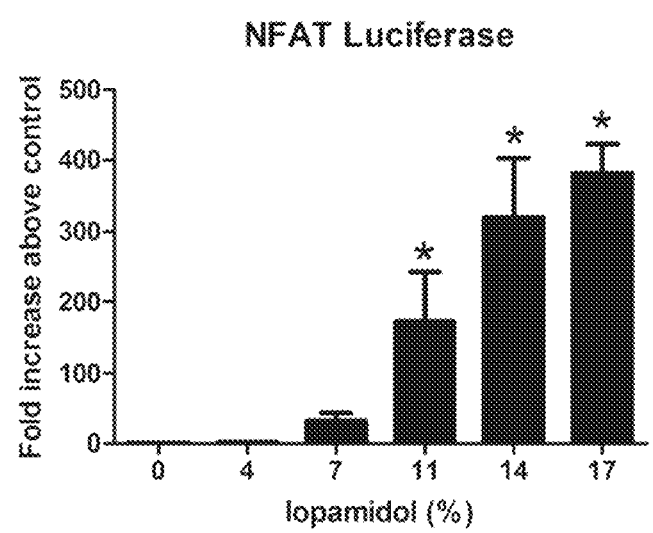

FIG. 5. The RC iopamidol (Isovue-300) induces calcineurin activation in AR42J cells. AR42J cells were infected with Ad-NFAT-luciferase and stimulated with varying concentrations of the RC iopamidol (n=3). *, P<0.05, relative to control.

FIG. 6A-6E. Calcineurin is both necessary and sufficient to induce acinar cell NF-κB (nuclear factor of kappa light chain enhancer B) activation due to RC. Western blots from primary mouse acinar cells stimulated with (A) 20% RC or varying concentrations of RC for 15 min or 30 min and probed for phosphorylated IκBα or p65. Densitometry shown below for each blot. (B) Acinar-differentiated AR42J cells were infected overnight with Ad-NF-κB-luciferase and then incubated for 6 hr with increasing concentrations of RC. AR42J cells were exposed to RC (25%) for varying times (solid lines) then washed off with buffer (dashed lines) and incubated for a total of 6 hr. (C) NF-κB-luciferase activity was prevented in AR42J cells by pre-treatment with the U73122 (5 μM), 2-APB (100 μM), BAPTA (64 μM), (D) FK506 (24 μM), and CsA (16 μM). (n=3). *, #, P<0.05, relative to the control or RC alone, respectively. (E) AR42J cells were infected with increasing titers of an adenovirus carrying a constitutively active form of the catalytic calcineurin A subunit (Ad-ΔCn) or infected with Ad-EGFP (negative control). NFAT- and NF-κB-luciferase activity were measured. Ad-EGFP at amounts greater than 4×10⁵ infectious units (IFU) failed to increase luciferase levels. Correlation between NFAT- and NF-κB-luciferase activity in AR42J cells ($R^2$=0.9185; P=0.0002). (n=3). *, P<0.05, relative to Ad-EGFP alone.

FIG. 7A-7H. RC induces $Ca^{2+}$ signals and calcineurin activation in AR4fu2J cells. (A) Summation of whole cell tracings from AR42J cells loaded with Fluo-4AM and perifused with RC (iohexol; 10-25%). (B, D) Quantification of amplitude and area under the curve. (C) RC (25%)-induced acinar cell $Ca^{2+}$ signals were prevented by the PLC inhibitor U73122 (5 μM) and the IP3R inhibitor 2-APB (100 μM). (n=20-30 cells per condition). *, #P<0.05 relative to 10% RC or RC alone, respectively. AR42J cells were infected with Ad-NFAT-luciferase and stimulated with RC at (E) increasing concentrations. RC (6%)-induced NFAT-luciferase activity was prevented by (F) pretreatment with the calcineurin inhibitor FK506 (24 μM), (G) CsA (16 μM), or (H) with U73122 (5 μM), 2-APB (100 μM) or the intracellular $Ca^{2+}$ chelator BAPTA (64 μM). (n=3). *, #, P<0.05, relative to the control or RC alone, respectively.

FIG. 8A-8F. The RC iopamidol (Isovue-300) also induces NF-κB activation in AR42J cells, and RC-induced NF-kB activation is not provoked by hyperosmolar conditions, oxidative stress, or the liberation of non-esterified fatty acids. (A) AR42J cells were infected with Ad-NF-κB-luciferase and stimulated with varying concentrations of iopamidol. (n=3). *, P<0.05, relative to control. (B) The calculated osmolality of iohexol (from the product insert) was verified by measuring osmolality with a freeze-thaw osmometer ($R^2$=0.9832). (C) AR42J cells were infected with Ad-NF-kB-luciferase and exposed to increasing osmolar concentrations of iohexol or mannitol (control). (D) Mice were infused with mannitol (672 mOsmol) at a concentration which mimics the osmolarity of full strength radiocontrast. Pancreatic tissue sections were graded 24 hr following infusion. NF-kB-luciferase was measured from AR42J cells stimulated with RC (16%) in the presence or absence of (E) the ROS scavenger N-acetylcysteine (NAC; 2-8 mM) or (F) the lipase inhibitor Orlistat (50-100 μM). (n=3). *, P<0.05, relative to the control.

FIG. 9A-9F. RC causes acinar cell necrosis through a $Ca^{2+}$/calcineurin-dependent pathway. (A) Acinar cells were treated with increasing concentrations of RC for 6 hr, and propidium iodide uptake was measured. RC (12%)-induced acinar cell injury (6 hr incubation) was prevented by (B) U73122 (5 μM), 2-APB (100 μM), BAPTA (64 μM), or (C) the NF-κB inhibitor IKK-2 (20 μM). (D) Inhibition of calcineurin (FK506; 24 μM, CsA; 16 μM) or (E) genetic deletion of the regulatory calcineurin Aβ subunit (CnAβ). (F) ATP levels were measured from acinar cells treated with RC (12%) for 3.5 hr±FK506. (n=3). *, #, P<0.05, relative to the control or RC alone, respectively.

Figure 10A:
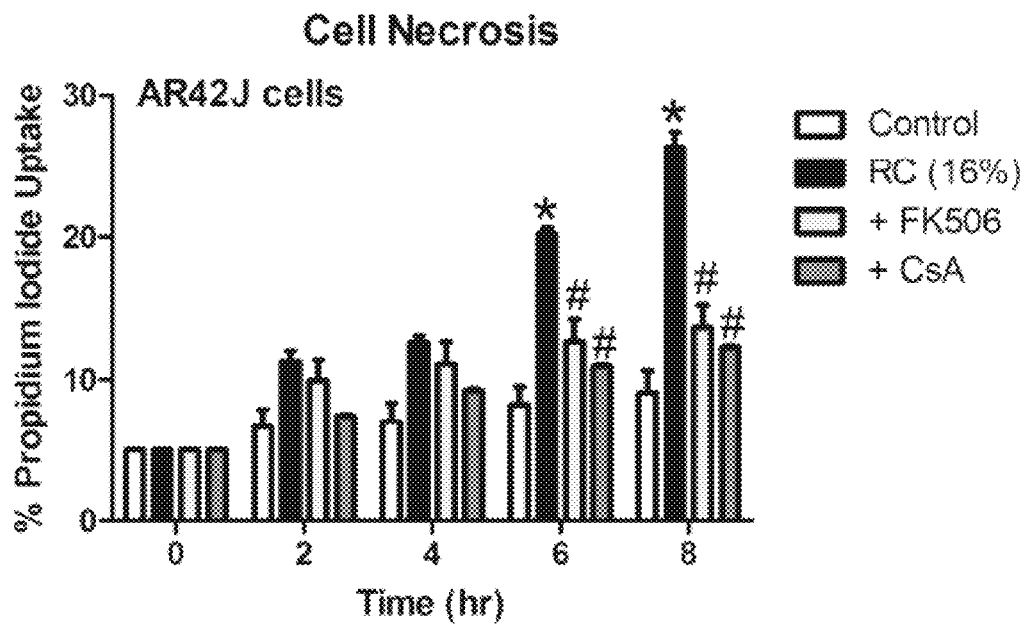
Figure 10B:
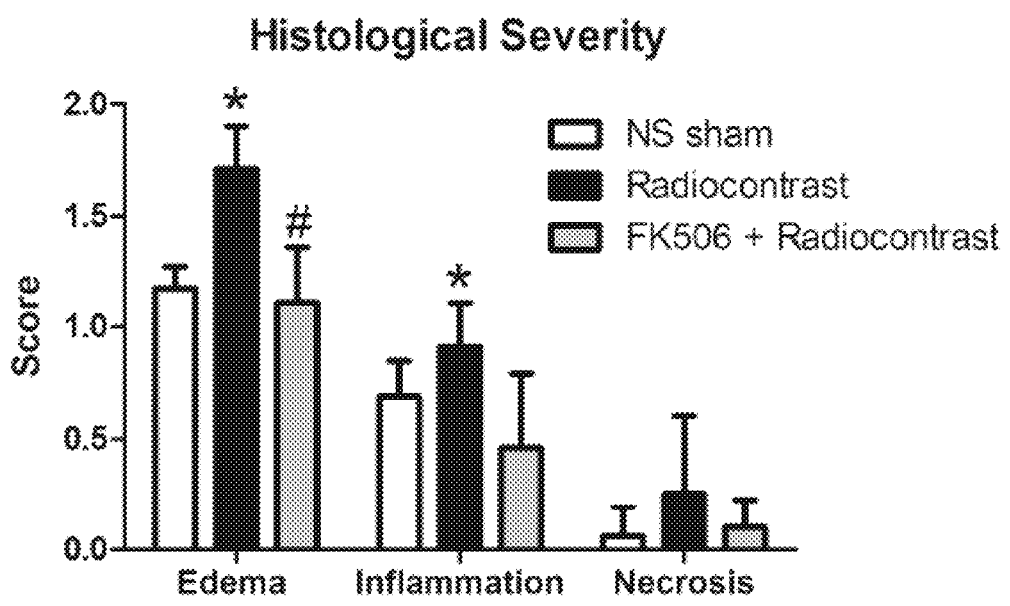
Figure 10C:
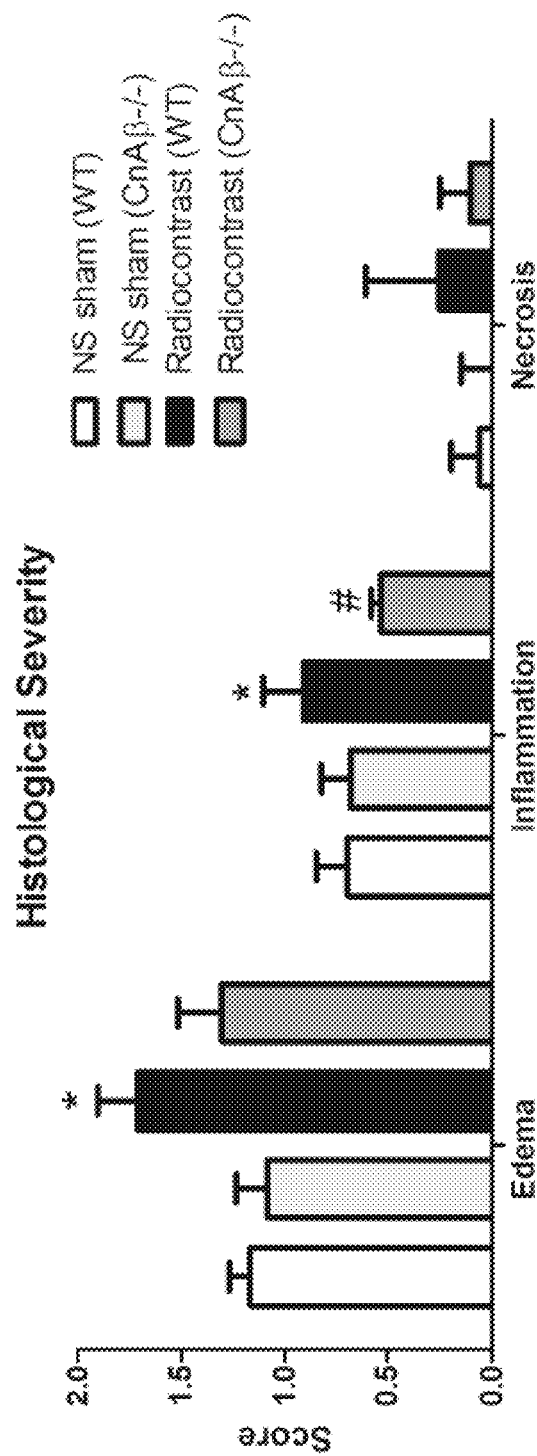

FIG. 10A-10C. RC-induced cell necrosis in AR42J cells is dependent on calcineurin, and the histological subscores from the PEP model. (A) RC (12%)-induced acinar cell necrosis was prevented by FK506 (24 μM) or CsA (16 μM). (n=3). *, #, P<0.05, relative to the control or RC alone, respectively. HE-stained sections of the pancreatic head were collected 24 hr after RC infusion (B) in the presence or absence of pharmacologic (FK506; 1 mg/kg) calcineurin inhibition or (C) by comparing wildtype mice (WT) with CnAβ knockout mice. Histological severity of pancreatitis was graded by the presence of edema, inflammatory infiltrate, and necrosis. (n=5 animals per group). *, P<0.05 relative to NS sham.

FIG. 11A-11F. PEP is dependent on calcineurin. (A) Schema for the administration of FK506 (1 mg/kg) relative to the infusion of RC. (B & F) Representative H&E sections from the pancreatic head. (C & F) Overall severity score (left), and serum amylase measurements (right). (n=5 animals per group). (D) Bioluminescence from the pancreas of mice that had received intraductal infusions of AAV6-NF-κB-luciferase. Quantification of the pancreatic NF-κB-bioluminescent signal over 36 hr (n=3 animals per group). (F) Gene expression for IL-6, GADD45B, and IL-1β from the pancreatic head (n=3). *, #, P<0.05 compared with NS sham and RC alone, respectively.

Figure 12A:
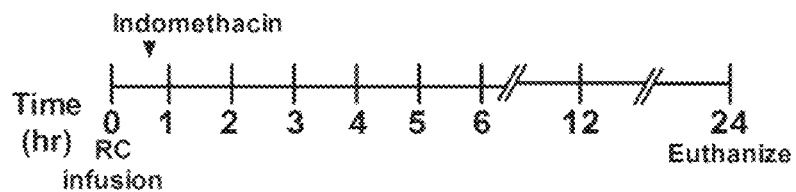
Figure 12B:
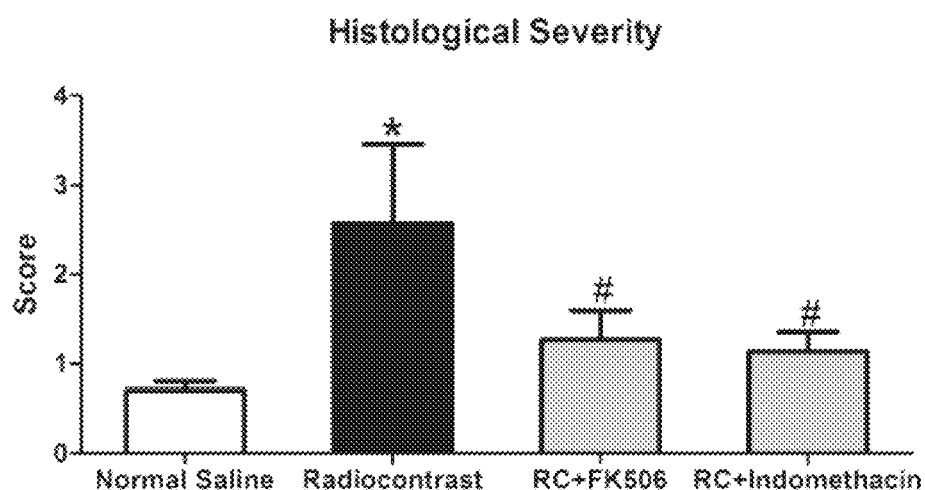
Figure 12C:
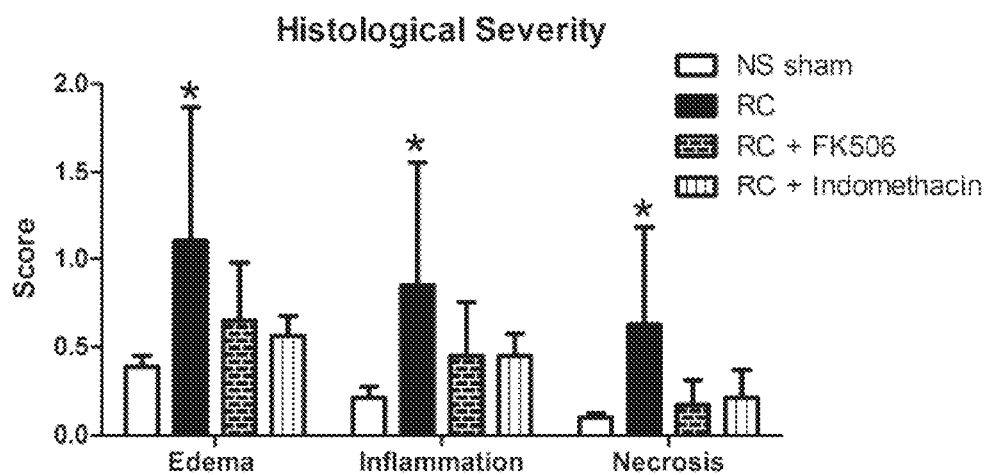
Figure 13A:
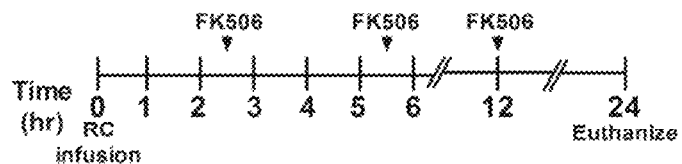
Figure 13B:
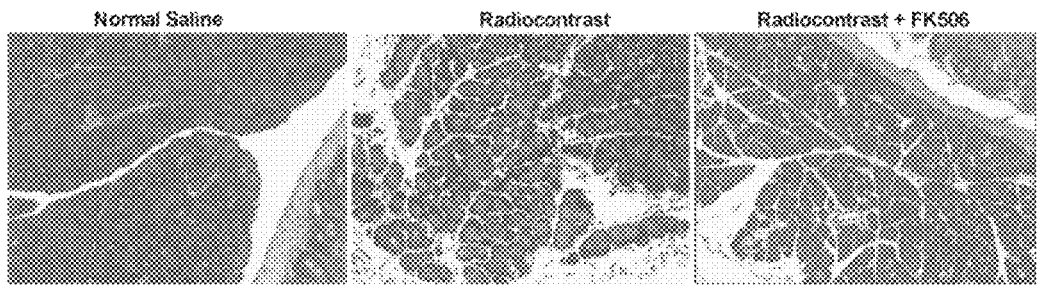
Figure 13C:
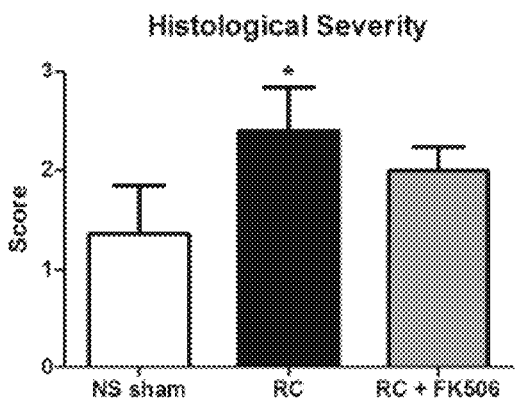
Figure 13D:
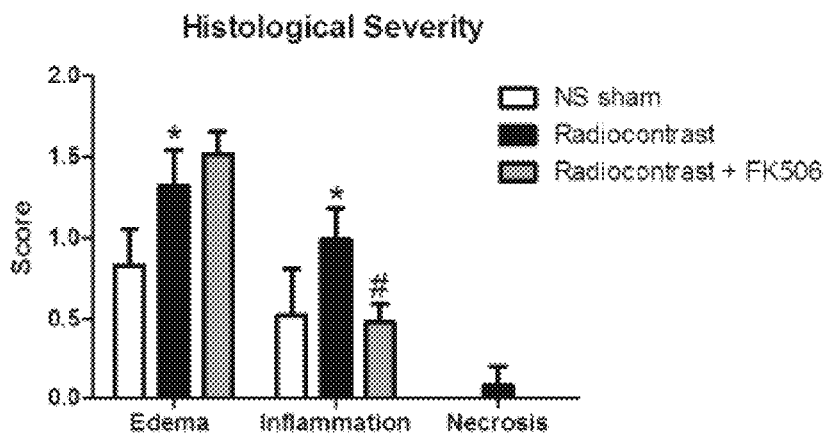

FIG. 12A-12C. FK506 pretreatment is as effective as NSAID pretreatment during RC-induced pancreatitis. (A) Schema for the administration of Indomethacin (7 mg/kg; IP) after the infusion of RC. (B) Overall severity score and subscore (C) following RC±Indomethacin.*, #, P<0.05 compared with NS sham and RC alone, respectively.

FIG. 13A-13D. FK506 given after PEP induction reduces pancreatic inflammation. (A) Schema for the administration of FK506 (1 mg/kg) after the infusion of RC. (B) Representative HE sections from the pancreatic head following RC±FK506. (C) Overall severity score (left) and subscore (right) following RC±FK506. (D) Serum amylase (left) and IL-6 (right) measured 24 after RC infusion±FK506. (n=5 animals per group).*, #, P<0.05 compared with NS sham and RC alone, respectively.

Figure 14A:
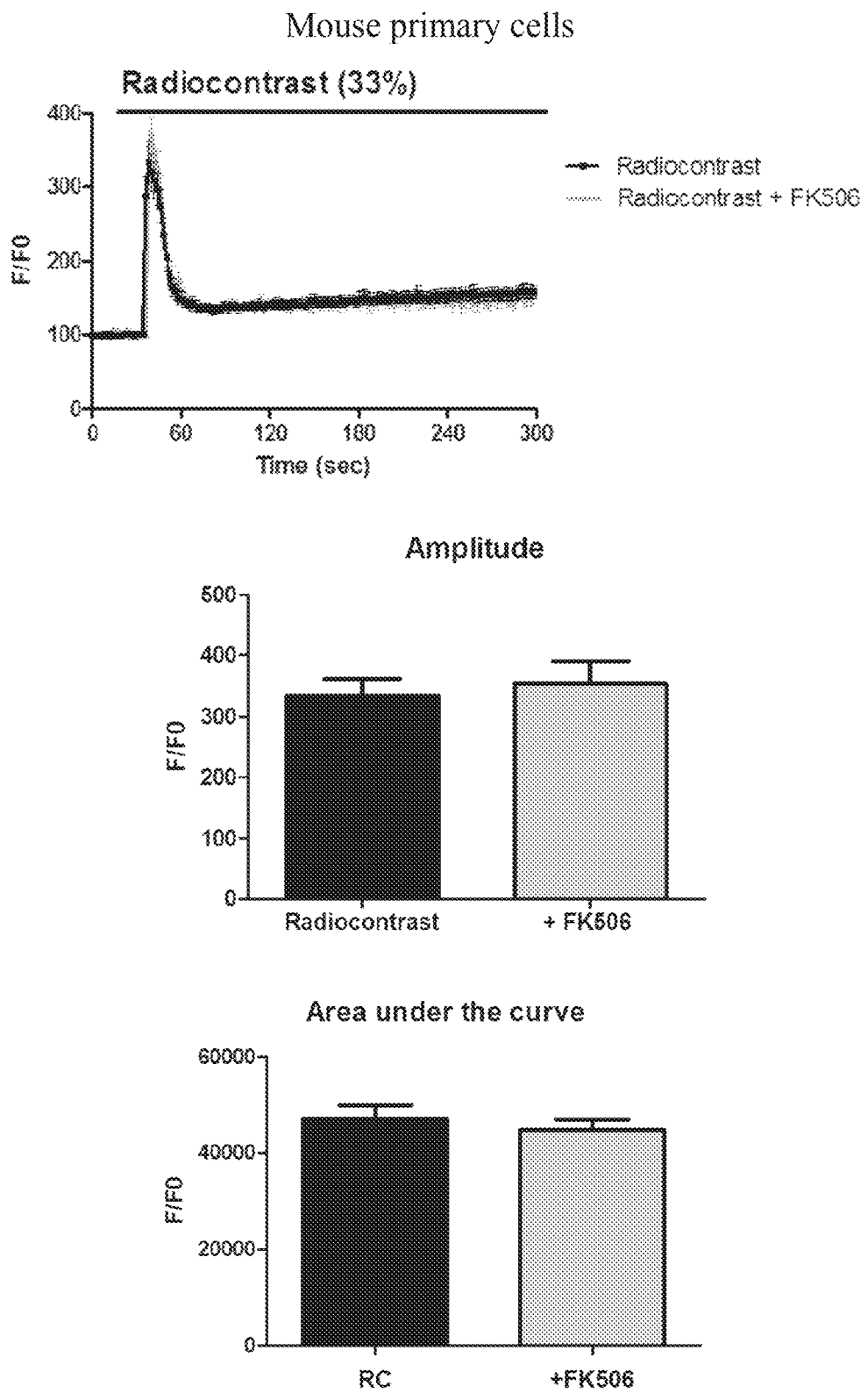
Figure 14B:
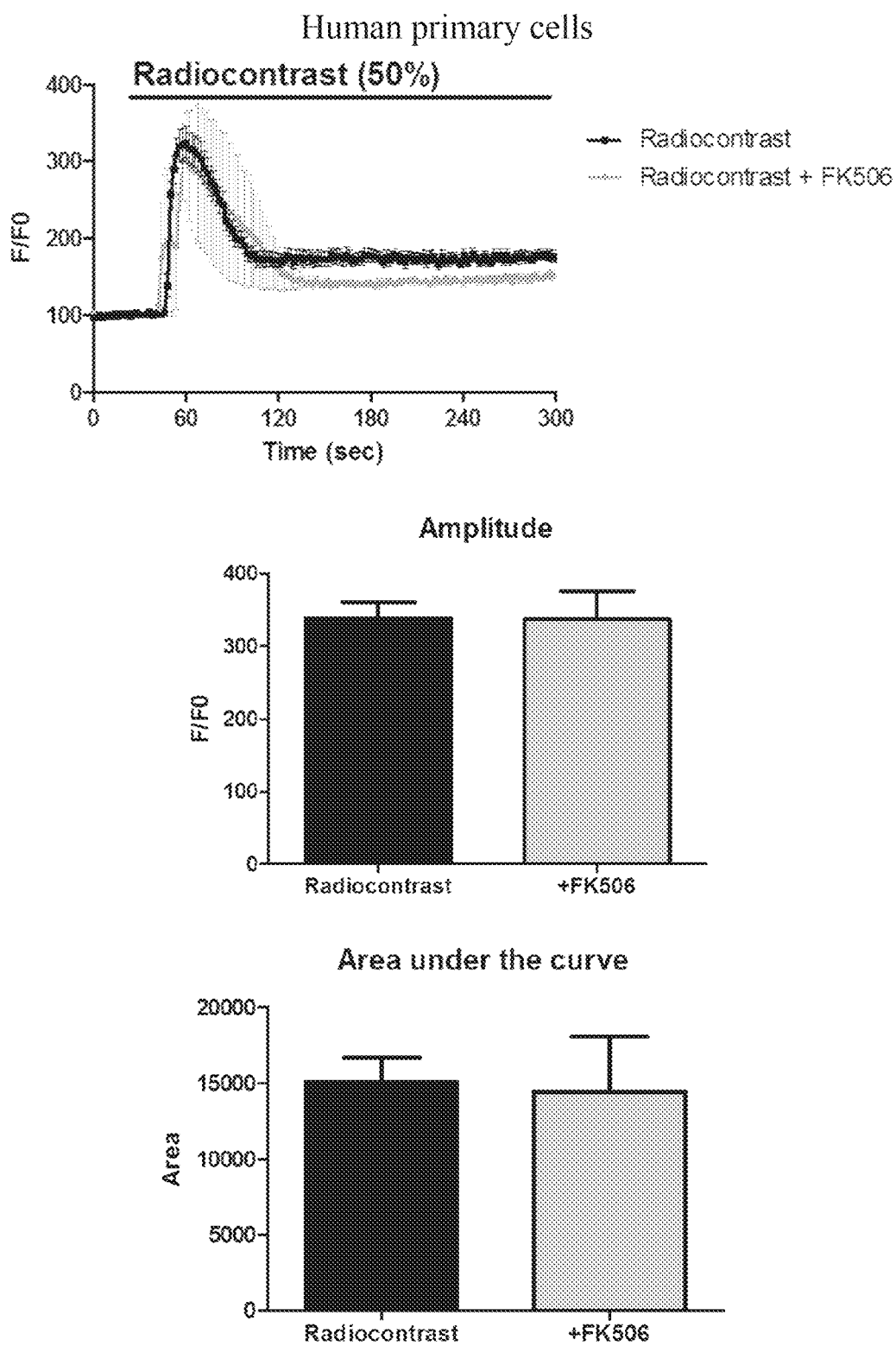
Figure 14C:
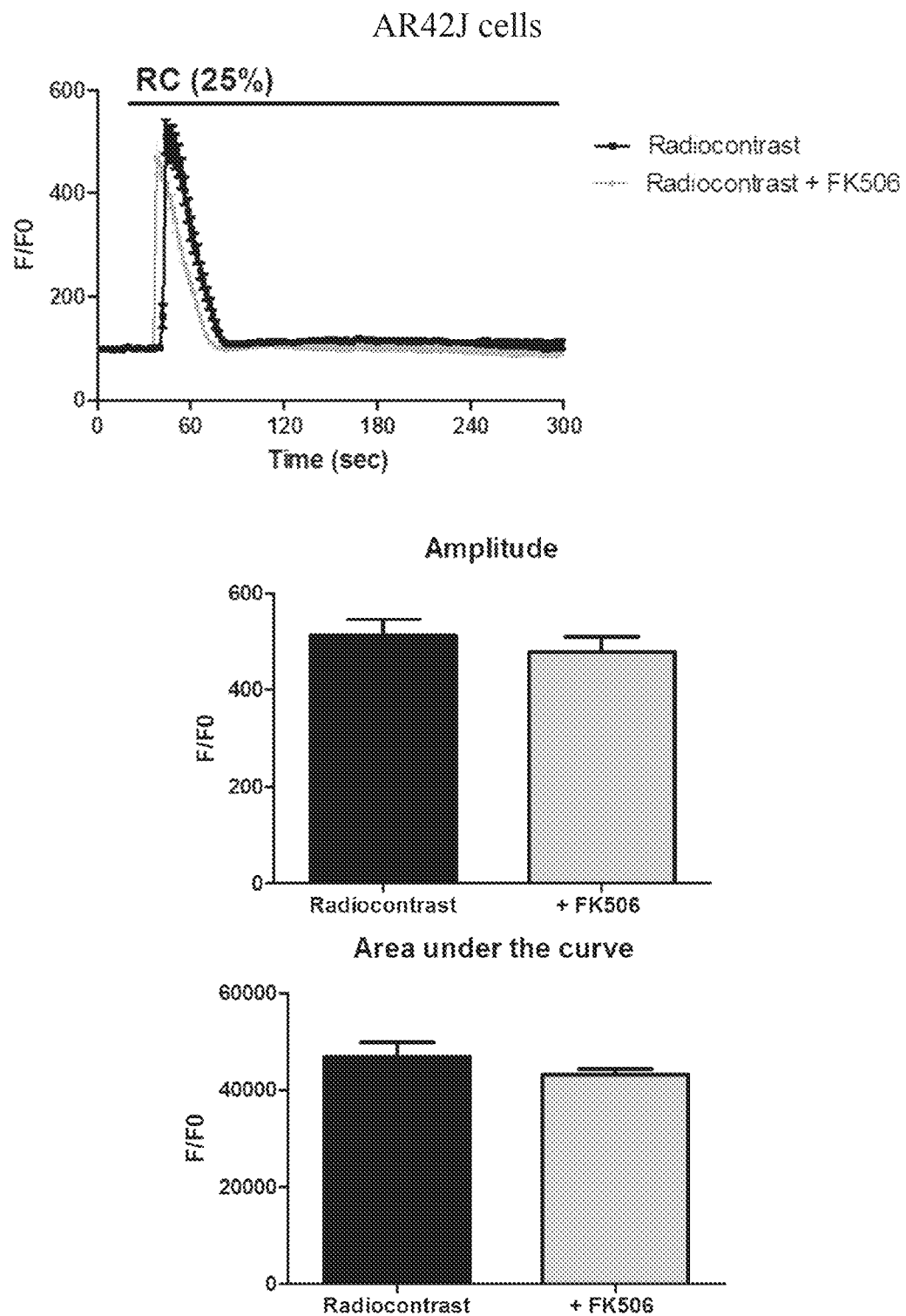

FIG. 14A-14C. The RC-induced acinar cell Ca$^{2+}$ signals are not modulated by calcineurin. Summation of whole cell tracings from (A) mouse primary acinar cells, (B) human primary acinar cells, or (C) AR42J cells loaded with Fluo-4AM and perifused with RC (25-50%). Quantification of amplitude and area under the cure is shown on right. (n=20-30 cells per condition).

Figure 15:
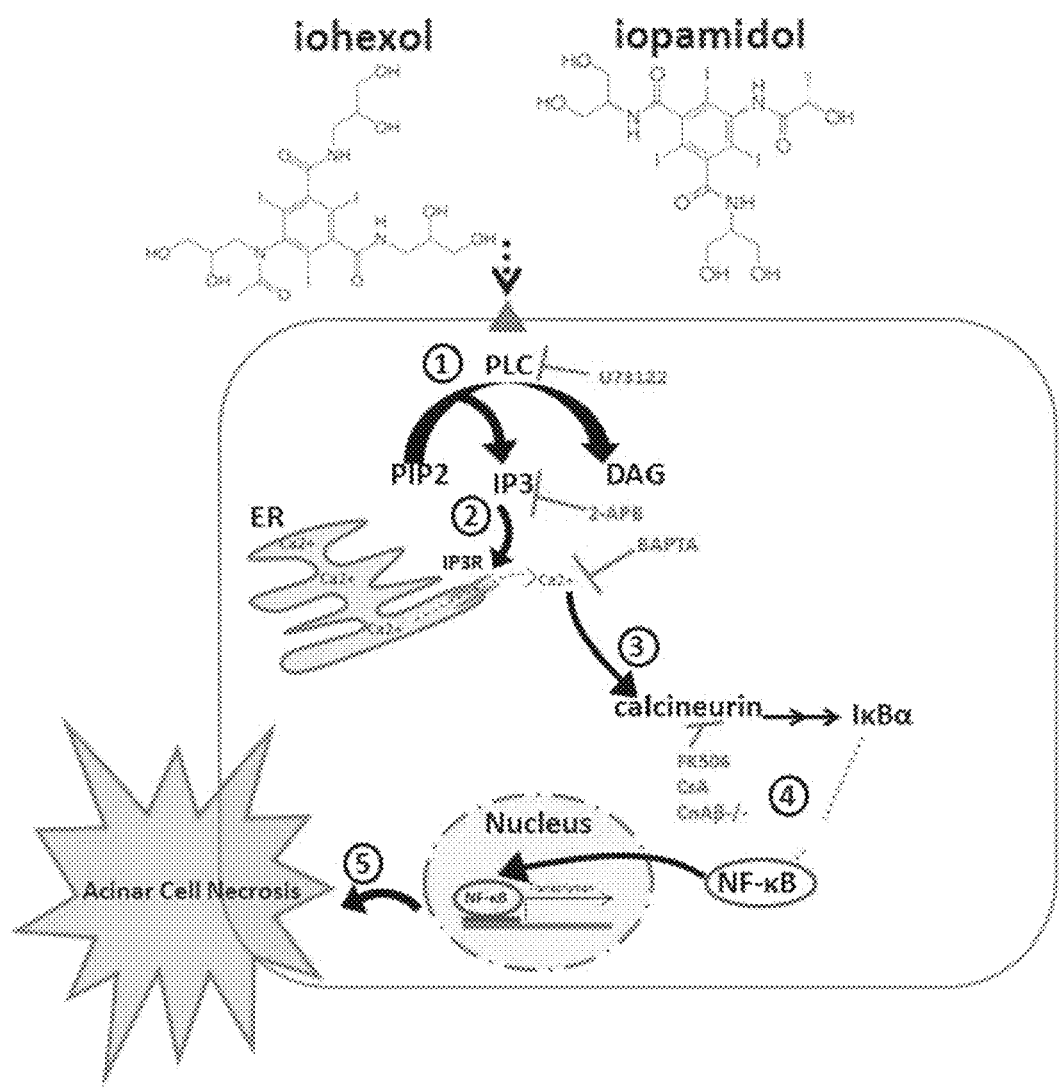

FIG. 15. Hypothesis diagram. RC exposure causes acinar cell: (1) activation of PLC; (2) generation of IP3 resulting in IP3R-induced Ca$^{2+}$ release; (3) downstream activation of calcineurin; (4) translocation of NF-κB to the nucleus, leading to (5) acinar cell injury and pancreatitis. The inhibitory scheme is shown in red. PIP2, phosphatidylinositol 4,5-bisphosphate; DAG, diacyglycerol.

Figure 16A:
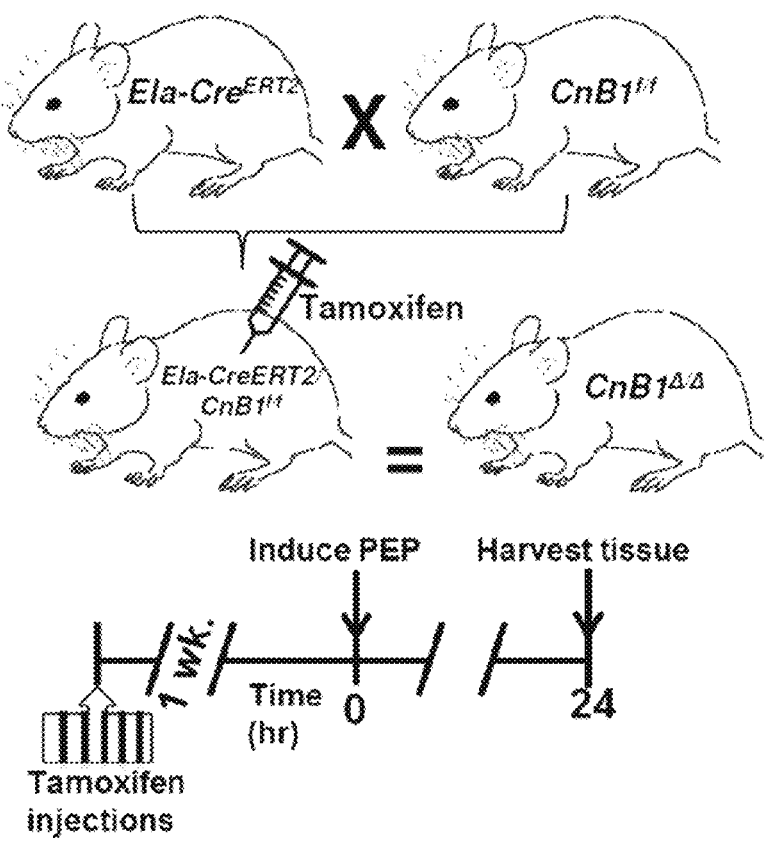
Figure 16B:
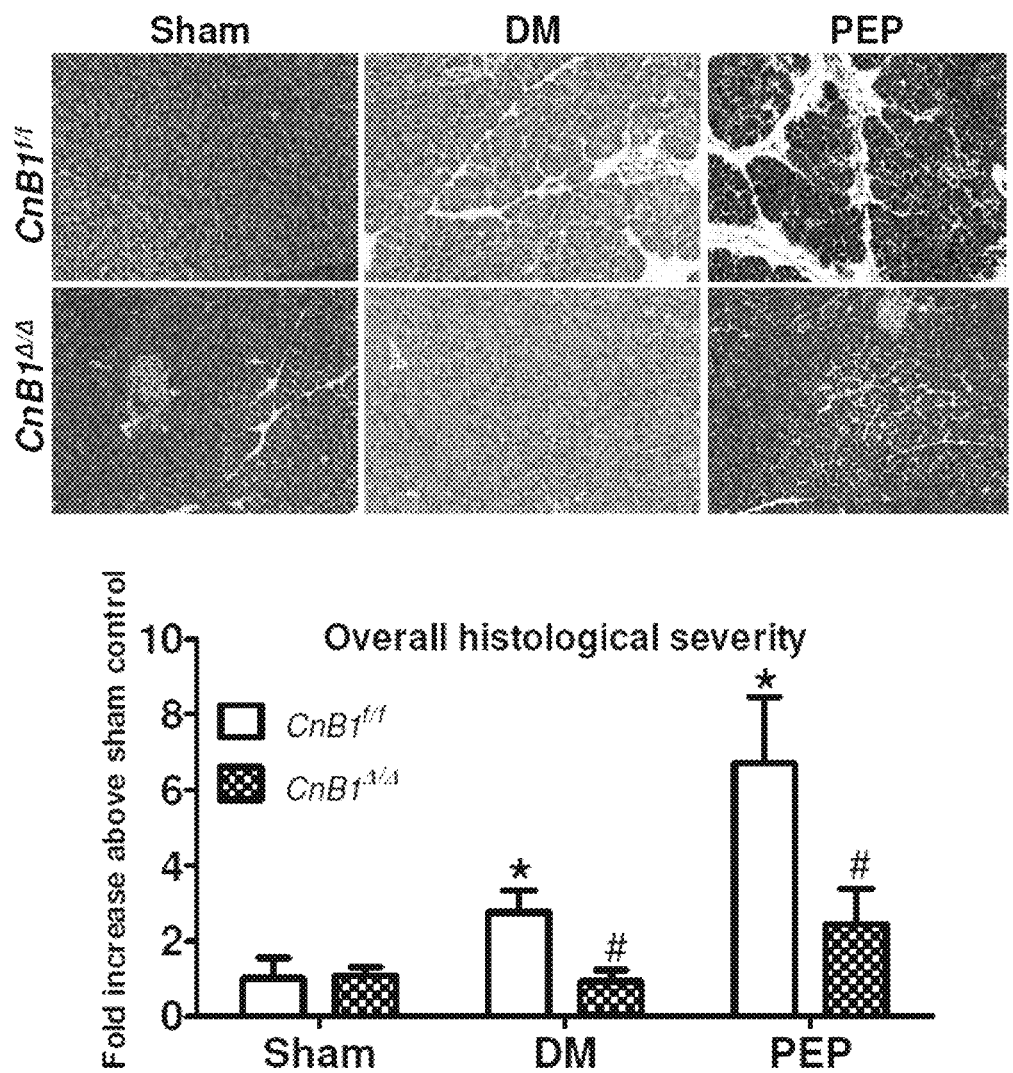
Figure 16C:
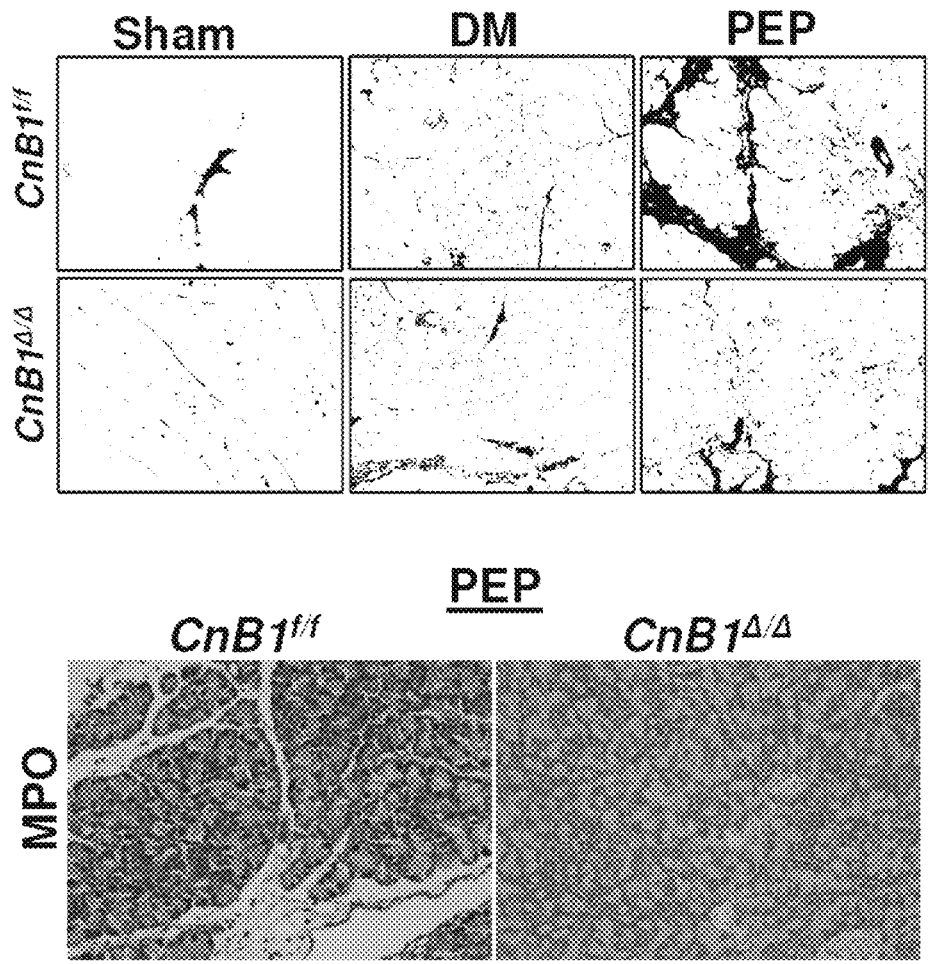

FIG. 16A-16C. Acinar cell-specific deletion of Cn using Cre-lox recombination protects against PEP in mice. (A) Acinar cell Cn knockout line (Cn$^{Δ/Δ}$) induced by crossing Ela-CreERT2 mice with CnB$^{f/f}$ mice, followed by tamoxifen administration. (B) Representative HE sections of the pancreatic head from sham-operated, duct-manipulated (DM), and post-ERCP pancreatitis (PEP) modeled conditions, along with histological severity scoring. (C) Edema, assessed by image thresholding, on left and MPO staining on right.

FIG. 17A-17F. Confirmation of the Ela-CreERT2/CnB1$^{f/f}$ genotype and CnB1 deletion. (A) Schema of the CnB1 knock-in allele that contains loxP sites and (B) schema of the Ela-CreERT2 transgene. Red arrows denote forward and reverse primers designed to generate the 5' and 3' loxP site PCR product of 575 and 289 bp, respectively. Blue arrows denote CnB1 spanning region of 2803 bp. (C) Agarose gel showing PCR products of expected size obtained to verify the loxP sites and presence of the Ela-CreERT2 transgene. (D) Illustration of the CnB1 gene containing loxP sites. Red arrows denote forward and reverse primers designed to identify the CnB1$^{Δ/Δ}$ resulting in a 168 bp fragment. (E) Two percent agarose gel showing PCR products that verify CnB1 deletion in the pancreas. (F) NFAT luciferase activity is markedly diminished in acinar cells from CnB1$^{Δ/Δ}$ but not from CnB1$^{f/f}$ controls, in response to radiocontrast (RC). *, #, P<0.05 relative to negative and positive controls, respectively.

FIG. 18A-18E. Acinar cell-specific deletion of Cn in the tamoxifen-induced Ela-CreERT2/CnB1$^{f/f}$ mouse protects against the components of pancreatic damage that define PEP. (A) Image of the en bloc pancreas and adjacent organs, including duodenum (D) and spleen (Sp). Dashed white line surrounds the region of the pancreas next to the duodenum which was used for blinded histological grading. (B) Edema, (C) inflammation, and (D) necrosis scoring from the pancreatic head of sham-operated, duct-manipulated (DM), and post-ERCP pancreatitis (PEP) modeled conditions. (E) MPO scoring from IHC-stained tissue sections. (n=5 animals per condition). *, #, P<0.05 relative to non-floxed out control sham and each positive control, respectively.

FIG. 19A-19D. Acinar cell-specific deletion of Cn protects against bile acid-infusion pancreatitis in mice. (A) On left, representative HE sections and, on right, overall histological severity. Histological subscoring for (B) edema, (C) inflammation, and (D) necrosis. (n=5 animals per condition). *, #, P<0.05 relative to non-floxed out control sham and each positive control, respectively.

Figure 20A:
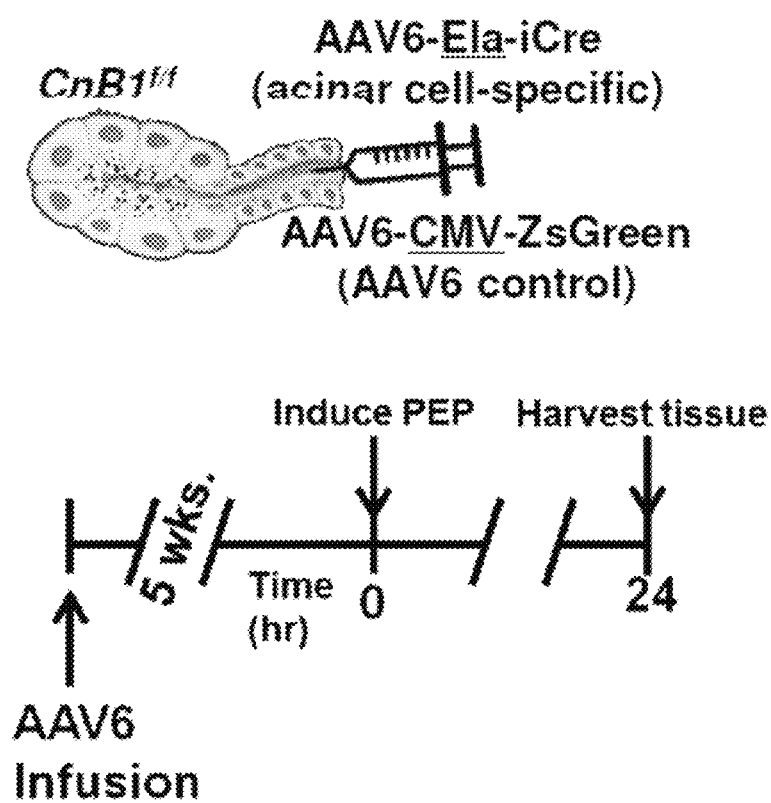
Figure 20B:
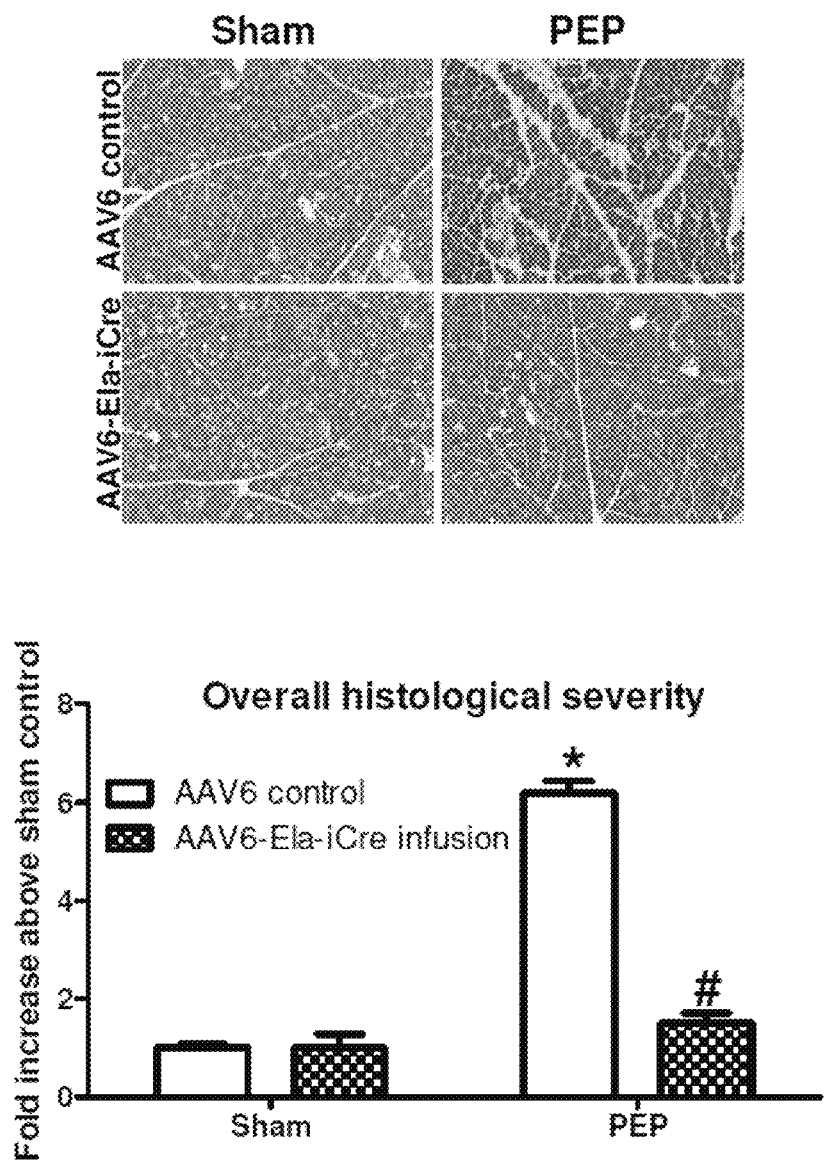
Figure 20C:
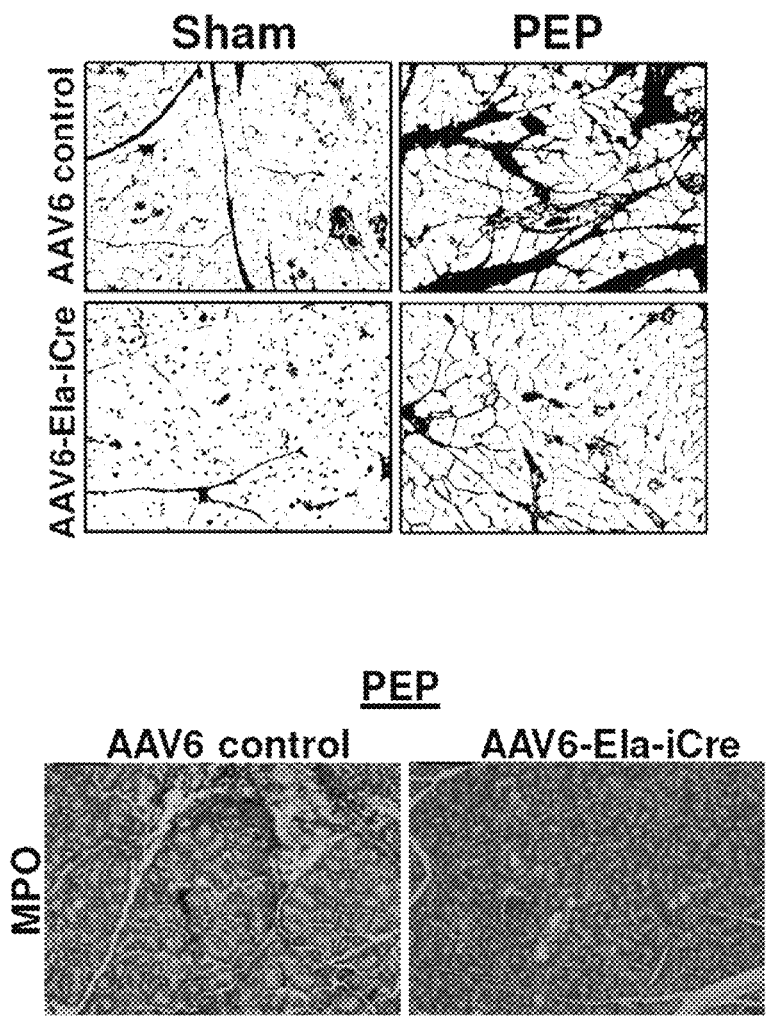

FIG. 20A-20C. Acinar cell-specific deletion of Cn using intraductal infusion of AAV6-Ela-iCre protects against PEP in mice. (A) Schema for intraductal infusion of AAV6-Ela-iCre (acinar cell-specific) or AAV6-CMV-ZsGreen (AAV6 control) in a CnB1$^{f/f}$ mouse line. (B) Representative HE sections from sham control and PEP conditions, along with histological severity scoring. (n=5 animals per condition). (C) Edema and MPO. (n=5 animals per condition). *, #, P<0.05 relative to control sham and each positive control, respectively.

FIG. 21A-21F. Intraductal infusion of a novel AAV6-Ela-iCre construct targets the pancreatic acinar cell and protects against PEP. (A) Schema of the AAV6-Ela-iCre plasmid. (B) Lox-Stop-Lox tdTomato Red reporter mice were infused with AAV6-Ela-iCre to test the specificity of viral cargo delivery. Red fluorescence was observed in the pancreas and excluded from neighboring organs such as the small intestine (SI), liver (L), and spleen (Sp). In the tissue sections, the dashed white line separates pancreas (left) from duodenum (right). (C) Edema, (D) inflammation, and (E) necrosis scoring from the pancreatic head of sham-operated and post-ERCP pancreatitis (PEP) modeled conditions. (F) MPO scoring. (n=5 animals per condition). *, #, P<0.05 relative to the negative and positive control, respectively.

Figure 22A:
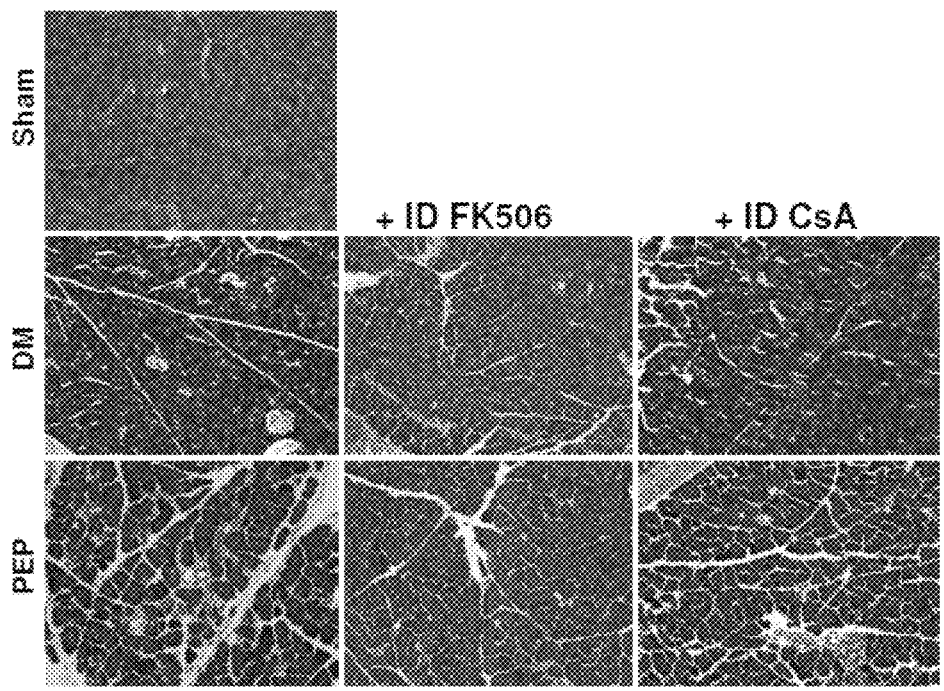
Figure 22B:
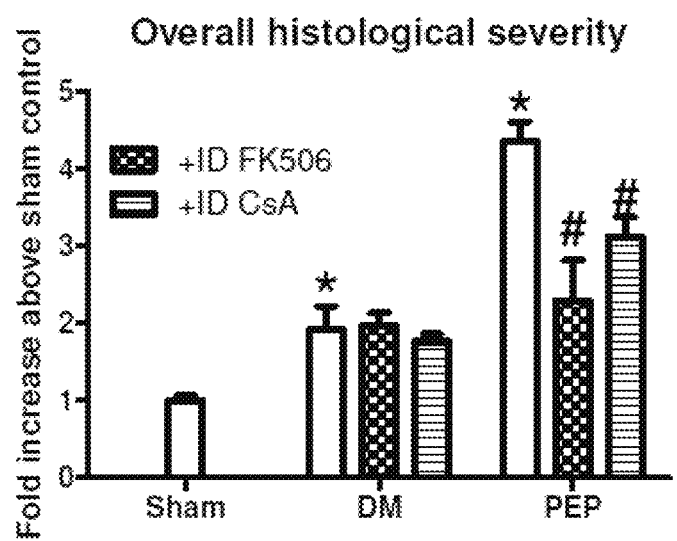

FIG. 22A-22B. Intraductal (ID) administration of Cn inhibitors along with the radiocontrast infusion prevents PEP. (A) Representative HE sections from sham-operated, duct-manipulated (DM), and post-ERCP pancreatitis (PEP) modeled conditions. The Cn inhibitors FK506 (1 μM) or CsA (10 μM) were delivered with the radiocontrast solution into the intrapancreatic duct. (B) Histological severity scoring. (n=5 animals per condition). *, #P<0.05 relative to the control sham and each positive control, respectively.

FIG. 23A-23D. Intraductal infusion of Cn inhibitors reduces the components of pancreatic damage that define PEP. Histological subscoring for (A) edema, (B) inflammation, and (C) necrosis. (D) Serum amylase 6 h after PEP induction (n=5 animals per condition). *, #P<0.05 relative to the negative and positive control, respectively.

5. DETAILED DESCRIPTION

For clarity of description, and not by way of limitation, the detailed description is divided into the following subsections:

(a) radiocontrast agents;
(b) calcineurin inhibitors;

(c) antioxidants;
(d) radiocontrast medium compositions and kits;
(e) methods of treatment; and
(f) assay systems.

A radiocontrast medium for use according to the invention comprises the following three elements: (i) a radiocontrast agent; (ii) a calcineurin inhibitor; and (iii) an antioxidant.

5.1 Radiocontrast Agents

A radiocontrast medium for use according to the invention comprises, as one element, a radiocontrast agent. A radiocontrast agent is a composition that improves visibility of internal bodily structures in X-ray based imaging techniques such as, but not limited to, computerized tomography and radiography. As a particular, non-limiting example, a radiocontrast agent for use in a radiocontrast medium of the invention is an agent suitable for imaging in endoscopic retrograde cholangiopancreatography ("ERCP").

In non-limiting embodiments of the invention, the amount of radiocontrast agent is effective in promoting imaging in an imaging study.

In non-limiting embodiments of the invention, the radiocontrast agent is water soluble.

In non-limiting embodiments of the invention, the radiocontrast agent is non-ionic.

In non-limiting embodiments of the invention, the radiocontrast agent is a non-ionic monomer, for example, a low osmolality contrast agent, such as, but not limited to, iopamidol (Isovue®), iohexol (Omnipaque®), ioversol (Optiray™), iopromide (Ultravist®), ioxilan (Oxilan®), or iopentol (Imagopaque).

In non-limiting embodiments of the invention, the radiocontrast agent is a non-ionic dimer, for example, a low osmolality contrast agent, such as, but not limited to, iotrolan (Iotrol) or iodixanol (Visipaque™).

In non-limiting embodiments of the invention, the radiocontrast agent is an ionic radiocontrast agent.

In non-limiting embodiments of the invention, the radiocontrast agent is an iodinated radiocontrast agent.

5.2 Calcineurin Inhibitors

A second component of a radiocontrast medium of the invention is one or more calcineurin inhibitor, which may inhibit the action of calcineurin directly or indirectly. In a specific non-limiting embodiment, the calcineurin which is inhibited is human calcineurin.

In non-limiting embodiments of the invention, the amount of calcineurin inhibitor present in a radiocontrast medium of the invention is, together with the antioxidant, effective in decreasing the risk of pancreatitis in a subject.

In non-limiting embodiments of the invention, the amount of calcineurin inhibitor present in a radiocontrast medium of the invention is, together with the antioxidant, effective in decreasing the risk of post-ERCP pancreatitis in a subject.

In non-limiting embodiments of the invention, the amount of calcineurin inhibitor present produces a local concentration in the pancreas that reduces radiocontrast-mediated increase in NF-κB (nuclear factor of kappa light chain enhancer B) and/or NFAT activity by at least about 20 percent or at least about 30 percent in an acinar cell culture.

In certain non-limiting embodiments, the calcineurin inhibitor is cyclosporine A.

In certain non-limiting embodiments, the calcineurin inhibitor is FK506 (tacrolimus).

In non-limiting embodiments of the invention, where the calcineurin inhibitor is cyclosporine A, the amount of cyclosporine A comprised in a radiocontrast medium of the invention may be an amount that results in a local concentration of at least 5 μM, or at least 10 μM, or at least 16 μM, or about 10 μM, or about 16 μM, or between about 5 μM and 10 μM, or between about 5 and 20 μM, or between about 10 and 20 μM, and/or up to 20 μM or up to 30 μM.

In non-limiting embodiments of the invention, where the calcineurin inhibitor is FK506, the amount of FK506 comprised in a radiocontrast medium of the invention may be an amount that results in a local concentration of at least 10 or at least 20 μM, or at least 30 μM or about 20 μM, or about 24 μM, or between about 10 and 40 μM, or between about 20 and 30 μM, and/or up to 30 μM or up to 40 μM.

5.3 Antioxidants

A third component of a radiocontrast medium of the invention is an antioxidant.

In a specific, non-limiting embodiment of the invention, the antioxidant is N-acetylcysteine.

In a specific, non-limiting embodiment of the invention, the antioxidant is sodium selenite.

In a specific, non-limiting embodiment of the invention, the antioxidant is vitamin E.

In a specific, non-limiting embodiment of the invention, the antioxidant is beta-carotene.

In non-limiting embodiments of the invention, the amount of antioxidant present in a radiocontrast medium of the invention is, together with the calcineurin inhibitor, effective in decreasing the risk of pancreatitis in a subject.

In non-limiting embodiments of the invention, the amount of antioxidant present in a radiocontrast medium of the invention is, together with the calcineurin inhibitor, effective in decreasing the risk of post-ERCP pancreatitis in a subject.

In non-limiting embodiments of the invention, where the antioxidant is N-acetylcysteine, the amount of N-acetylcysteine comprised in a radiocontrast medium of the invention may be at least about 2 mM or between about 1 and 3 mM.

5.4 Radiocontrast Medium Compositions and Kits

In non-limiting embodiments, the present invention provides for a radiocontrast medium for use according to the invention comprises the following three elements: (i) a radiocontrast agent; (ii) a calcineurin inhibitor; and (iii) an antioxidant, in amounts effective in radioimaging in a subject with reduced risk of post-imaging pancreatitis relative to the radiocontrast agent administered without the calcineurin inhibitor and the antioxidant. Non-limiting examples of suitable radiocontrast agent, calcineurin inhibitor, and antioxidant components are set forth in the sections above.

In certain non-limiting embodiments, the present invention provides for a pharmaceutical composition comprising the radiocontrast medium of the invention, further comprising a physiologically suitable solvent such as water. Said pharmaceutical composition may further comprise one or more formulating agents such as, but not limited to, a buffer and/or a preservative.

In certain non-limiting embodiments, a calcineurin inhibitor and/or an antioxidant may be added to a commercial formulation of a radiocontrast agent.

In certain non-limiting embodiments, the present invention provides for a kit comprising therapeutic amounts of (i) a radiocontrast agent; (ii) a calcineurin inhibitor; and/or (iii) an antioxidant, which may be combined prior to use.

In certain non-limiting embodiments, the present invention provides for a kit comprising therapeutic amounts of (i) a radiocontrast agent; (ii) a calcineurin inhibitor; and/or (iii) an antioxidant, which may be administered separately, or in subcombination, to the subject being treated.

5.5 Methods of Treatment

According to the present invention, a radiocontrast medium according to the invention may be used instead of conventional imaging medium in an imaging procedure to reduce the risk of post-procedure pancreatitis relative to the risk in a control subject where the imaging procedure was performed using conventional imaging medium. For example, the control subject may have a similar clinical profile as the treated subject.

In non-limiting embodiments, the invention provides for a method of radioimaging a pancreas, gallbladder, and/or biliary tree in a subject, comprising introducing, into the pancreas, gallbladder and/or biliary tree of the subject, a radiocontrast medium as set forth above, comprising (i) a radiocontrast agent; (ii) a calcineurin inhibitor; and (iii) an antioxidant, with the advantage that the subject would have a reduced risk of developing post-imaging pancreatitis relative to a subject receiving radiocontrast agent without calcineurin inhibitor and without antioxidant.

In non-limiting embodiments, the subject may be a human subject or a non-human subject such as a dog, a cat, a horse, a pig, a cow, a sheep, a goat, a mouse, a rat, a hamster, a guinea pig, or a rabbit.

In non-limiting embodiments, a radiocontrast medium according to the invention may be used instead of conventional medium in an ERCP procedure to reduce the risk of post-ERCP pancreatitis relative to the risk in a control subject where the imaging procedure was performed using conventional imaging medium.

For example, but not by way of limitation, a subject may be considered to suffer pancreatitis if the subject exhibits new or worsened abdominal pain and an increase in serum amylase, for example to a level at least two or at least three times the upper limit considered normal, measured more than 24 hours after the procedure.

Subjects who may particularly benefit from the invention are those who are at risk for developing post-procedure pancreatitis, including, but not limited to, patients having one or more of the following features: sphincter of Oddi dysfunction, young age, female sex, and/or a previous history of pancreatitis, and/or where, during the imaging procedure, cannulation was difficult, there were multiple injections into the pancreatic duct, there was a precut sphincterotomy or a pancreatic sphincterotomy.

The radiocontrast medium of the invention may be administered to the subject prior to or during an imaging procedure. It may be administered by injection or infusion or local instillation. For example, but not by way of limitation, it may be administered via the biliopancreatic duct or intravenously. Any combination or all three components of the radiocontrast medium may be administered together or separately to achieve the combination in the patient.

Further to use of the radiocontrast medium of the invention, one or more of the following measures may be taken to further reduce risk of, and/or to limit damage by, pancreatitis: (i) treatment with one or more pancreatic enzyme (secretin)-inhibiting drug such as atropine, calcitonin, somatostatin, glucagon and/or flurouracil; (ii) treatment with one or more protease-inhibiting drug such as aprotinin, gabexate masylate, camostate, and/or phospholipase A2; (iii) treatment with one or more anti-inflammatory agent such as a nonsteroidal antiinflammatory drug (e.g. indomethacin), allopurinol, a prostaglandin inhibitor, a platelet activating factor antagonist, a platelet activator factor acetyl hydrolase, or Lexipant; (iv) reduction of sphincter of Oddi pressure by nitroglycerine, nifedipine, or lidocaine; (v) treatment with an antibiotic; (vi) placement of a stent in the pancreatic duct; and/or (vii) treatment with an anti-metabolite such as 5-flurouracil.

In certain non-limiting embodiments, the present invention provides for a method of reducing the risk of post-imaging pancreatitis in a subject in need of such treatment comprising using, as an agent for imaging the pancreas and related structures of the subject, a radiocontrast medium (as described herein) comprising (i) a radiocontrast agent; (ii) a calcineurin inhibitor; and (iii) an antioxidant in amounts such that the risk of post-imaging pancreatitis in the subject is reduced.

5.6 Assay Systems

In certain non-limiting embodiments, the present invention provides for an assay system that may be used to identify an agent that reduces the risk of post-imaging pancreatitis. The assay system may be an in vitro or an in vivo assay.

In certain non-limiting embodiments, the assay is an in vitro assay comprising primary acinar cells or cells of a pancreatic cell line into which nucleic acid has been introduced encoding, in expressible form (e.g., operably linked to an inflammation-inducible promoter, such as an IL-4 promoter), NF-κB or NFAT, fused to a reporter gene, for example NF-κB-luciferase or NFAT-luciferase. For example, said nucleic acid may be introduced either as naked DNA or via a viral vector, such as, but not limited to, an adenovirus, adeno-associated virus, or lentiviral vector. Where a pancreatic cell line is used, it can be cultured under conditions which promote an acinar cell-type phenotype. A particular example of such a culture system is set forth in working example in section 6, below, the features of which are incorporated by reference into this detailed description.

Accordingly, in non-limiting embodiments the invention provides for a method of determining whether a test compound can be used to reduce the risk of post-imaging pancreatitis, comprising (i) providing a cell which is a primary acinar cell or a pancreatic cell line cell, into which a nucleic acid has been introduced encoding NFκB fused to a detectable reporter or NFAT fused to a detectable reporter, operably linked to an inflammation-inducible promoter; (ii) exposing the cell to a radiocontrast agent and the test compound and determining the amount of NFκB-reporter or NFAT-reporter, respectively; and (iii) comparing the amount of NFκB-reporter or NFAT-reporter determined in (ii) to the amount of NFκB-reporter or NFAT-reporter present in a control cell exposed to the radiocontrast agent under comparable conditions but in the absence of test compound; where if the amount of NFκB-reporter or NFAT-reporter determined in (ii) is less than the amount of NFκB-reporter or NFAT-reporter determined in (iii), the test compound can be used to reduce the risk of post-imaging pancreatitis.

In non-limiting embodiments, the present invention provides for an in vivo assay where an NFκB or NFAT-reporter construct as described above is introduced into pancreatic cells of an animal in vivo, for example via direct instillation into the pancreas. A specific non-limiting example is an AAV vector carrying nucleic acid encoding a NFκB-luciferase fusion, operably linked to a promoter, which may be used to introduce the fusion construct into pancreatic cells in vivo. See working example in section 6. The in vivo assay can be used analogously to the in vitro assay to evaluate the ability of a test compound to reduce radiocontrast-induced increases in NFκB-reporter or NFAT-reporter.

In certain non-limiting embodiments, the present invention provides for an in vivo assay where a test compound is introduced into pancreatic cells of an animal in vivo, for example via direct instillation into the pancreas, as well as an analogous in vitro assay, which may be used to evaluate the ability of a test compound to reduce the risk of post-imaging pancreatitis or a maker thereof, such as, but not limited to, radiocontrast-induced increases in serum amylase; overall histological severity, including but not limited to edema, inflammatory infiltration, and necrosis; and/or increases in myeloperoxidase (MPO).

6. EXAMPLE: EXAMPLE: RADIOCONTRAST EXPOSURE INDUCES PANCREATIC NF-κβ AND PANCREATITIS BY TRIGGERING CALCIUM AND CALCINEURIN

6.1. Materials and Methods

Reagents and animals. RC refers primarily to iohexol (Omnipaque 300; GE Healthcare; Princeton, N.J.) which is categorized as a low osmolality (672 mOsm/kg water), nonionic, iodinated (300 mg/iodine/ml) contrast medium. A second RC iopamidol (Isovue 300; Bracco Diagnostics; Monroe Township, N.J.) which is in the same category as iohexol, was used to verify key findings from the study, and its use is specified in the text. NFAT-luciferase (Qiagen; Valencia, Calif.), NF-κB-luciferase (Vector Biolabs; Philadelphia Pa.), and constitutively active calcineurin (ΔCn) adenoviruses were constructed as previously described[10-12]. All other reagents were purchased from Sigma-Aldrich (St. Louis, Mo.), unless specified otherwise. Male Swiss Webster mice (Jackson Laboratories, Bar Harbor, Me.) weighing 22-28 g were fed standard laboratory chow and given free access to water. CnAβ−/− mice were of the B6129J/F1 strain[13]. Age-, sex-, and strain-matched control mice were used as wild-type (WT) controls. All animal experiments were performed using a protocol approved by the University of Pittsburgh Institutional Animal Care and Use Committee.

Intra-ductal RC infusion in mice. The procedure for retrograde infusion into the CBD and pancreatic duct has been described before[14]. Briefly, Swiss Webster mice were anesthetized with isoflurane. A midline incision was made to reveal the abdominal cavity. The duodenum was flipped to reveal its distal side and held in place by ligatures. A 30 G needle was inserted through the anti-mesenteric aspect of the duodenum to cannulate the CBD. A small bull dog clamp was applied to the distal CBD (near the duodenum) to prevent back flow of the infusate into the duodenal lumen and to hold the cannula in place. A larger bull dog clamp was applied to the proximal CBD (near the liver) to prevent infusion into the liver and thus to direct flow to the pancreatic duct. Total volumes of 50-100 μl of iohexol, iopamidol, or normal saline (NS) were infused at 10-20 μl per min for 5 min using a P33 perfusion pump (Harvard Apparatus, Holliston, Mass.). Upon completion of the infusion, the bull dog clamps were released. The exterior abdominal wound was closed using 7 mm wound clips, and a single injection of buprenorphine (0.075 mg/kg) was given immediately after the surgery. Mice recovered on a heating pad for 30 min after the procedure. They were given free access to food and water after the surgery.

Detection and analysis of cellular $Ca^{2+}$ signals from mouse and human acini. Acinar cells were loaded at room temperature with the high-affinity $Ca^{2+}$-sensing dye Fluo-4AM ($K_d$=300 nM; Invitrogen). Acinar cells were plated on acid-washed glass coverslips and then mounted on a perifusion chamber. Thereupon, they were stimulated at room temperature with varying concentrations of RC (17-50%) diluted in HEPES buffer. Carbachol (1 mM) was given at the end of each experiment to confirm that the cells were intact and could mobilize intracellular $Ca^{2+}$ stores. A Zeiss LSM710 laser scanning confocal microscope was used with a 20×, 1.4 numerical aperture objective. The dye was excited at 488 nm wavelength, and emission signals of >515 nm were collected every 2 sec. Fluorescence from individual acinar cells was recorded. Analysis of recordings was performed using ImageJ software (NIH, Bethesda, Md.), and mean fluorescence over time in each region was graphed.

NFAT-luciferase activity assay. Acinar cells were infected with Ad-NFAT-luciferase following a previously described procedure[10,15,16]. The construct includes a luciferase gene placed downstream of an IL-4 promoter which contains nine tandem NFAT binding sites[10]. Acinar cells were incubated with the NFAT-driven luciferase adenovirus for 1.5 hr prior to stimulation. All of the stated inhibitors were added for 30 min prior to stimulation with RC. NFAT-luciferase was measured using the luciferase assay system. Briefly, cells were spun at 1,000 rpm for 5 min, washed with PBS, and lysed using reporter lysis 5× buffer (Promega #E397A, Madison, Wis.). Samples were vortexed and spun at 12,000 g for 2 min. Supernatant was plated, and luminescence was measured using a Synergy H1 plate reader (BioTek, Winooski, Vt.) and normalized to total protein.

NF-κB-luciferase activity assay. AR42J cells were differentiated towards an acinar phenotype by administering dexamethasone (100 nM) for 48-72 hr[17]. AR42J cells were infected with Ad-NF-κB luciferase 16 h prior to stimulation using a previously described method[12]. Following a wash with DMEM/F12 medium, acinar cells were evenly distributed in a 48-well plate and incubated for 30 min at 37° C. They were incubated with RC at varying concentrations and times. NF-κB-luciferase was measured using a commercially available luciferase assay (Promega, Madison, Wis.). Briefly, cells were spun at 1,000 rpm for 5 min, washed with PBS, and lysed using reporter lysis 5× buffer (Promega, catalog no. E397A). Samples were vortexed and spun at 12,000×g for 2 min. The supernatant was plated, and luminescence was measured using a Synergy H1 plate reader (BioTek, Winooski, Vt.) and normalized to total DNA.

Imaging pancreatic NF-κB bioluminescence in vivo. An AAV6-NF-κB-luciferase reporter was constructed, expanded in HEK293 cells, and purified as previously described[18-20,39]. A volume of 100 μl of virus ($10^{12}$ GCP/ml) was infused into the pancreaticobiliary duct at a rate of 10 μl/min using the same technique of RC infusion described above and recently published[21,39]. After a 5-week recovery from the surgery, mice underwent PEP induction with or without FK506 treatment. At varying time points after the surgery, ranging from 2 to 36 hr, bioluminescence signals were obtained by first giving a subcutaneous injection of luciferin (150 μg/g body weight) in the scruff of the neck 15 min before the start of imaging. The mice were briefly anesthetized with isoflurane and placed in the supine position in a bioluminescent imaging chamber (IVIS spectrum imager; Perkin Elmer, Waltham, Mass.) for 3-10 min. Average pixel intensity was measured from a pancreatic region of interest (in the upper abdomen). Raw time points from each mouse were normalized to its individual baseline intensity at time zero.

Pancreas tissue preparation, histological grading, and serum amylase. The pancreas, duodenum, and spleen were fixed at room temperature for 24 hr in 4% paraformaldehyde. Paraffin-embedded sections were stained with hematoxylin an eosin (HE) and graded using a 20× objective over 10 separate fields in a blinded fashion. Pancreas tissue was graded for edema, inflammatory infiltrate, and necrosis as described by Wildi et al.[67]. Whole blood samples were centrifuged at 1500×g for 5 min at 4° C. Serum amylase was measured using a Phadebas kit (Amersham Pharmacia, Rochester N.Y.) as previously described[68].

Preparation of mouse pancreatic acini for $Ca^{2+}$ imaging. Groups of pancreatic acinar cells were isolated as previously described[26,69], with minor modifications. Briefly, the pancreas was removed, and then minced for 5 min in buffer containing 20 mM HEPES (pH 7.4), 95 mM NaCl, 4.7 mM KCl, 0.6 mM $MgCl_2$, 1.3 mM $CaCl_2$=, 10 mM glucose, and 2 mM glutamine, plus 1% BSA, 1×MEM nonessential amino acids (GIBCO/BRL), 200 units/ml type-4 collagenase (Worthington, Freehold, N.J.), and 1 mg/ml soybean trypsin inhibitor. The tissue was incubated for 30 min at 37° C. with shaking at 90 rpm. The digest was transferred to a 15 mL conical tube and washed with collagenase-free buffer. The suspension was vigorously shaken for 15-20 sec to separate the cells into smaller clusters.

Western blot for phospho-IκBα and p65 translocation. Mouse pancreatic acini were isolated using 2 mg/ml collagenase in F12/DMEM medium plus 1% sodium pyruvate and 1% BSA. After 3 washes, acinar cells were cultured in F12/DMEM medium plus 0.1% BSA. Cells were treated with RC and collected at varying time points. Cells were washed with 1×PBS and lysed in 1×SDS sample buffer. To examine nuclear translocation of p65, nuclear and cytosolic fractions were extracted using an NE-PER nuclear and cytoplasmic extraction kit (Thermo Scientific, Rockford, Ill.). Forty micrograms of protein were run on a 4-20% gradient PAGE gel. All antibodies were purchased from Cell Signaling (Beverly, Mass.). Phosphorylation of IκBα at Ser32 was examined by western blotting using a phospho-IκBα-specific antibody (#2859). Actin (#4967) was used as a loading control. Blots for p65 were performed on nuclear and cytosolic fractions using a Cell Signaling antibody (#4764). GAPDH (#2118) and histone 3 (#9715) were used as cytosolic and nuclear markers, respectively. Densitometry was performed using Image J software (NIH).

Cell necrosis assay. Acinar cells were incubated in a 48-well plate with 50 μg/ml of propidium iodide (PI) for 30 min prior to addition of RC. Fluorescence was measured at 536 nm excitation and 617 nm emission wavelengths over time a time course of up to 6 hr. Fluorescence was measured after cell lysis with 0.5% Triton-X 100 was used to normalize the results relative to total DNA.

ATP level measurements. Following isolation, pancreatic acinar cells were cultured in DMEM/F12 Medium (0.5 ml/well of a 48-well plate) at 37° C. water bath and treated with RC±FK506. Cells were collected at indicated time points and lysed in 100 μl lysis buffer (100 mM Tris pH 7.75, 4 mM EDTA). ATP levels were measured from 20 μl aliquots of acinar cell lysates using the ENLITEN luciferase/luciferin reagent (Promega catalog no. FF2021).

RNA extraction from whole pancreas and real-time PCR. Total RNA from the pancreatic head was obtained by homogenizing 40 mg of tissue in 2 ml of TRIzol reagent (Life Technologies; Grand Island N.Y.) at 4° C. and immediately flash frozen in liquid nitrogen. Samples were thawed on ice and centrifuged at 12,000×g for 10 min at 4° C. The supernatant was diluted with 200 μl of chloroform and centrifuged at 12,000×g for 15 min at 4° C. The upper aqueous phase was treated with 0.5 ml of isopropanol and centrifuged at 10,000×g for 10 min at 4° C. The pellet was resuspended with 150 μl of 75% ethanol and centrifuged at 7500×g for 5 min at 4° C. The pellet was air-dried and dissolved in 100 μl of nuclease-free water. Total RNA samples were used to generate cDNA using the iScript Advanced cDNA synthesis Kit (Bio Rad; Hercules, Calif.).

Quantitative real-time PCR (rtPCR) was performed to determine the relative expression of the cytokines IL-6 and IL-1β as well as the cell growth arrest and DNA-damage inducible gene GADD45B. The primer pairs for each as well as a GAPDH control were obtained as part of the PrimePCR-PreAMP SYBR Green Assay (Bio Rad; unique assay ID #qMmuCEP0054186, qMmuCID0005641, qMmuCEP0039581). rtPCR reactions were carried out in 20 μl volume reactions using the SsoAdvanced Universal Supermix SYBR Green system (Bio Rad). The reactions contained 1× SsoAdvanced Universal SYBR Green Supermix, 300 nM forward Primer, 300 nM reverse primer and 100 ng cDNA. rtPCR conditions were 95° C. for 10 sec and 60° C. for 30 sec for 35 cycles on a Bio Rad CFX96 Touch thermocycler (Bio Rad). Results for the expression of mRNA were normalized to expression of 18S rRNA and are represented relative to expression levels for each of the control groups.

Statistical analysis. Data were expressed as mean±standard deviation unless otherwise stated. Statistical significance was determined using an unpaired T-test and defined as a P value ≤0.05.

6.2. Results

Intraductal infusion of RC induces pancreatic injury in mice. A PEP model in mice was developed by performing a transduodenal cannulation of the CBD as detailed in the Methods (FIG. 1A). Infusions were channeled into the pancreatic duct by clamping the proximal CBD and thus preventing retrograde flow into the liver.

Figure 1B:
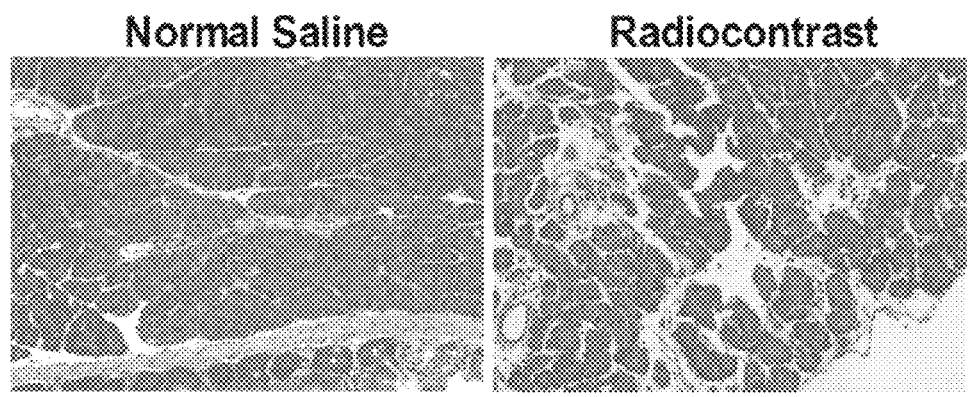
Figure 1B:
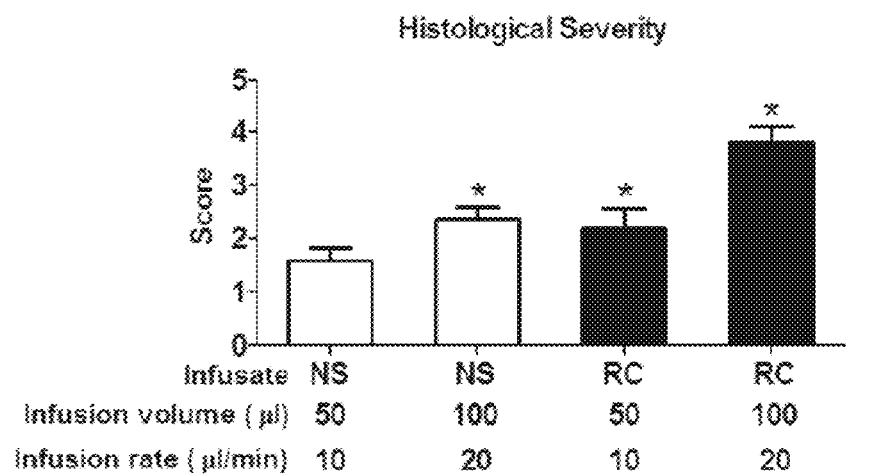
Figure 1B:
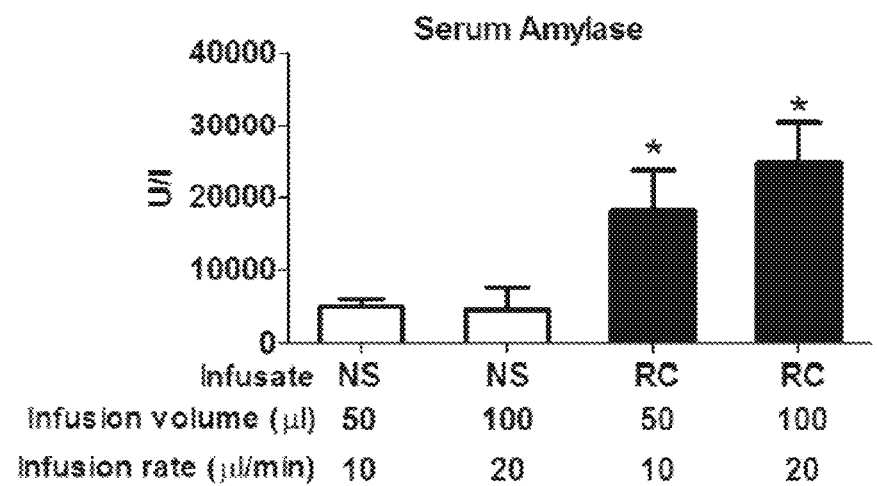
Figure 1C:
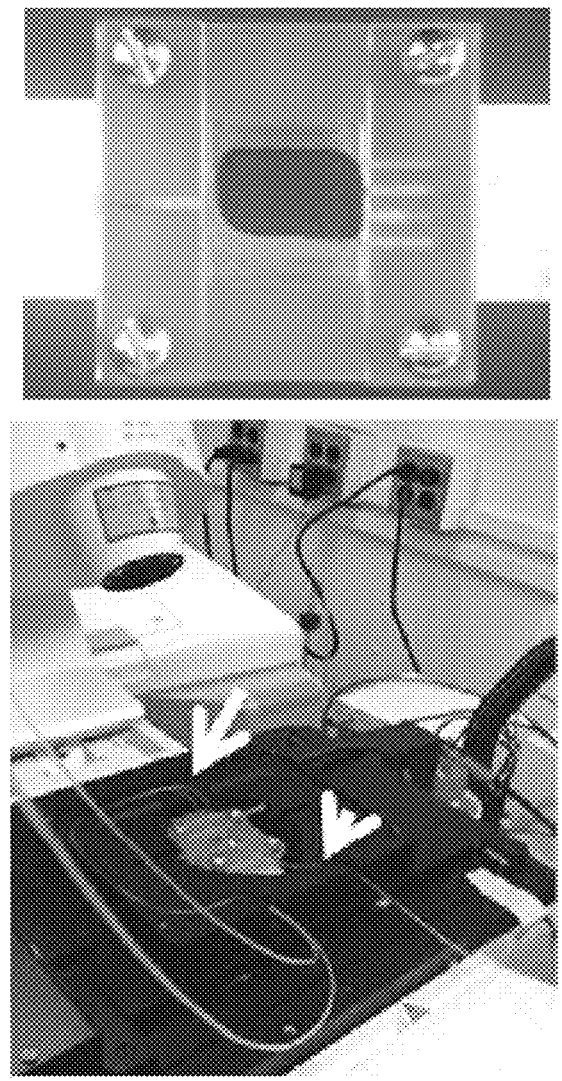
Figure 1D:
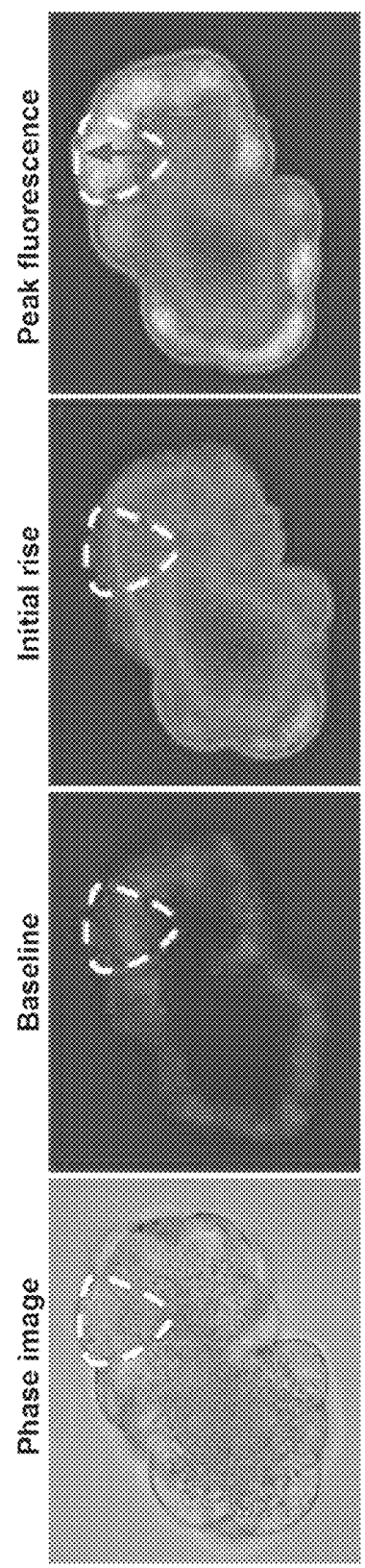
Figure 1E:
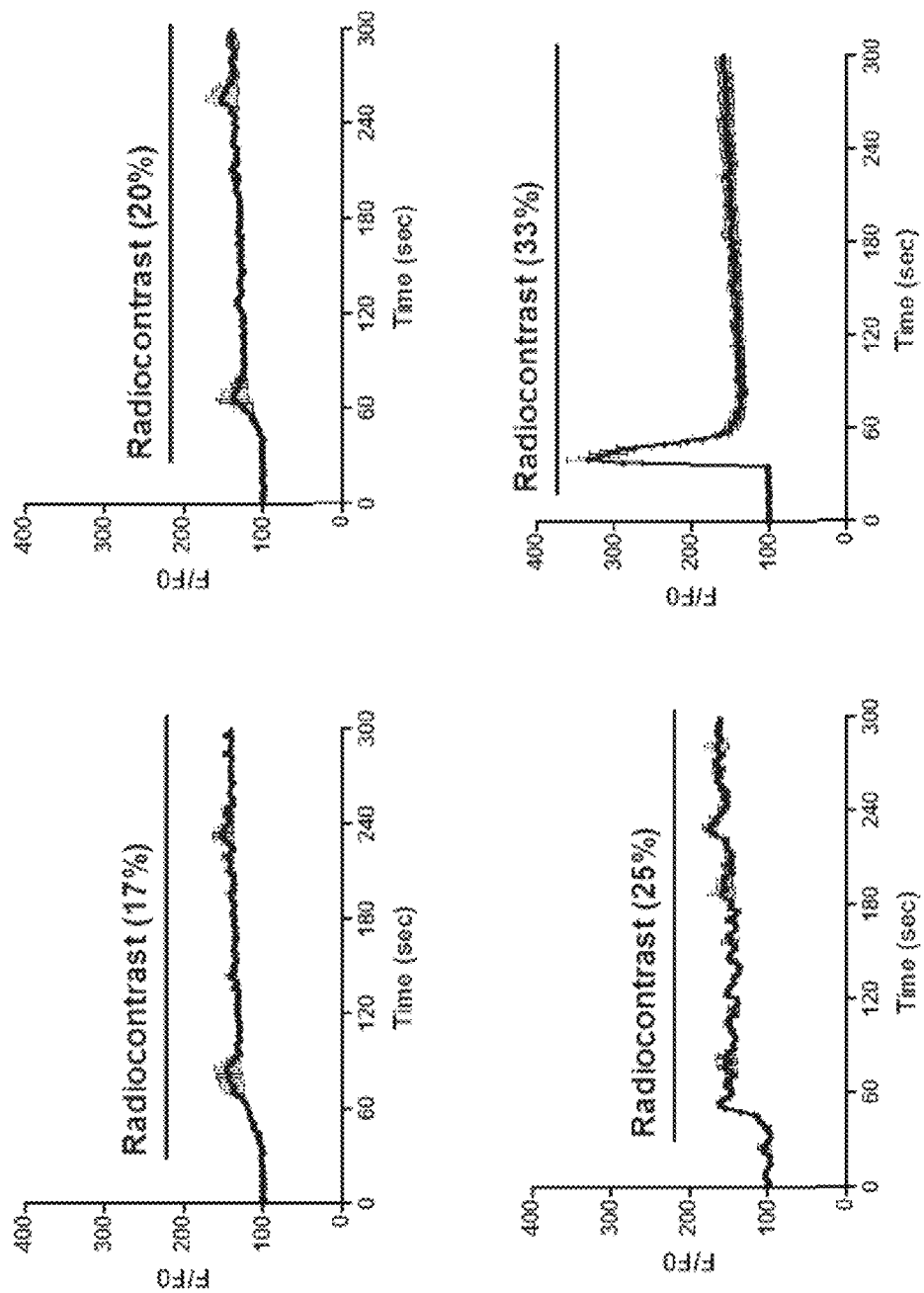
Figure 1F:
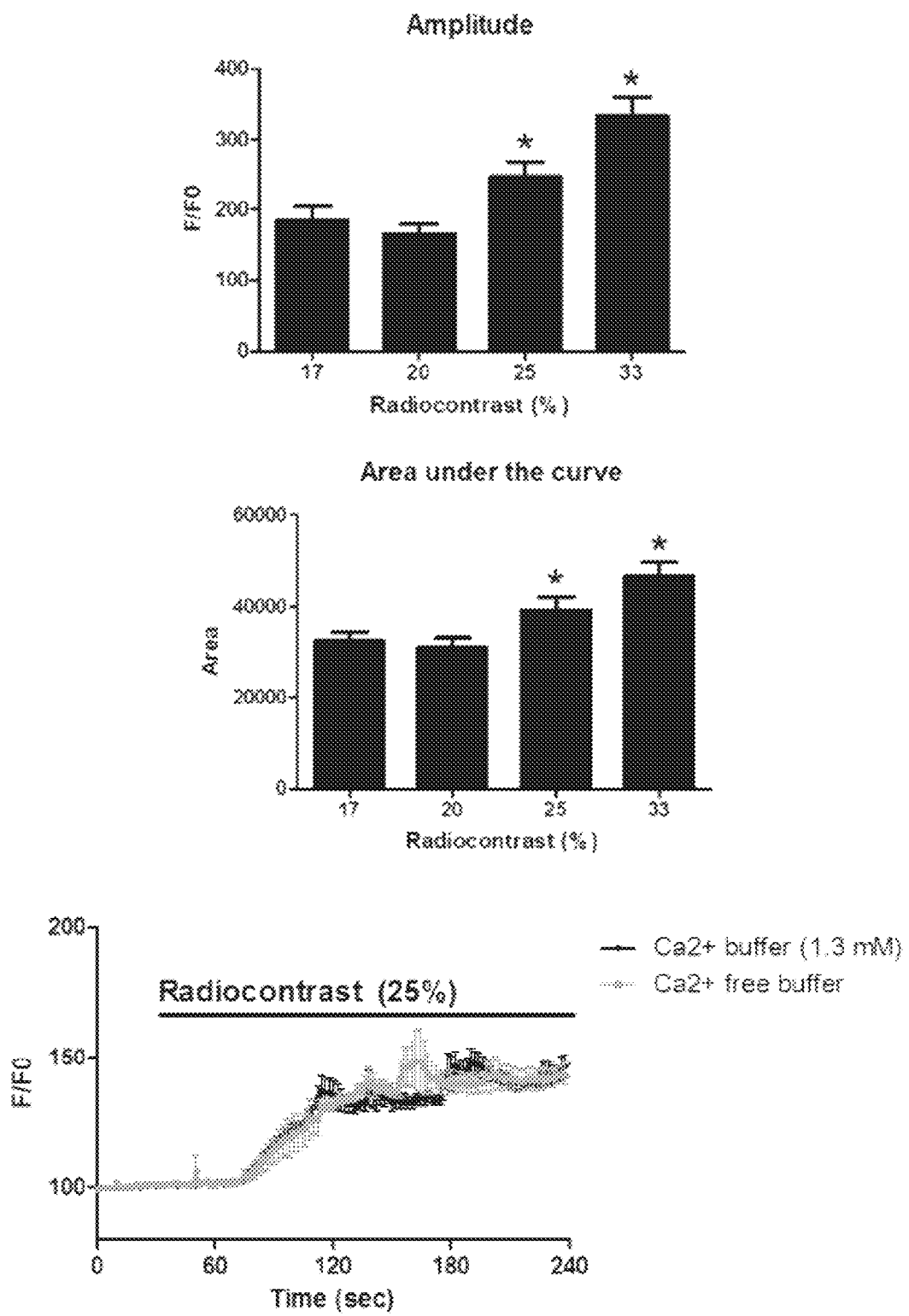
Figure 2A:
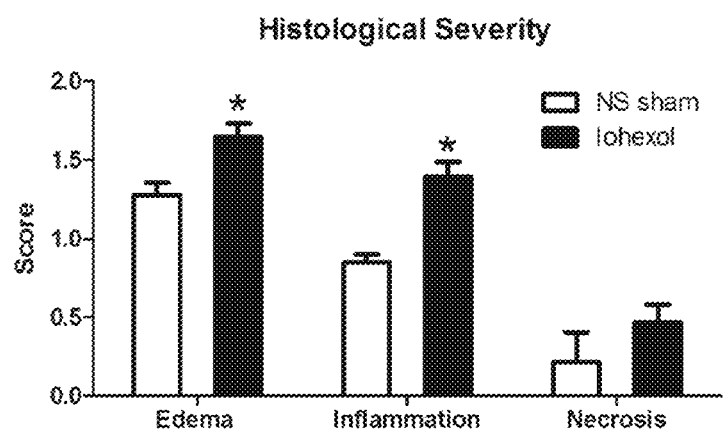
Figure 2B:
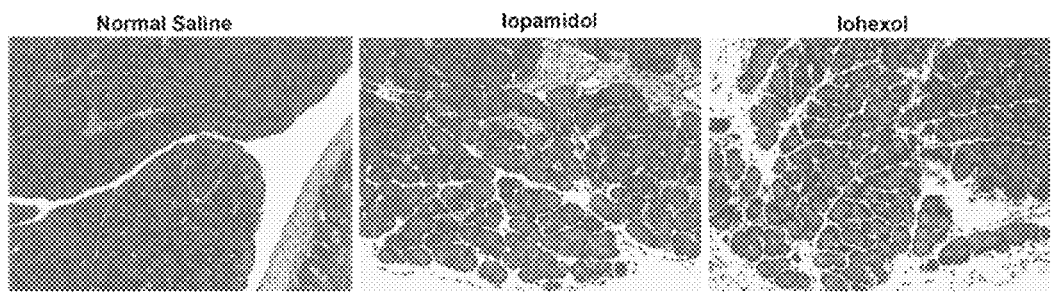
Figure 2C:
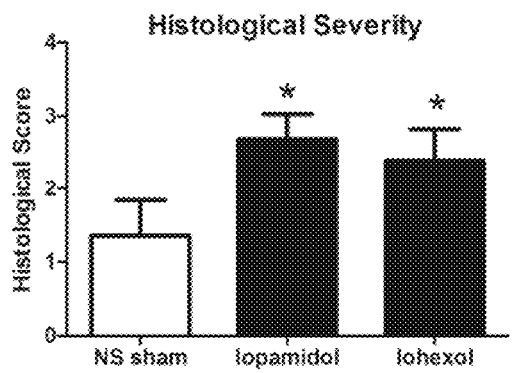
Figure 2D:
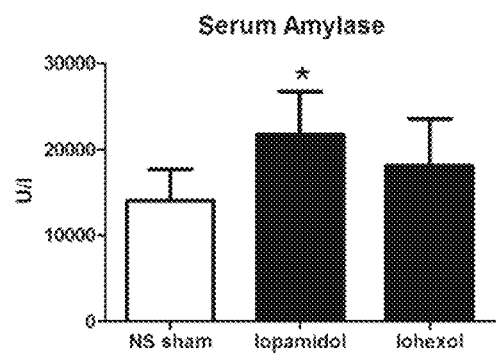
Figure 2E:
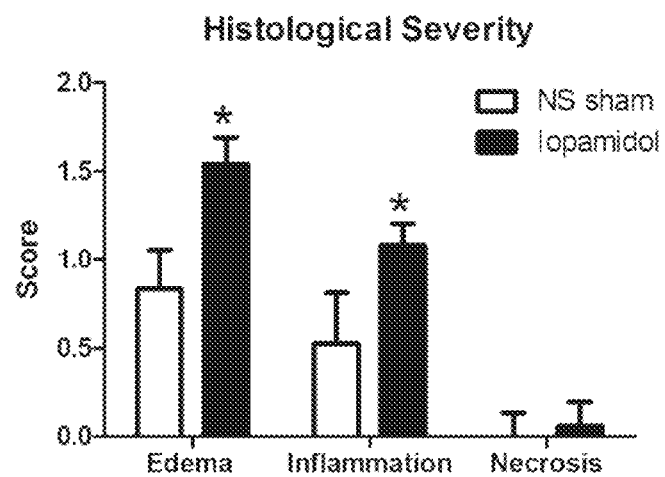
Figure 2F:
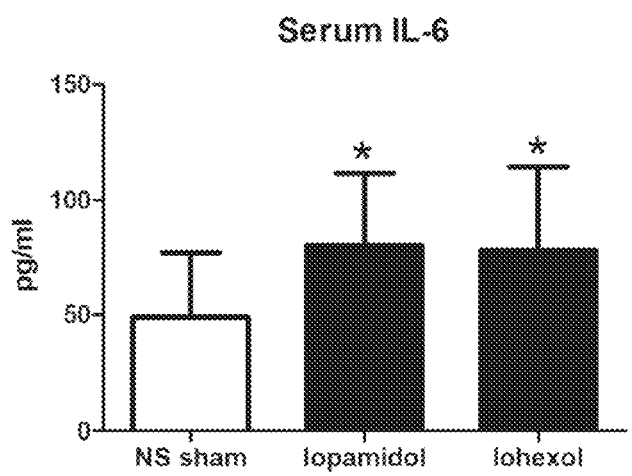

Histological severity of pancreatitis, graded by the presence of edema, inflammatory infiltrate, and necrosis was assessed from the head of the pancreas 24 hr after the surgical procedure (FIG. 1B and FIG. 2A). Serum amylase was measured 6 hr post-procedure.

Clinical reports have suggested that post-ERCP pancreatitis is due to a combination of pressure and contrast exposure to the pancreas[3]. Because the currently available constant pressure pumps could not infuse at low enough rates required for the biliopancreatic duct in mice (10-20 μl/min), changes in pressure were mimicked by varying the rate and volume of infusions.

Doubling the rate and volume of normal saline (NS) infusion increased histological severity by 33% (P<0.05), but it did not cause a rise in serum amylase, showing that pancreatitis did not reach a threshold level. Replacing the NS with RC, however, appeared to have an additive effect on histological severity, leading to a 59% increase above the intra-ductal NS sham control (P<0.05). Serum amylase increased by at least 50% and ranged among several batches of experiments between a 1.5- to 3.5-fold increase. Based on these findings, both increased pressure and RC exposure contribute to injury in the PEP model.

Acidic contrast has been shown to mediate severity of pancreatitis in rats[22]. When RC was buffered with 10 mM HEPES and the pH was clamped at 6, however, in mice there was no increased severity of pancreatitis compared to a pH of 7. Most of the experiments were performed using iohexol (Omnipaque 300) which is a commonly used RC in ERCP[23]. The findings were similar, however, with iopamidol (Isovue 300), which is another low osmolality, non-ionic, iodinated RC (FIGS. 2B-2F).

RC induces high amplitude $Ca^{2+}$ signals in mouse pancreatic acinar cells. RC exposure is a major contributor to PEP, therefore the mechanism by which RC initiates pancreatitis ex vivo in isolated pancreatic cells was examined. Although duct cells line the pancreatic duct and ductules, over 85% of the pancreas is comprised of pancreatic acinar cells[24]. Pancreatitis initiates within the acinar cell, and one of the earliest, critical factors in most experimental models is the induction of large-amplitude, peak-plateau (or sustained) $Ca^{2+}$ signals[25-27]. To test whether RC induces acinar cell $Ca^{2+}$ signals, small clusters of 5 to 15 primary acinar cells, grouped as acini, were freshly isolated. They were loaded with the high affinity $Ca^{2+}$-dye Fluo-4AM and imaged in a perifusion chamber using time lapse confocal imaging (FIGS. 1C-1F). During ERCP, even with a dedicated pancreatography that deliberately instills RC into the pancreatic duct, we estimated that the acinar lumen is exposed to RC concentrations ranging from 10% to 50% because of considerable dilution from pancreatic juice. For this reason, acini were perfused with the above dilutions of RC.

Concentrations of 17% to 20% RC elicited low-amplitude $Ca^{2+}$ transients within 100 sec that immediately returned to baseline. As the RC was increased to 25% and then 33%, there were peak-plateau $Ca^{2+}$ waves which propagated from the apical to basolateral region of most cells. These signals were characterized by a high amplitude (400% above baseline), followed by a sustained plateau. The $Ca^{2+}$ signal initiated in the same way even in $Ca^{2+}$-free media, showing that RC first triggers $Ca^{2+}$ release from intracellular stores.

Figure 3A:
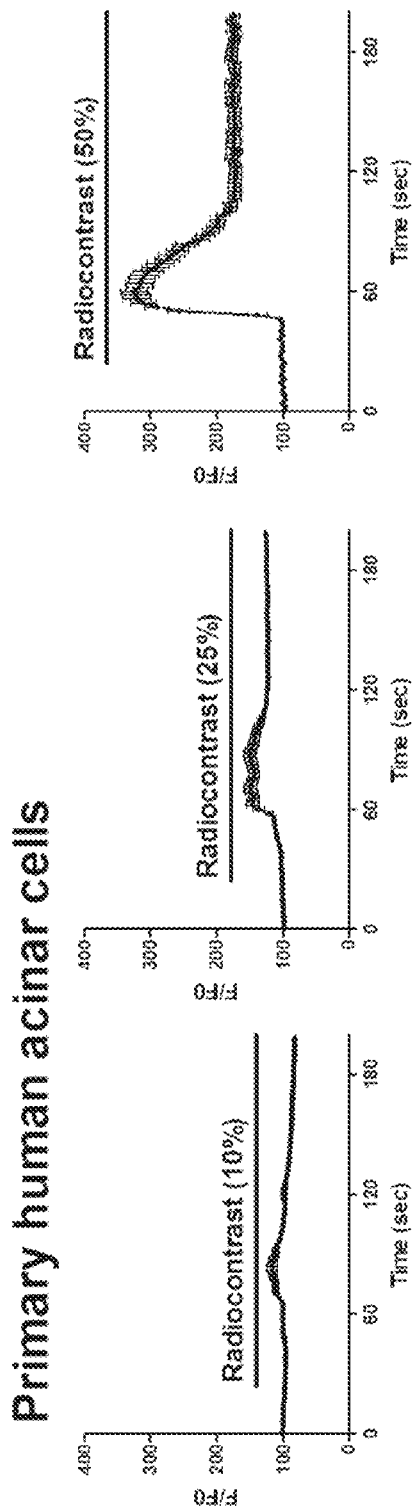
Figure 3B:
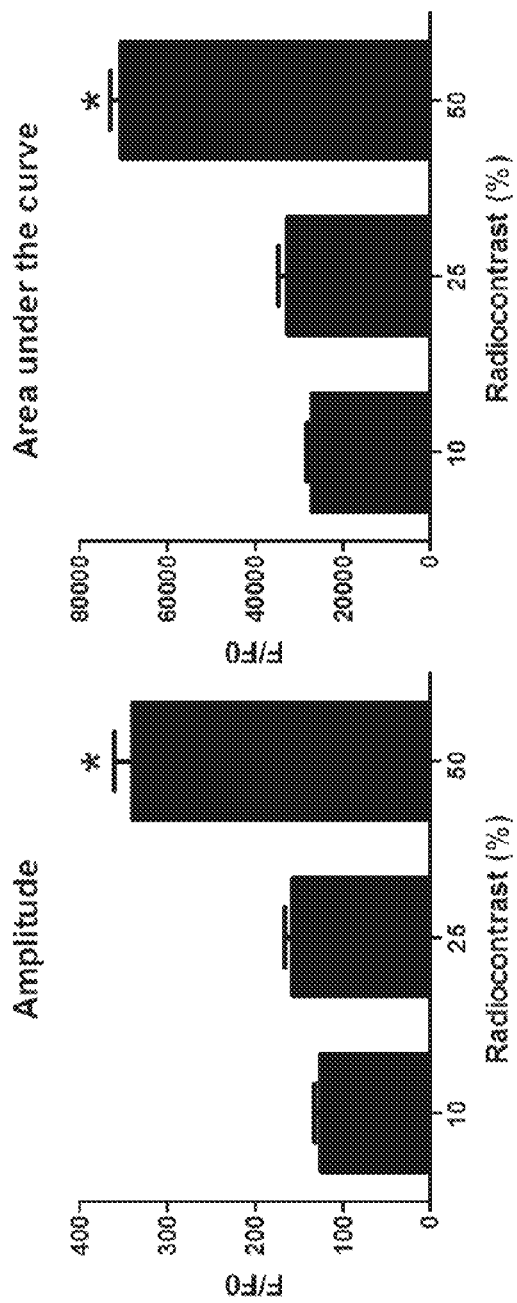
Figure 3C:
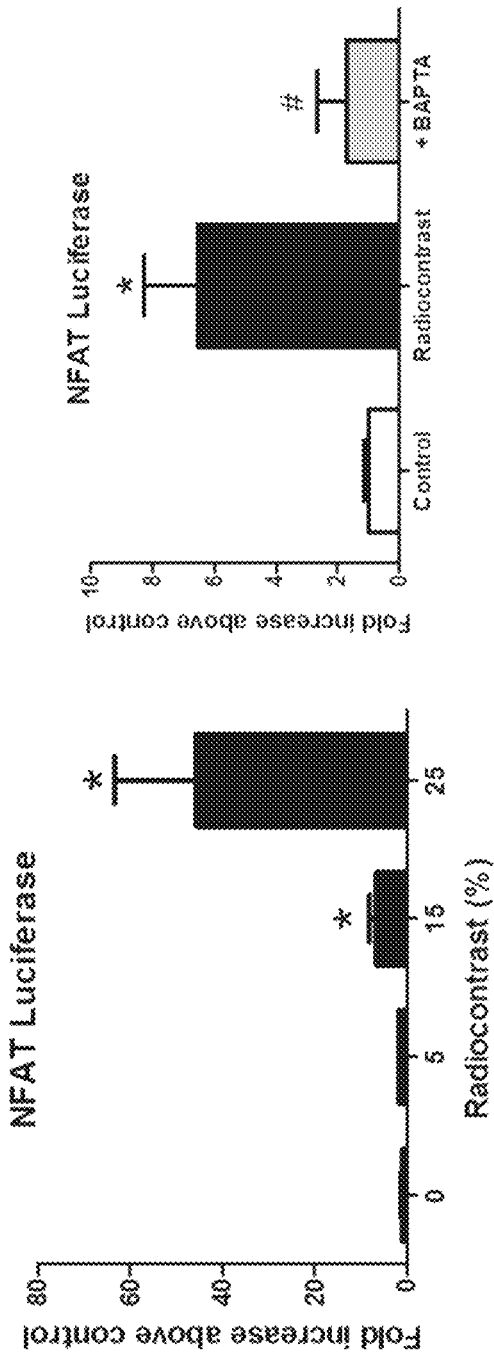
Figure 3D:
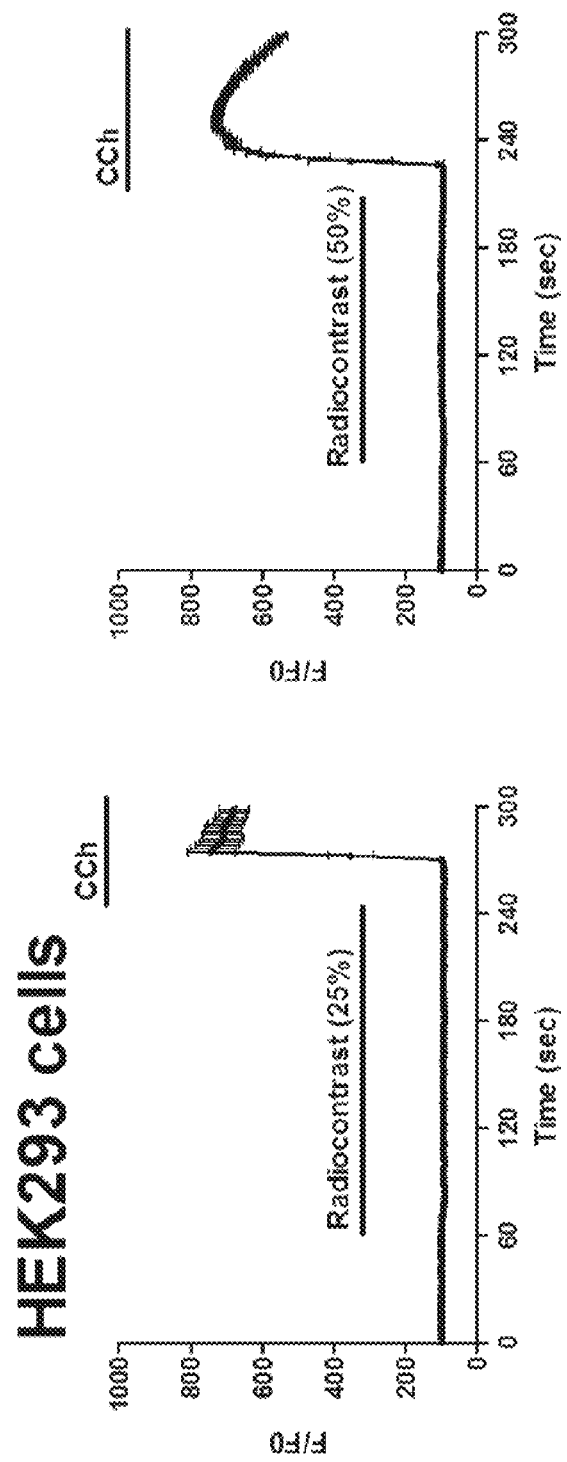
Figure 3E:
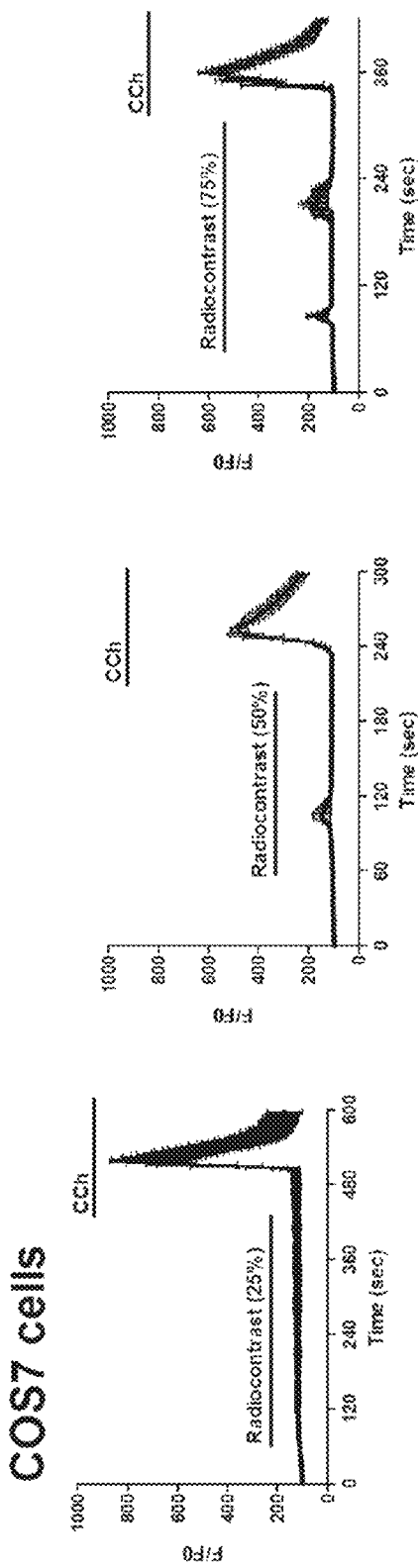
Figure 4A:
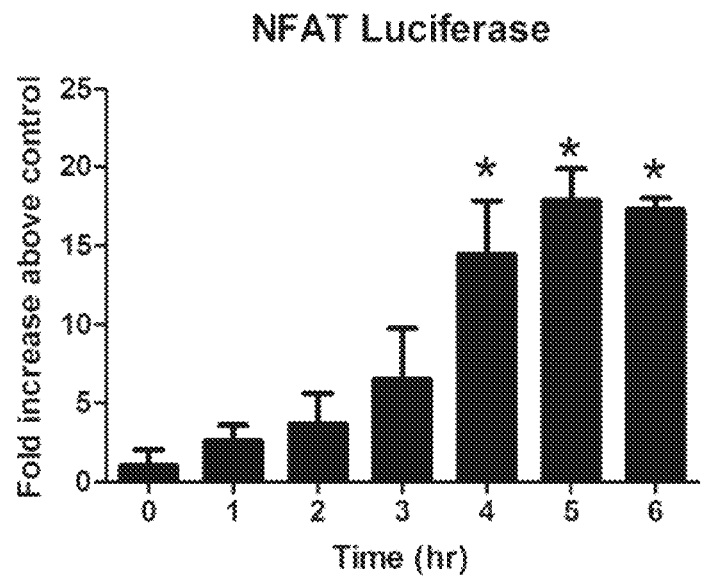
Figure 4B:
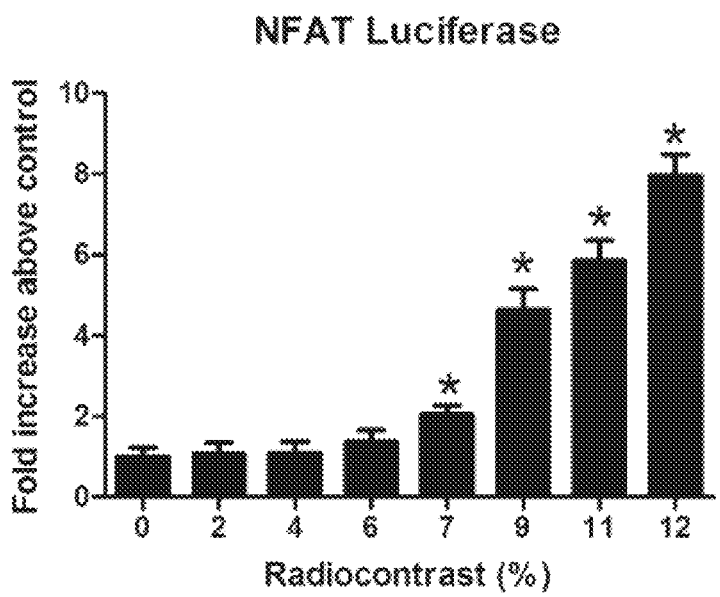
Figure 4C:
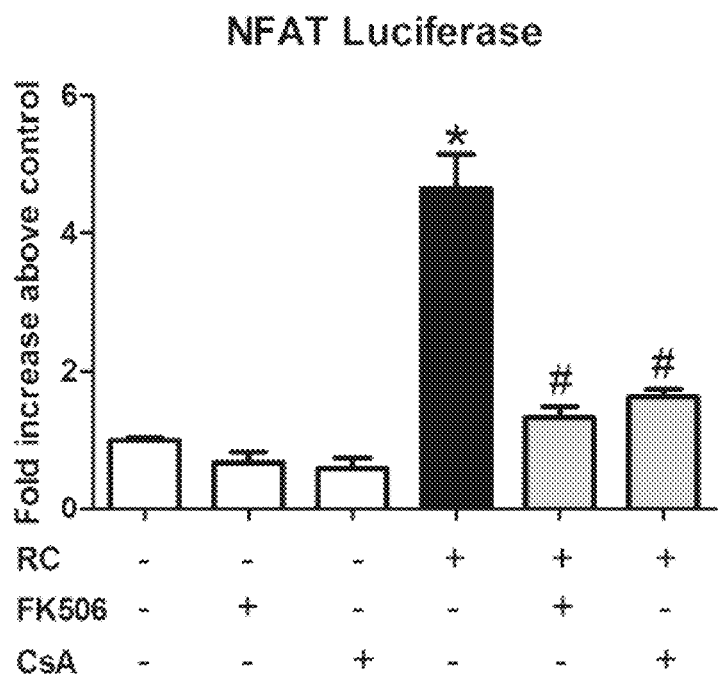
Figure 4D:
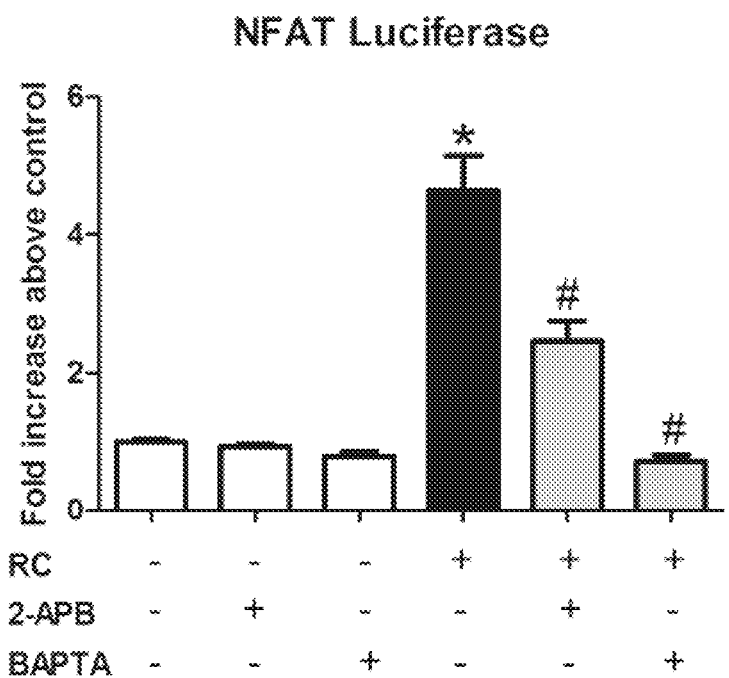

All of these experiments were followed 5 min later by perfusion with the muscarinic agonist carbachol (1 mM) in order to confirm the ability of the cells to mobilize $Ca^{2+}$. RC also induced $Ca^{2+}$ signals and calcineurin activation in live human acinar cells procured from cadaveric donors (FIGS. 3A-3C). The robust $Ca^{2+}$ signals seen in pancreatic acinar cells were not observed in the HEK293 or COS7 cell lines, showing a certain level of selectivity of RC-induced $Ca^{2+}$ signals for acinar cells (FIGS. 3D-3E).

RC induces acinar cell calcineurin activation. Since RC induces $Ca^{2+}$ signals, the present example examined whether calcineurin, a putative $Ca^{2+}$ target in pancreatitis, was activated. To examine calcineurin activation, the adenoviral NFAT (nuclear factor of activated T-cells)-luciferase was used, which consists of 9 tandem NFAT binding motifs from the IL-4 promoter[10]. Calcineurin dephosphorylation of NFAT in the cytoplasm causes translocation to the nucleus and thereby drives luciferase.

In primary acinar cells, RC caused a concentration-dependent increase in NFAT-luciferase, and the increases were due to calcineurin activation because the calcineurin inhibitors FK506 (24 μM) and cyclosporine (CsA; 16 μM) largely prevented the rise due to the RC (FIG. 4). Calcineurin activation with RC was partially dependent on inositol 1,4,5-trisphosphate receptor (IP3R) activation, since 2-APB (100 μM) reduced the luciferase rise by 47% (P<0.05). However, calcineurin activation was completely reduced by BAPTA-AM (64 μM). The RC iopamidol also induced NFAT activation in a concentration-dependent manner (FIG. 5). These data demonstrate that RC induces calcineurin activation in acinar cells through a rise in cytosolic $Ca^{2+}$.

Figure 6B:
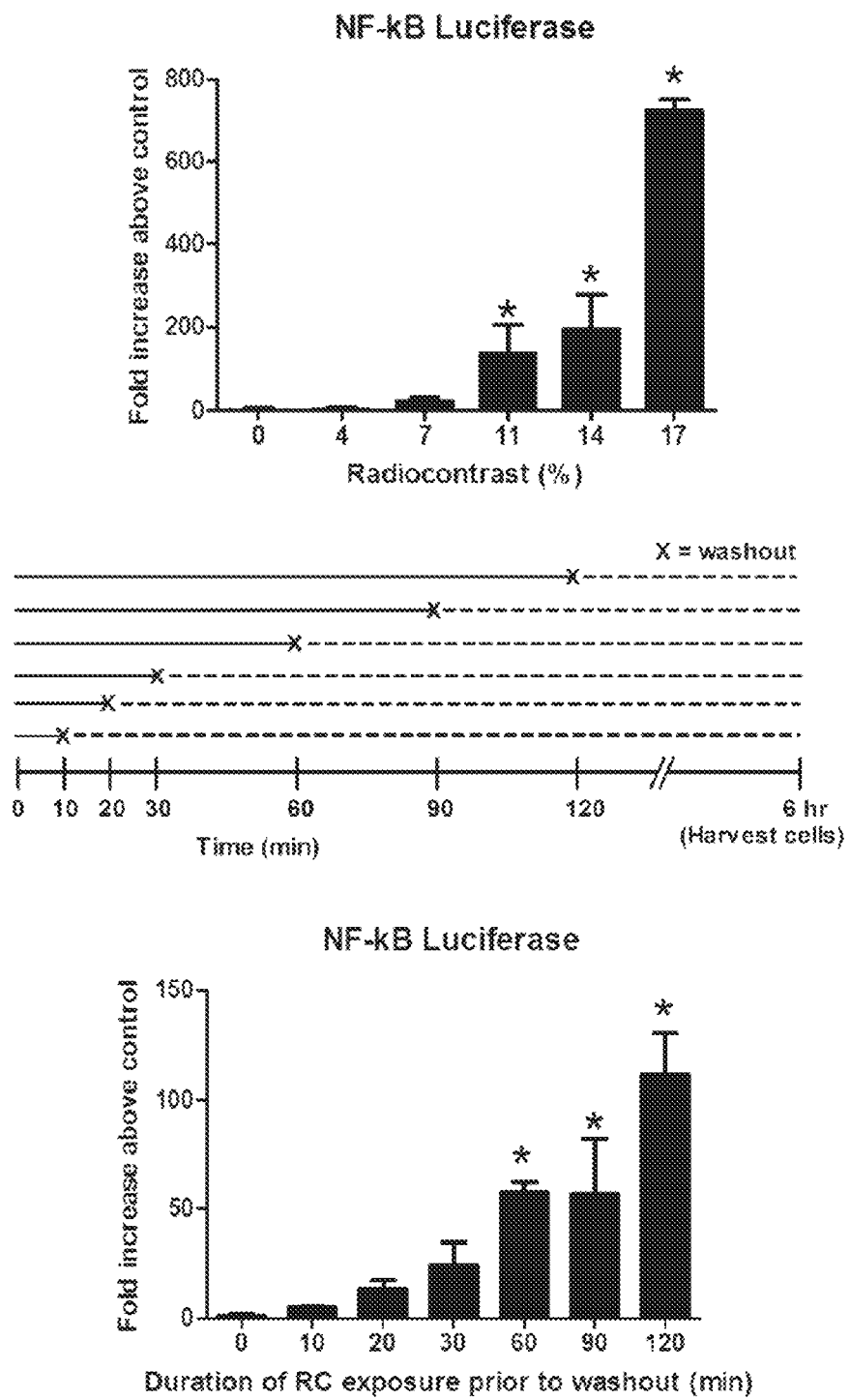
Figure 8A:
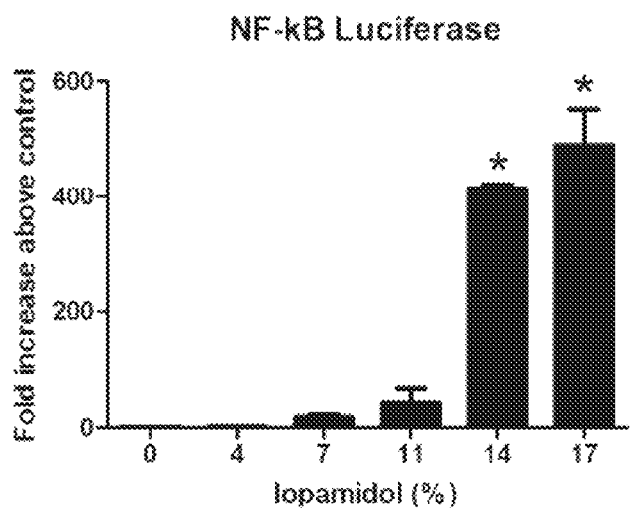

RC causes NF-κB activation through a $Ca^{2+}$/calcineurin dependent pathway. A master regulator of inflammation in pancreatitis is the transcription factor NF-κB, which can induce several inflammatory genes including IL-6, Spi2a, TGF-β, and IL-1β[28-31]. In primary acinar cells, increasing concentrations of RC induced phosphorylation of IκBα at Serine 32 (which is an early degradation signal[32]) and nuclear translocation of p65 (FIG. 6A). To determine whether RC induces NF-κB in a reporter system, we used the adenoviral NF-κB luciferase, which requires an overnight infection followed by 6-8 hr administration of RC[12]. Due to the limitations of using primary acinar cells in long term culture for this assay, we turned to the AR42J pancreatic cell line, which when primed with dexamethasone (100 nM) for 48-72 hr induces an acinar cell phenotype[17]. RC induced $Ca^{2+}$ signals and calcineurin was activated in this cell line, as well as in the primary acinar cells (FIG. 7). RC caused a concentration- and time-dependent increase in NF-κB-luciferase (FIG. 6B). Even brief exposure of RC (i.e. 25% given for 10 min, followed by a washout) which more closely mimics exposure conditions during ERCP, led to a 5-fold increase in NF-κB luciferase above baseline. Statistically significant increases were, however, observed 60, 90, and 120 min, resulting in a 58-, 59-, and 112-fold increase above baseline, respectively (P<0.05). The RC iopamidol also induced NF-κB activation in a concentration-dependent manner (FIG. 8A).

Figure 6C:
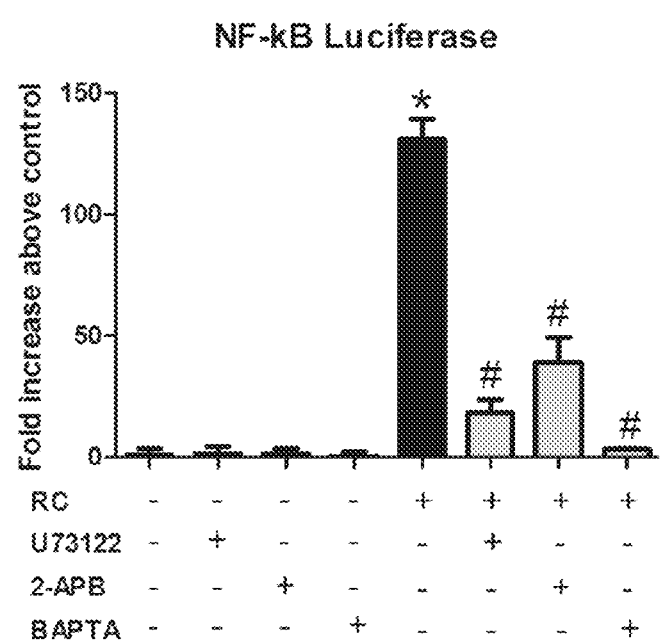
Figure 6D:
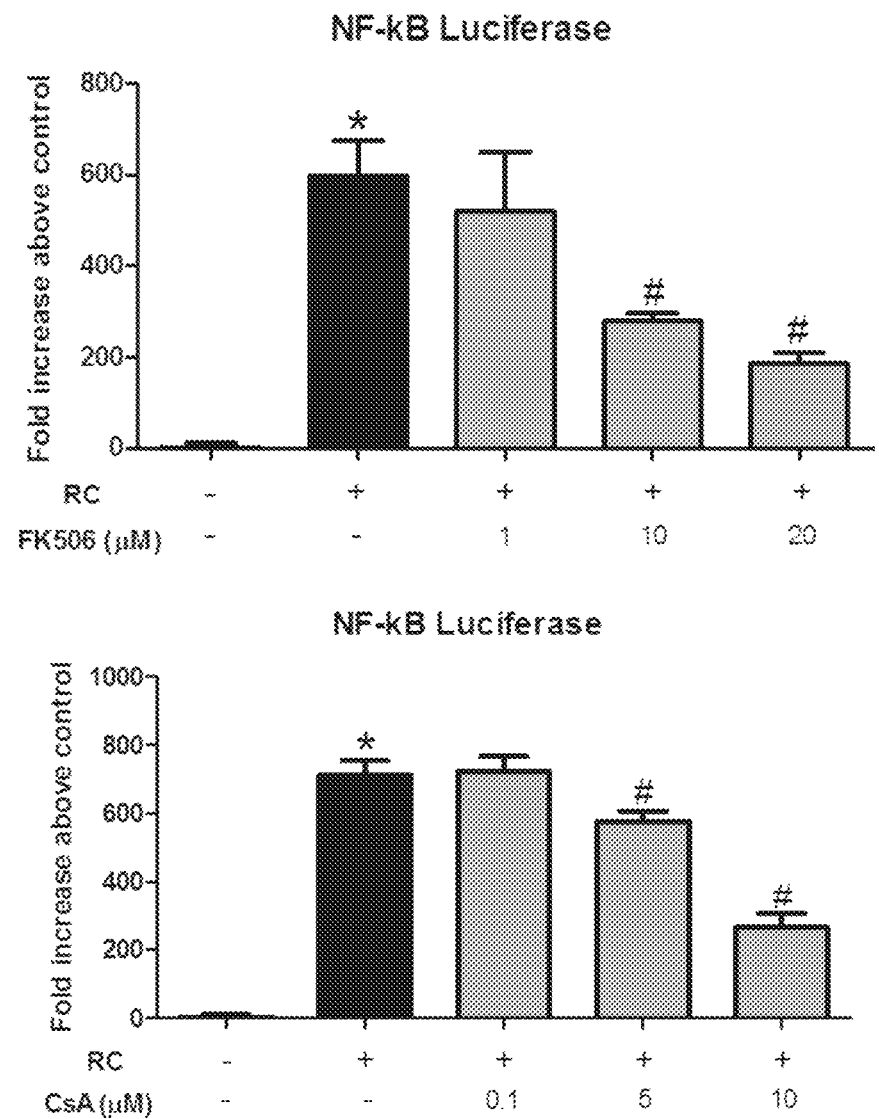

NF-κB activation due to RC was dependent on phospholipase C (PLC), IP3Rs, and cytosolic $Ca^{2+}$, since luciferase levels were reduced by their respective inhibitors U73122 (5 μM), 2-APB (100 μM), and BAPTA (64 μM; FIG. 6C). A key finding was that the calcineurin inhibitors FK506 (24 μM) and CsA (16 μM) reduced NF-κB by 73% and 79%, respectively (P<0.05; FIG. 6D). Taken together, RC causes NF-κB activation through a $Ca^{2+}$- and calcineurin-dependent pathway.

The formulation of iohexol used (Omnipaque 300) has an osmolality of 672 mOsm/kg at full strength, which categorizes it as a low osmolality contrast medium[23] (Table 1).

TABLE 1

Comparison of calculated osmolarity of iohexol with osmometer measurements for the concentrations used in this example.

| Radiocontrast (%) | Calculated (mOsm/kg) | Measured (mOsm/kg) |
|---|---|---|
| 0 | 330 | 330 |
| 5 | 347 | 356 |
| 10 | 364 | 396 |
| 15 | 381 | 409 |
| 25 | 416 | 459 |

Figure 8B:
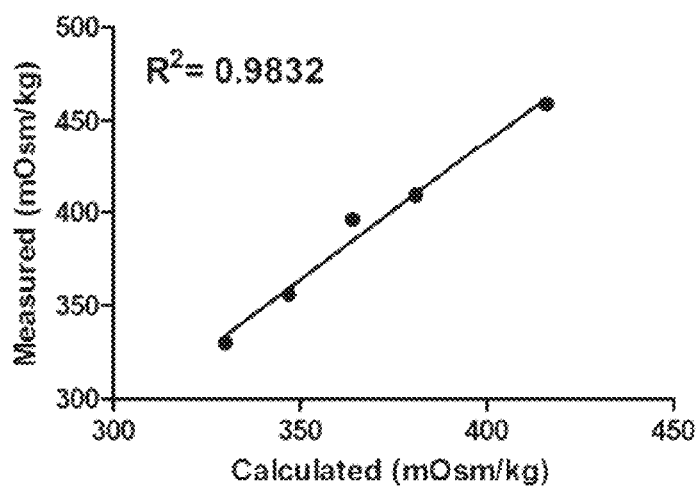
Figure 8C:
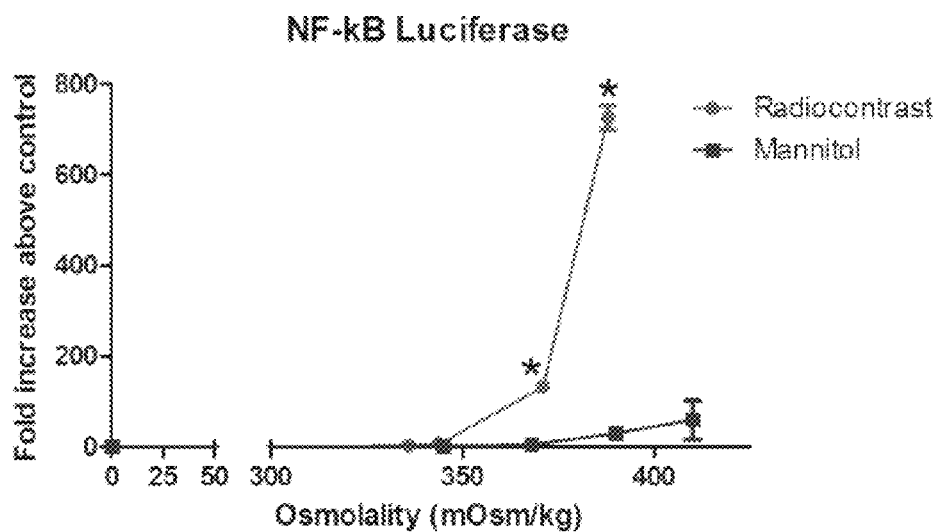
Figure 8D:
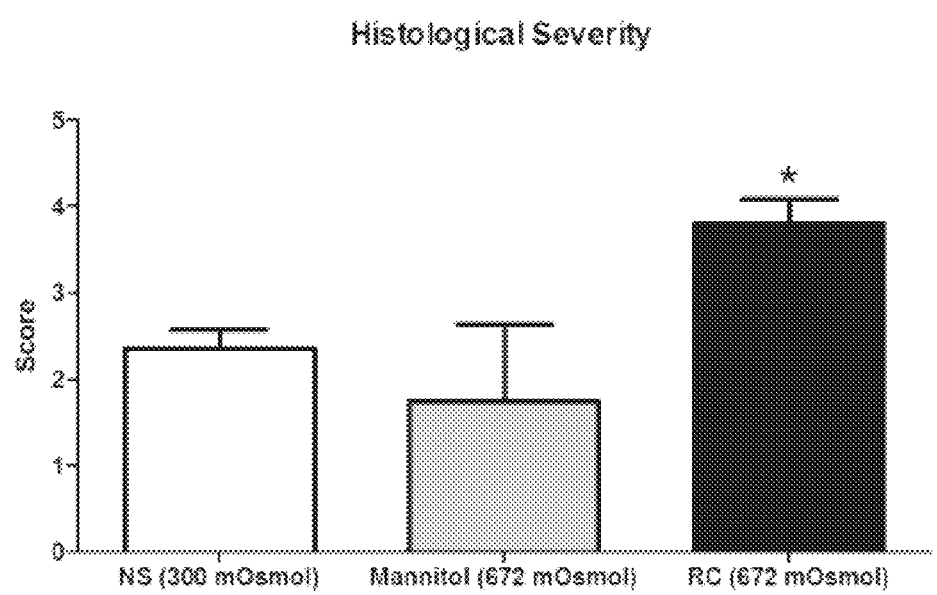
Figure 8E:
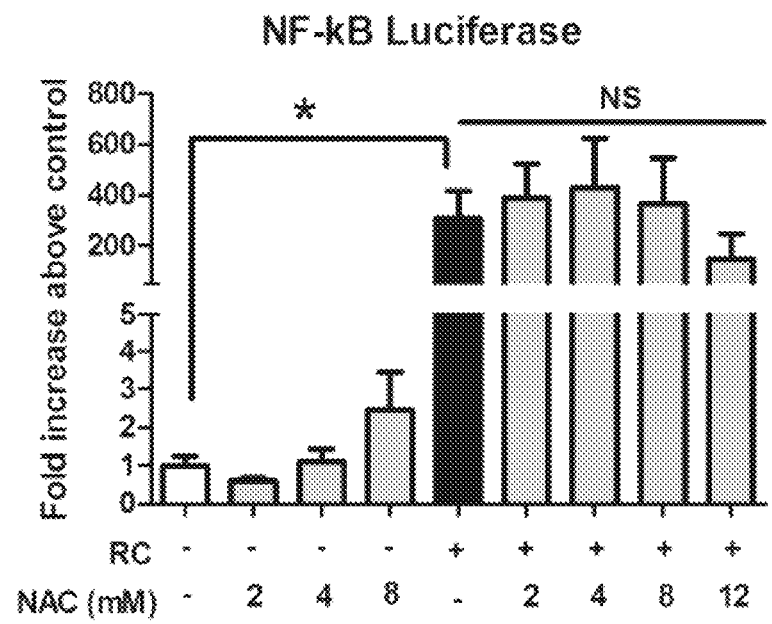
Figure 8F:
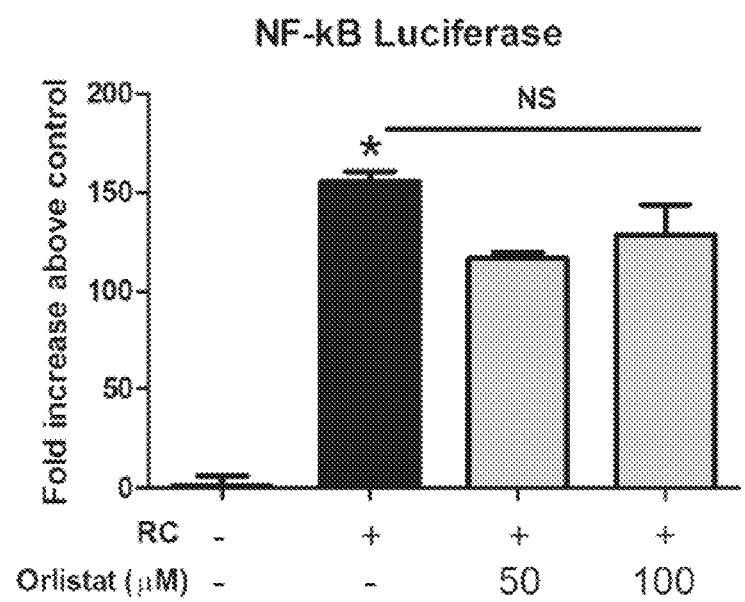

A metanalysis of a dozen randomized, controlled studies failed to demonstrate a significant difference between low or high osmolality RCs in inducing clinical PEP[33]. Nonetheless, the contribution, if any, of osmolality on NF-κB activation using mannitol was examined (FIGS. 8B-8C). Whereas RC induced a 300-fold rise in NF-κB at 350 mOsm/L, equimolar concentrations of mannitol failed to cause an increase. There are conflicting data about the role of oxidative stress in mediating RC nephropathy[34,35]. However, in the acinar cell line, pretreatment with the reactive oxygen species (ROS) scavenger N-acetylcysteine (NAC; 2-12 mM) had no effect on NF-κB activation (FIG. 5D). Another factor to consider, based on recent reports[36,37], is whether the RC might contain a triglyceride lipid emulsion, that can be liberated into toxic non-esterified fatty acids by exposure to lipases in pancreatic secretions during the ERCP (FIG. 8E). The RC manufacturer, however, denied adding any emulsions. Further, pretreatment with the lipase inhibitor Orlistat did not significantly reduce the activation of NF-κB with RC. The results show that RC-induced NF-κB activation is independent of osmolality, oxidative stress, or fatty acid toxicity.

Figure 6E:
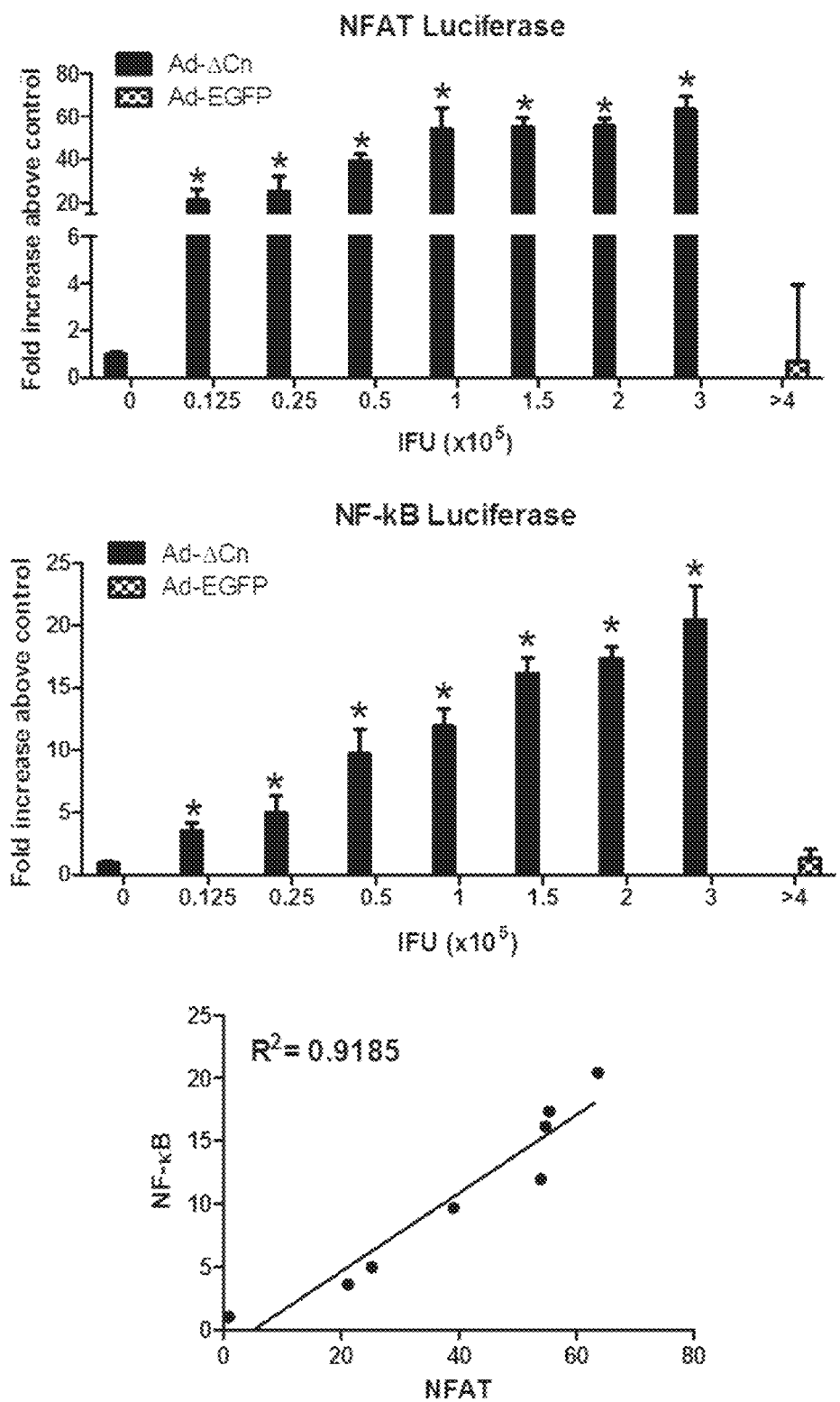
Figure 7A:
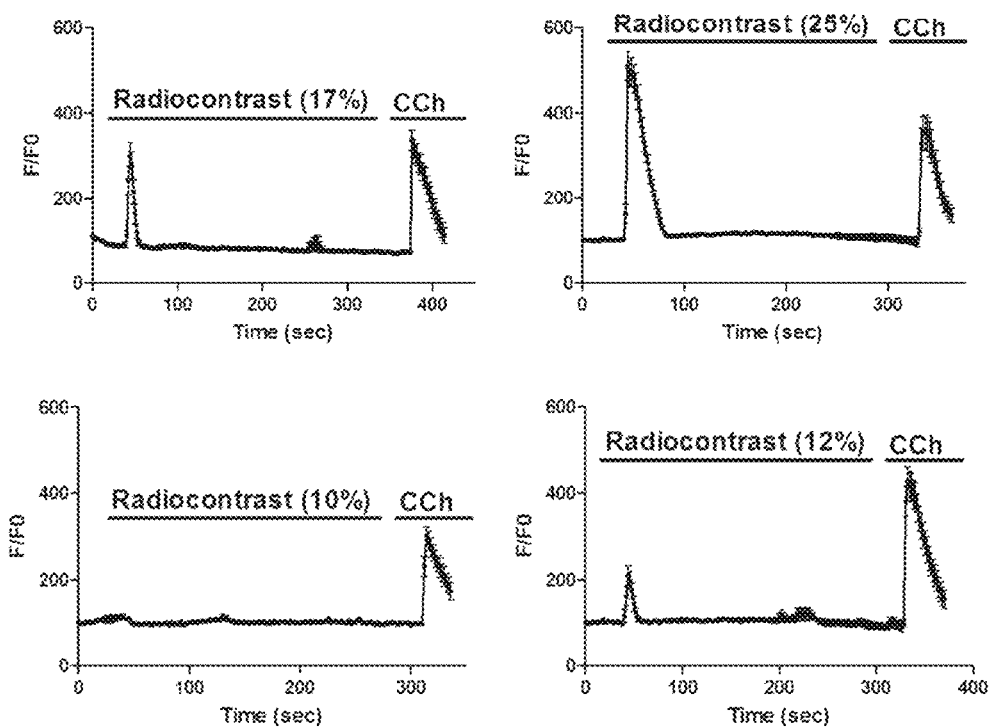
Figure 7B:
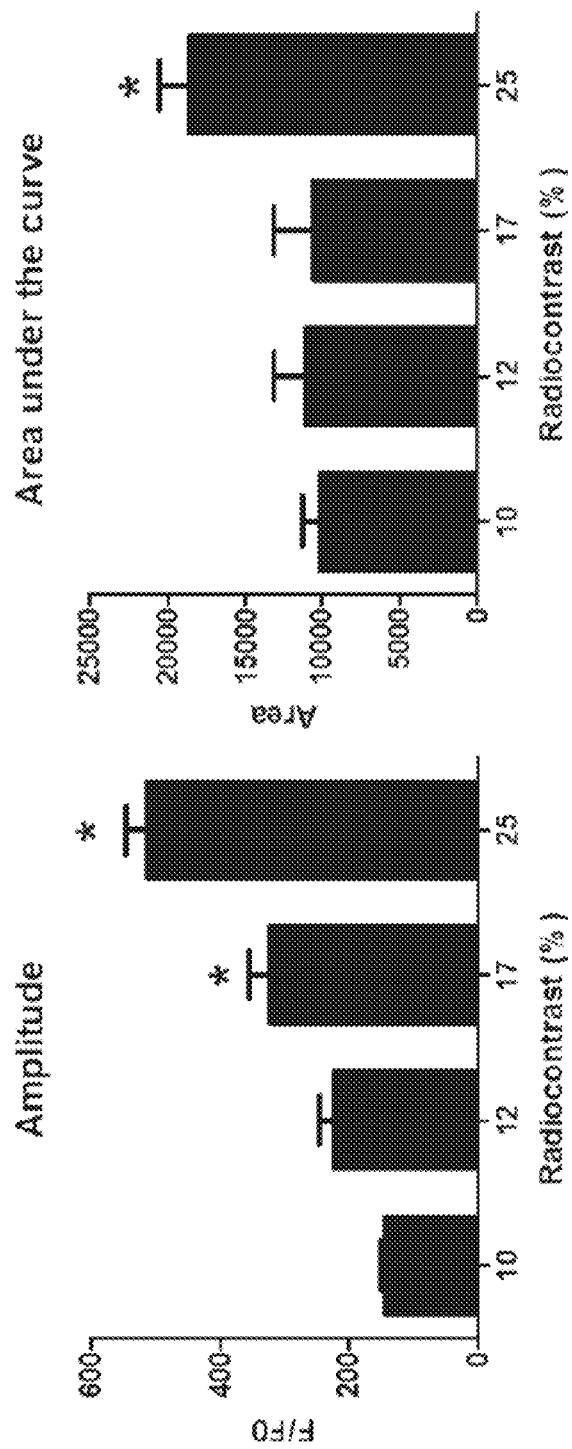
Figure 7C:
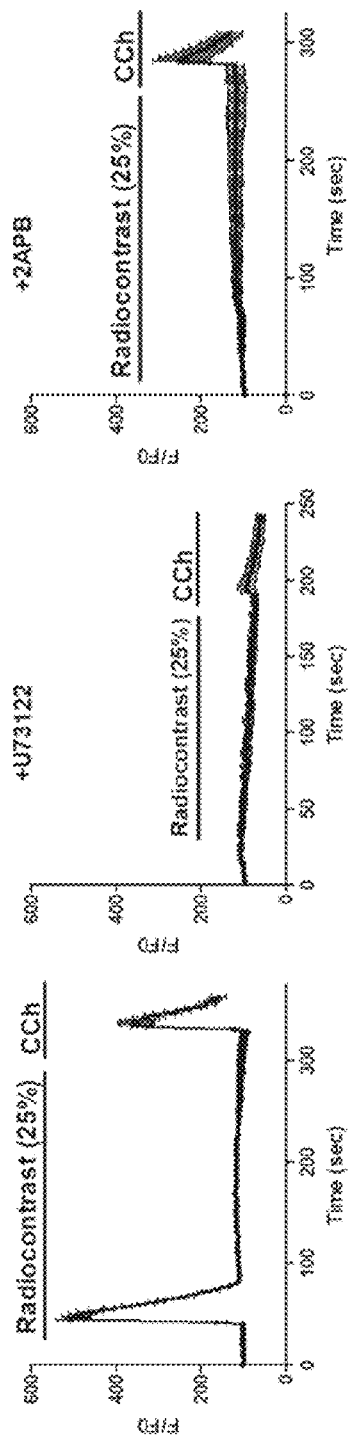
Figure 7D:
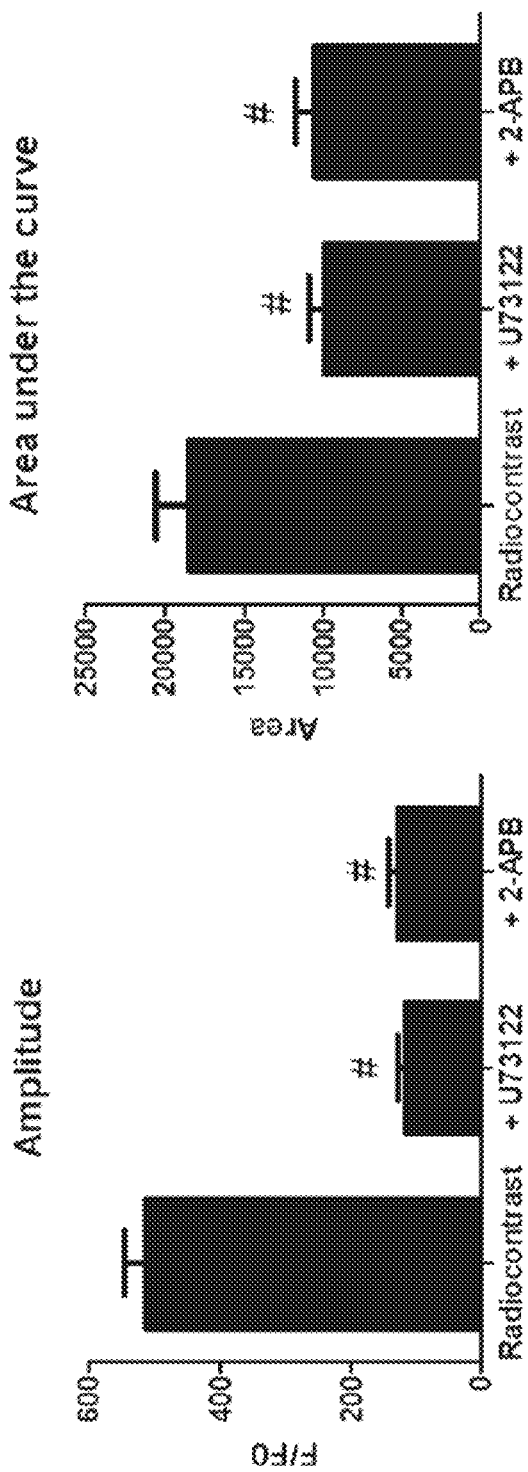
Figure 7E:
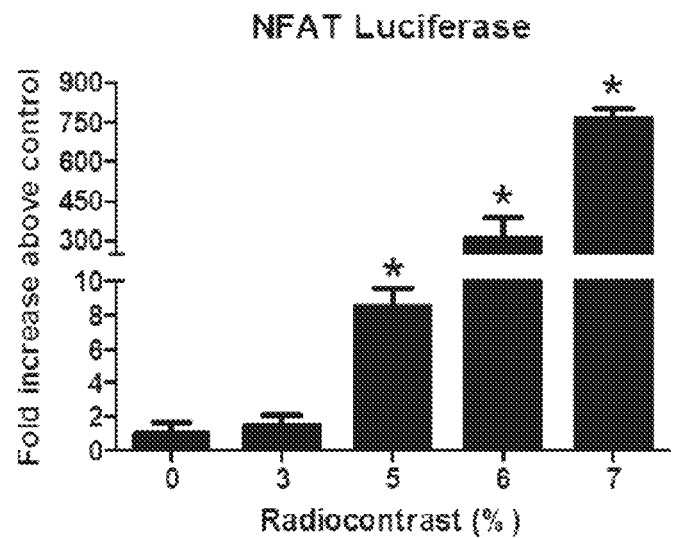
Figure 7F:
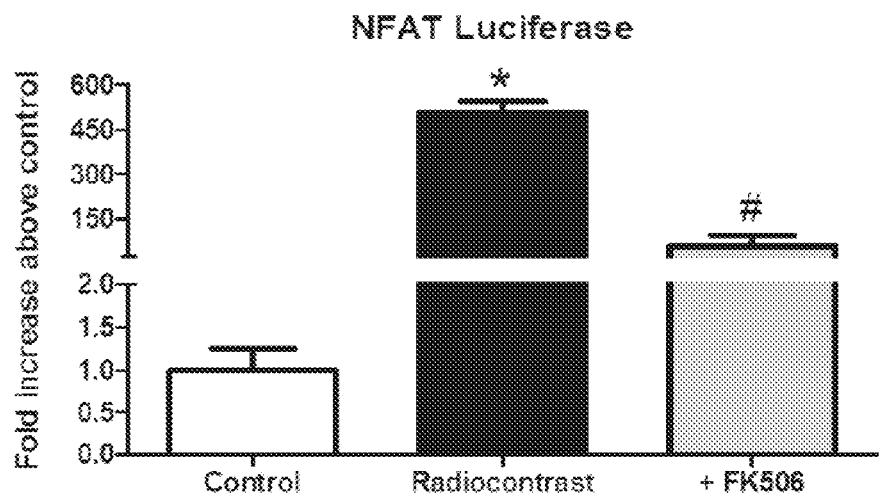
Figure 7G:
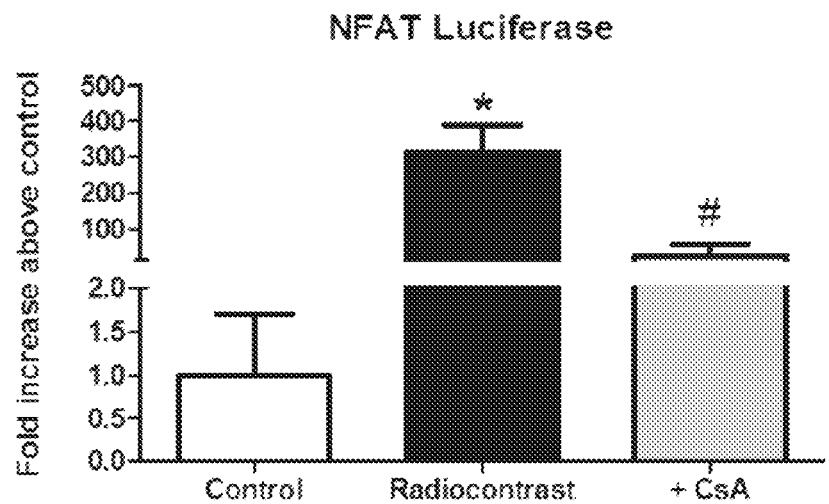
Figure 7H:
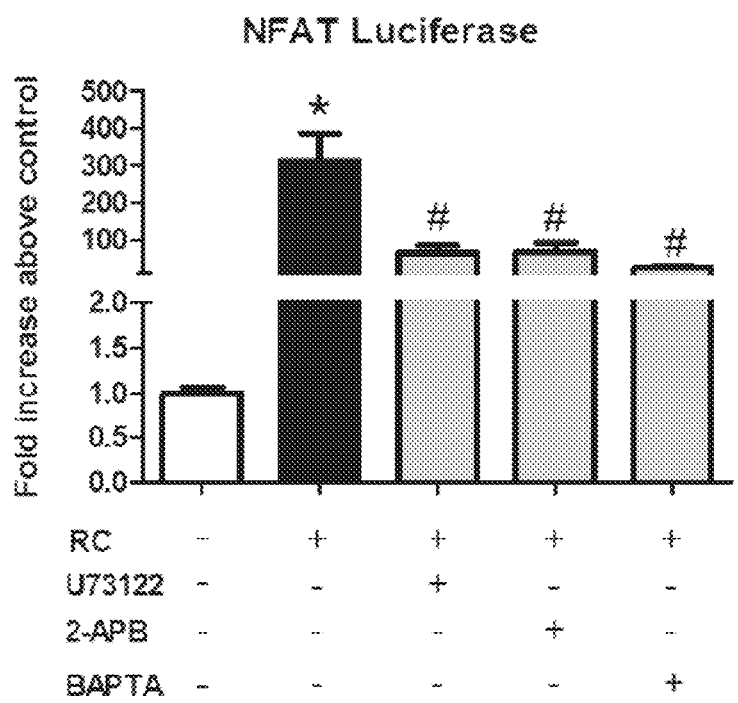

Calcineurin activation is sufficient to induce acinar cell NF-κB activation. To determine whether calcineurin is sufficient to induce NF-κB activation, AR42J cells were infected with an adenovirus containing a constitutively active calcineurin that is a truncated catalytic calcineurin A subunit lacking the auto-inhibitory domain[11] (Ad-ΔCn; FIG. 6E).

NFAT-luciferase activity was maximal after infection with Ad-ΔCn at greater than 1×10$^5$ functional viral infectious units (IFU). Even higher titers of Ad-EGFP (negative control) failed to induce NFAT-luciferase. Interestingly, there was a concentration-dependent increase in NF-κB activation with the Ad-ΔCn. These data demonstrate that in the acinar cell line calcineurin activation is sufficient to induce NF-κB.

RC causes acinar cell necrosis through a $Ca^{2+}$/calcineurin dependent pathway. Propidium iodide (PI) uptake in isolated primary acinar cells is a surrogate for in vivo acinar injury and necrosis during pancreatitis. RC exposure for 6 hr caused a concentration-dependent increase in PI uptake, which was dependent on PLC, IP3R$Ca^{2+}$ release, and a cytosolic $Ca^{2+}$ rise, based on their respective inhibitors or chelator (FIG. 9). Similar results were observed in the AR42J acinar cell line (FIG. 10A). In addition RC caused depletion of ATP levels in both a concentration dependent manner (FIG. 9F). FK506, however, failed to prevent ATP depletion showing that in vitro, calcineurin is not required for the mitochondrial pathology leading to ATP depletion.

Figure 9A:
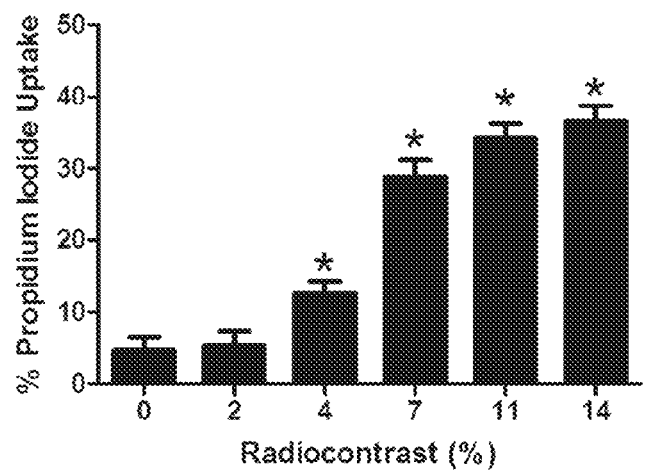
Figure 9B:
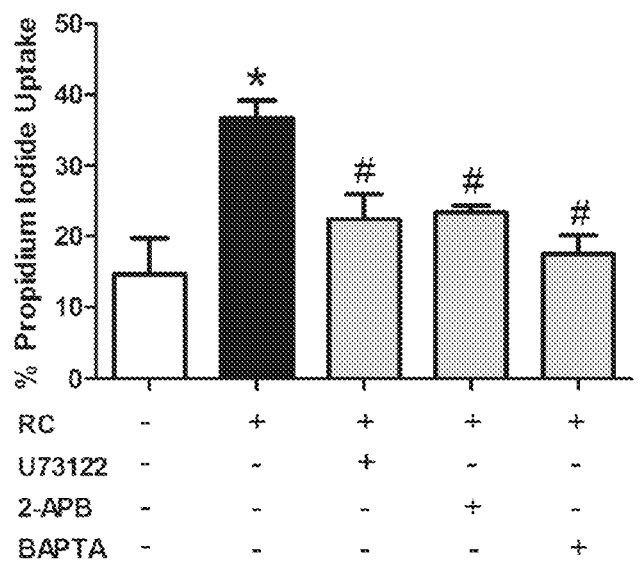
Figure 9C:
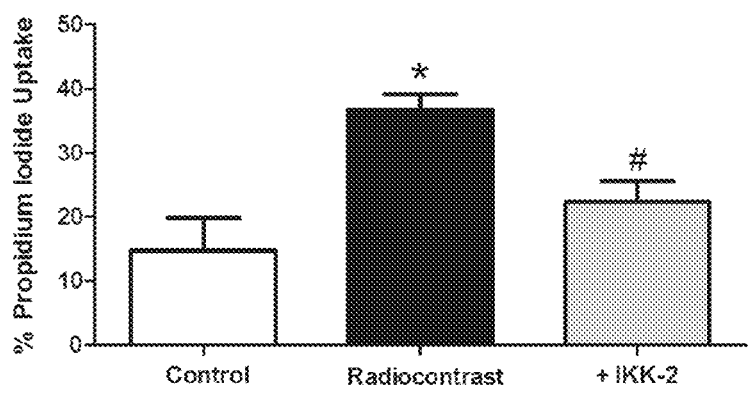
Figure 9D:
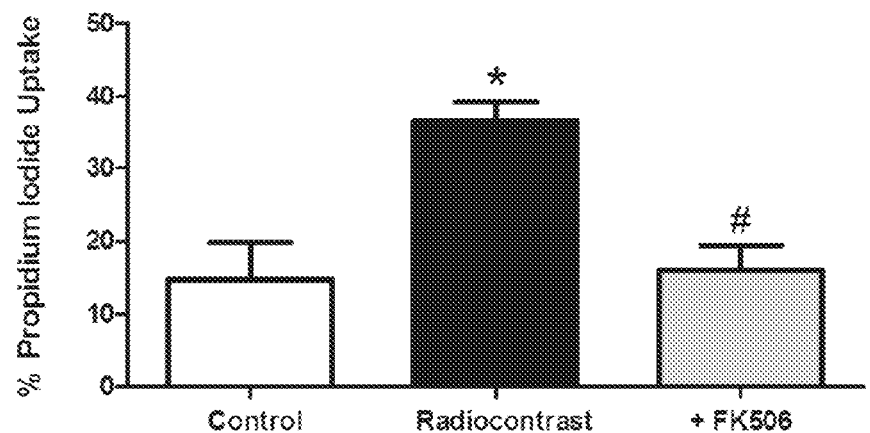
Figure 9D:
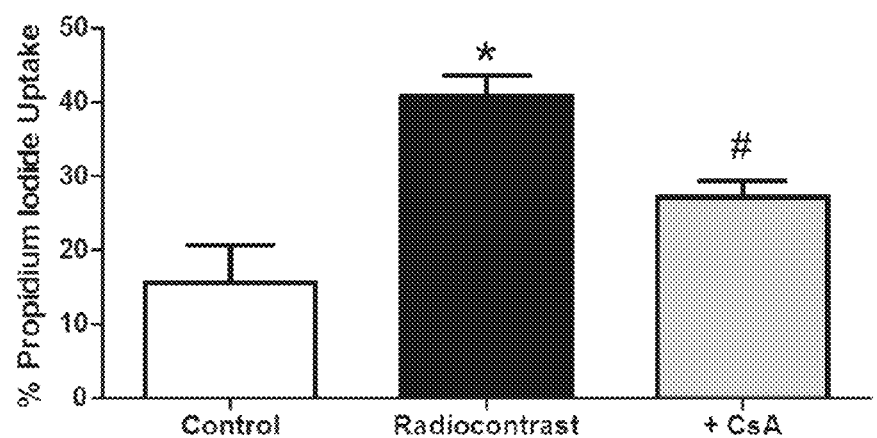
Figure 9E:
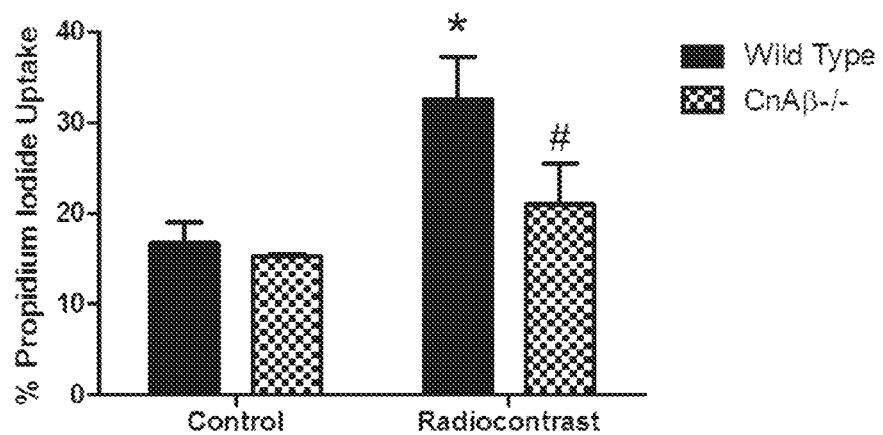
Figure 9F:
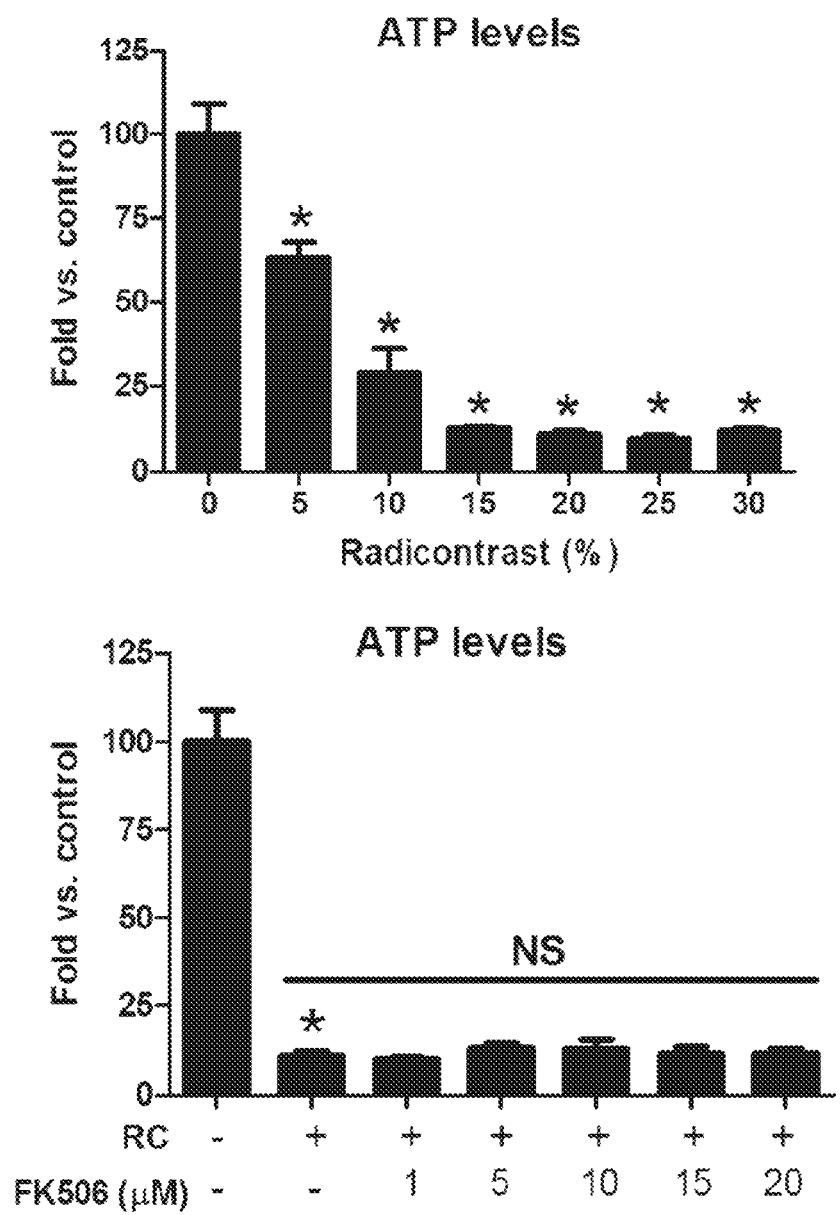

Inhibiting NF-κB translocation with IKK-2 largely prevented PI uptake, as did the calcineurin inhibitors (FIGS. 9C-9D). A stress responsive subunit of calcineurin is the beta isoform of calcineurin A (CnAβ)[13]. Acinar cells isolated from CnAβ knockout mice were protected against PI uptake due to RC (FIG. 9E). Taken together, the data demonstrate that RC induces acinar cell necrosis through a $Ca^{2+}$/calcineurin and NF-κB-dependent pathway.

Pharmacologic and genetic inhibition of calcineurin attenuates RC-induced pancreatitis in mice. The present example also examined whether calcineurin mediates PEP in mice in vivo. (FIG. 11). An intraperitoneal injection of FK506 (1 mg/kg) was given 1 hr prior to intra-ductal RC infusion and then 2.5, 5.5, and 12 hr after the surgical procedure, based on previous regimens that maximally inhibited calcineurin in mice[16,38]. Histological severity of the pancreas following pancreatitis, measured 24 hr after the surgical procedure, was prevented and serum amylase was reduced down to the level of the NS sham condition (FIGS. 11A-11C and FIGS. 10B-10C; P<0.05). This effect was as robust as therapeutic administration of the commonly administered NSAID for PEP, indomethacin (FIG. 12).

Figure 11A:
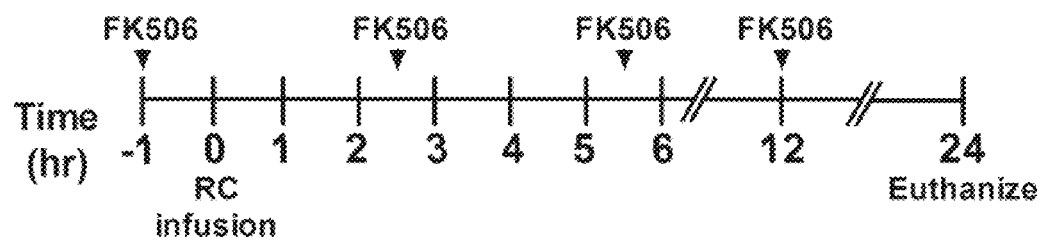
Figure 11B:
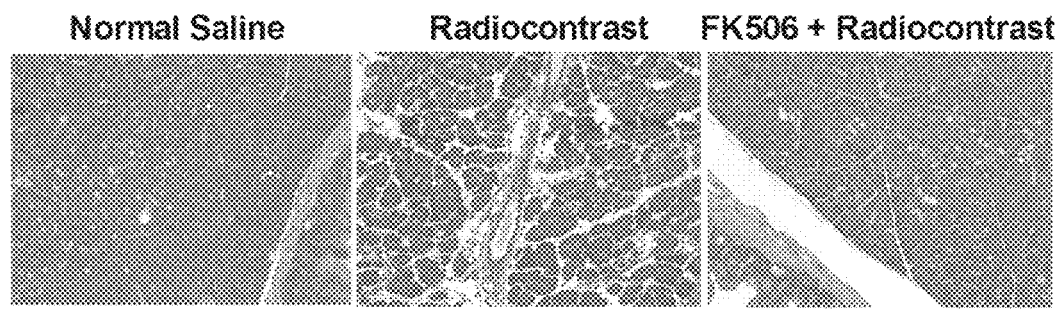
Figure 11C:
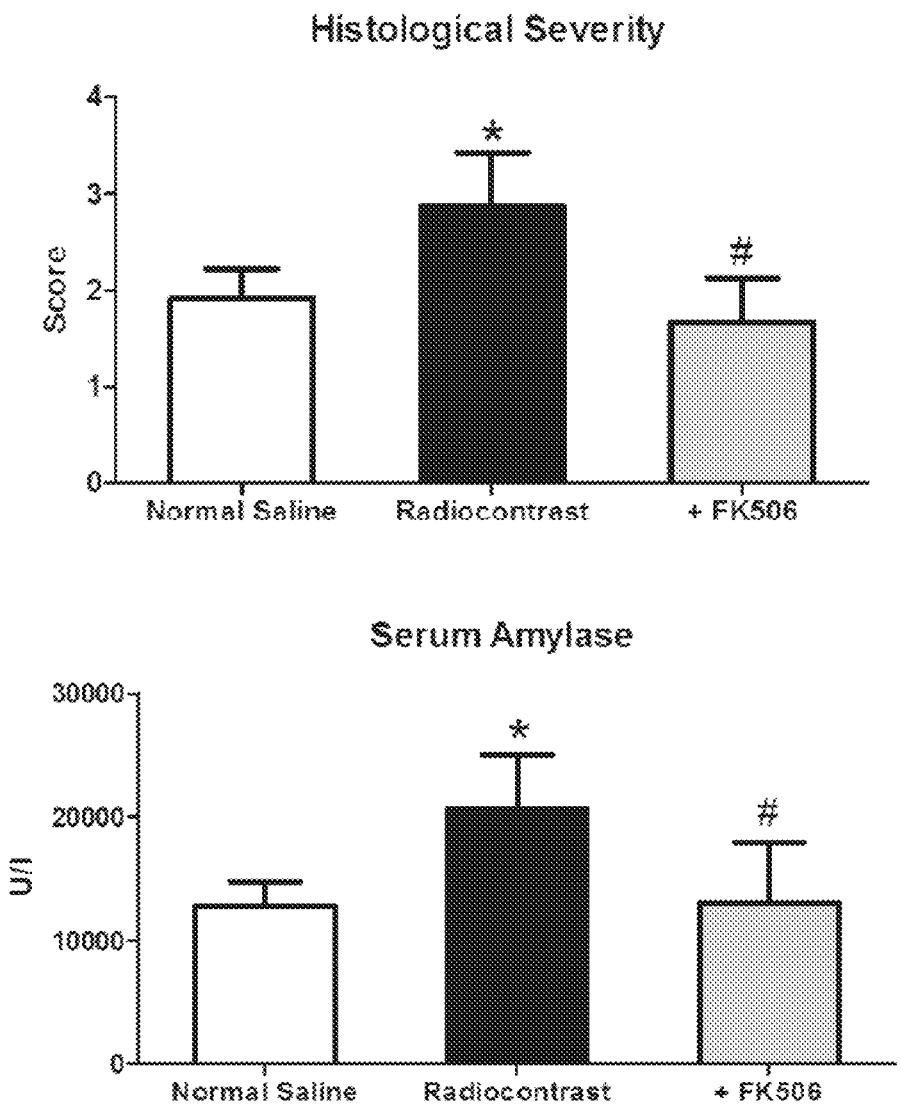
Figure 11D:
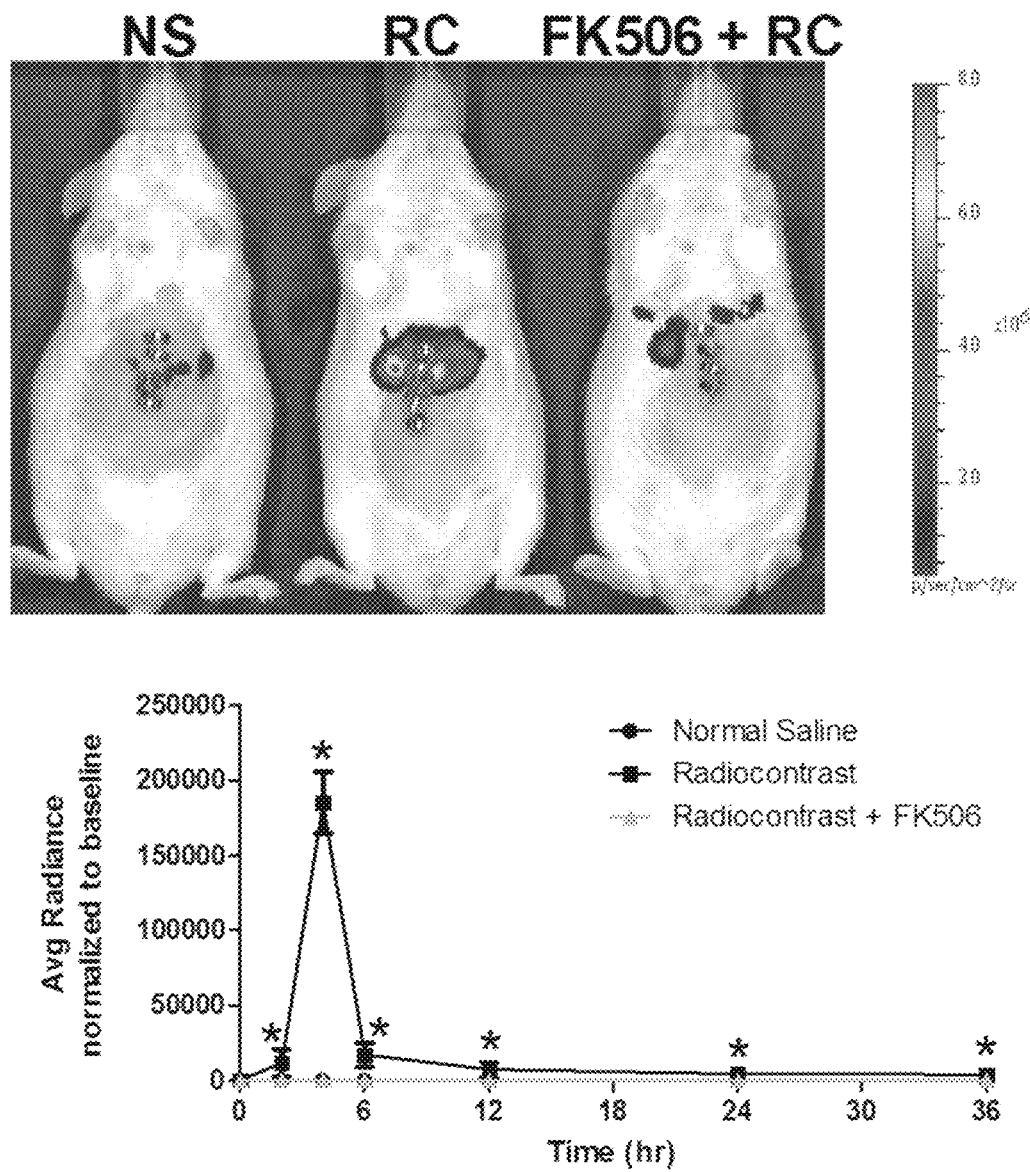
Figure 11E:
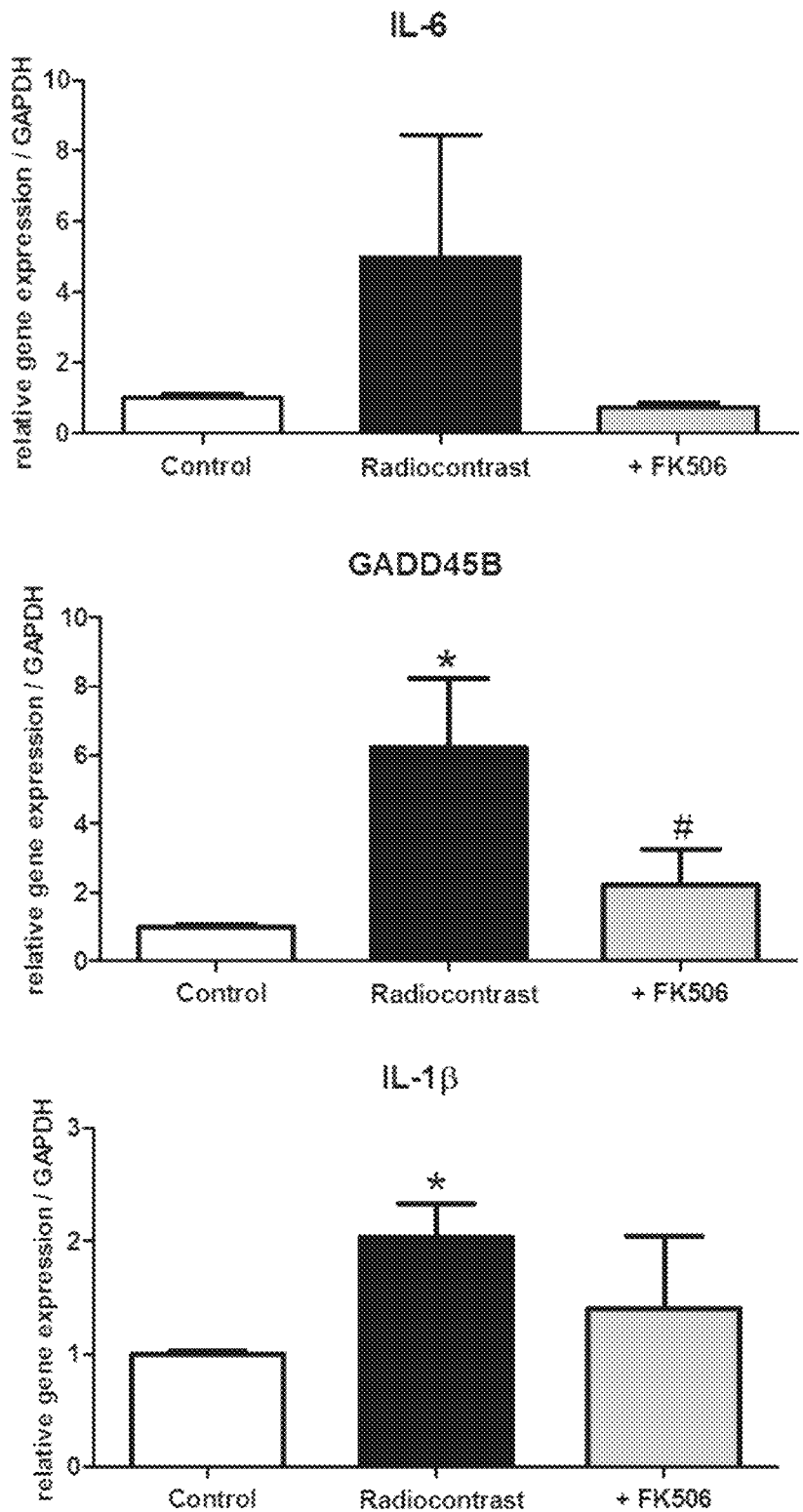
Figure 11F:
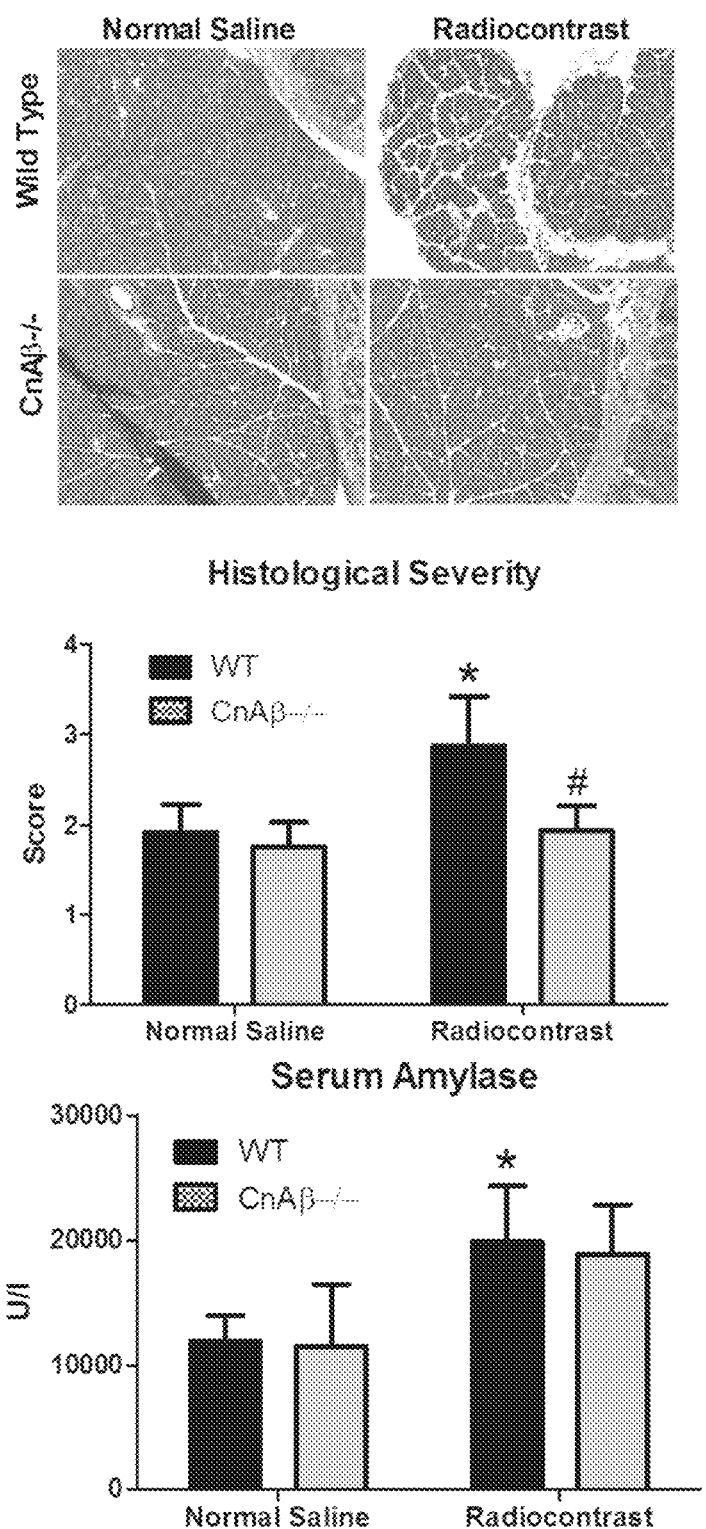

Live, dynamic imaging of pancreatic NF-κB was achieved through a novel AAV6-mediated gene delivery of NF-κB-luciferase into the mouse pancreas by infusing AAV6-NF-κB-luciferase into the pancreatic duct, as detailed in the Methods[39]. Compared to a sham-operated mouse that received intraductal normal saline, RC-infused mice had a 13-fold peak in NF-κB luciferase 4 hr after surgery, within the region of the pancreas (FIG. 11D). FK506 treatment markedly blunted the NF-κB. In addition, the expression of IL-6, GADD45B, and IL-1β was upregulated during RC exposure (FIG. 11E). Pretreatment with FK506 caused a significant reduction in gene expression of IL-6 and GADD45B and a trend toward reduction in IL-1β. The results implicate calcineurin in vivo in inducing NF-κB inflammatory signals. Similarly, CnAβ knockout mice had reduced histological severity of PEP, although serum amylase levels were unchanged compared to wildtype mice (FIG. 11F). Importantly, therapeutic administration of calcineurin inhibitors after PEP induction also protected against RC-induced pancreatitis (FIG. 13). Overall, the results demonstrate that calcineurin is a mediator of pancreatic NF-κB and PEP in mice. Although calcineurin is a target of $Ca^{2+}$, it can also modulate $Ca^{2+}$ by dephosphorylating proteins that mediate $Ca^{2+}$ homeostasis[40]. However, in primary acinar cells, calcineurin inhibition did not affect RC-induced aberrant $Ca^{2+}$ signals (FIG. 14).

6.3. Discussion

The current study is the first demonstration, using the context of pancreatic injury, that RC exposure causes NF-κB activation and results in epithelial and organ damage by inducing aberrant $Ca^{2+}$ signals and activating calcineurin (FIG. 15).

A novel model of PEP in mice was developed. Previous models in larger animals such as dogs employed an endoscopic cannulation of the biliopancreatic ducts[41,42]. More recent models in smaller animals have instilled RC by performing a laparotomy and achieving transduodenal access[22,43]. The major benefit of the current in vivo work in mice was the ability to complement pharmacological inhibition of calcineurin along with the use of calcineurin knockouts.

The present data show that PEP results from a combination of pancreatic ductal pressure and RC exposure, since each additively worsened PEP outcomes. The findings are consistent with clinical data which demonstrate that PEP can be mitigated by inserting a pancreatic duct stent to relieve ductal pressure, as well as by instilling only the minimum necessary amount of RC during an ERCP procedure[5-7,9].

The present example was focused on the effect of RC exposure on the pancreas and the main parenchymal cell the pancreatic acinar cell. RC is known to cause acute kidney injury in high risk patients by inducing hemodynamic instability and it has direct toxic effects on renal cells purportedly through generation of reactive oxygen species (ROS)[34,44] and nuclear translocation of NF-κB[35]. In the acinar cell line, N-acetylcysteine had no effect on NF-κB. The results show that RC has differential effects, depending on the cell type. RC was shown to cause NF-κB activation in a renal cell line but the mechanism of activation was not identified[45,46]. The current study is the first demonstration that RC causes NF-κB activation via aberrant $Ca^{2+}$ signals and calcineurin activation (FIG. 15). Pancreatic NF-κB signals in vivo were imaged in a live, dynamic fashion by delivering NF-κB luciferase through AAV-mediated intraductal gene delivery. This novel technique allowed to focus primarily on pancreatic signals, without the noise from luciferase expression in adjacent organs that is inherent to transgenic mice that globally express NF-κB luciferase reporter[47].

The $Ca^{2+}$ transient emerged soon after RC exposure (within 1-2 min) both in mouse and human acinar cells. Further, the shape of the $Ca^{2+}$ signal in most cells mimicked a high amplitude peak plateau, which is a characteristic pathological signal that precedes acinar cell injury and pancreatitis[25,26,48-53] and which would favor calcineurin activation[54]. A recent report demonstrated that a long incubation (of 4 hr) with ioversol, a RC that is similar to the iohexol and iopamidol we used, caused a slow, globalized increase in baseline cytosolic $Ca^{2+}$ levels in the NRK-52E renal cell line[55]. It was suggested that the RC triggered voltage-gated $Ca^{2+}$ channels or caused reversal of the plasma membrane $Na^+/Ca^{2+}$ exchanger (NCX), so as to favor $Ca^{2+}$ influx. The finding was supported by an earlier report that $Ca^{2+}$ channel blockers improved RC-induced acute kidney injury in rats[56]. In the context of RC-induced pancreatic injury, however, NCX does not appear to be a functional component of the pancreatic acinar cell[25,57]. Thus the acinar cell $Ca^{2+}$ signals with RC were distinct from the faint $Ca^{2+}$ signals described in the NRK-52E cell line or from the non-pancreatic cell lines we tested.

Among the putative targets of $Ca^{2+}$ in pancreatitis, which include the MPTP and kinases, the $Ca^{2+}$-activated serine/threonine phosphatase calcineurin has been implicated as a critical mediator of acinar injury and pancreatic inflammation[16,38,53,58,59]. Calcineurin is a dimer formed by a catalytic A subunit (CnA) and a regulatory B subunit (CnB)[60-62] CnA has three isoforms (alpha, beta, and gamma) and CnB has two isoforms (B1 and B2). Calcineurin is highly conserved and ubiquitous in most cells of the body, although there is differential distribution of its isoforms. The pancreatic acinar cell expresses mostly CnAβ and CnB1[59]. Calcineurin was shown to mediate similar events as aberrant $Ca^{2+}$ including intra-acinar protease activation[58], NF-kB[53,63], and cell injury[59]. In vivo, calcineurin mediated pancreatitis due to caerulein hyperstimulation[38] and bile acid infusion[16].

It is unlikely that there was a direct effect of molecular iodine on the cell or its entry (e.g. via a sodium iodine symporter[64]) because iodine dissociation in properly stored RC is minimal, and sodium iodine administration alone to renal cells does not cause cell injury[35,65]. Calcineurin inhibitors are used clinically as immunosuppressants because they inhibit T-cells[66]. The present example shows, however, that calcineurin within the acinar cell causes acinar pathology and that acinar calcineurin, by itself, might contribute to pancreatitis in vivo. The study provides pre-clinical impetus to conduct clinical trials in order to test the role of calcineurin inhibitors in preventing PEP. More broadly, it is also the first demonstration, in any organ or cell type, that RC induces NF-κB and cell necrosis through aberrant $Ca^{2+}$ signals and that a central $Ca^{2+}$ mediator is calcineurin.

7. EXAMPLE: TARGETED INHIBITION OF PANCREATIC ACINAR CELL CALCINEURIN IS A NOVEL STRATEGY TO PREVENT POST-ERCP PANCREATITIS

7.1. Materials and Methods

Endoscopic retrograde cholangiopancreatography (ERCP) is a common gastrointestinal procedure that confers a risk of acute pancreatitis ranging between 1% and 15%[70]. The efficacy of widely accepted strategies to prevent post-ERCP-pancreatitis (PEP) such as pretreatment with rectal indomethacin[8] has recently been challenged[71,72]. The search for PEP prevention requires uncovering central mechanisms that initiate PEP. Using an ex vivo surrogate model of PEP, derived by isolating primary mouse and human pancreatic acinar cells, we recently demonstrated that common radiocontrast agents used during ERCP induce acinar cell inflammatory signaling and injury through the activation of the calcium-activated phosphatase calcineurin (Cn)[73]. In an in vivo model of PEP in mice, we found that global Cn knockout mice (deficient in CnAβ) or systemic inhibition of Cn with frequent prophylactic dosing of the Cn inhibitors FK506 or cyclosporine A (CsA) prevented PEP. Since Cn is ubiquitously expressed, a crucial unanswered question is whether acinar cell Cn blockade by itself is sufficient to prevent PEP in vivo.

Reagents & Animals. All reagents were purchased from Sigma-Aldrich (St. Louis, Mo.), unless specified otherwise. Mice carrying loxP-flanked ('floxed') alleles of CnB1 (CnB1$^{f/f}$; backcrossed to a C57BL/6 strain) were a kind gift of Dr. Gerald Crabtree[74], and the Ela-CreERT2 transgenic line was a kind gift of Dr. Craig Logsdon[75]. Lox-Stop-Lox tdTomato Red reporter mice were obtained from the Jackson Lab[76]. Both male and female genetically engineered mice were equally used for the in vivo studies. Eight to ten week old wildtype male and female Swiss Webster mice weighing 25 g were used to assess the efficacy of intraductal administration of FK506 and CsA. All mice were housed at 22° C. with a 12 hr light-dark cycle and maintained on a standard laboratory chow with free access to food and water. All animal experiments were performed using a protocol approved by the University of Pittsburgh Institutional Animal Care and Use Committee.

Generation of conditional pancreatic acinar-specific CnB1 knockouts. CnB1$^{f/f}$ mice were crossed with Ela-CreERT2 mice to generate homozygous Ela-CreERT2/CnB1$^{f/f}$ strains. To delete CnB1 in pancreatic acinar cells (CnB1$^{\Delta/\Delta}$), CreERT2/CnB1$^{f/f}$ mice received a cumulative dose of 5-6 mg tamoxifen given intraperitoneally either daily or every other day for a total duration of 5-6 days. PEP was induced one week after the last tamoxifen injection (FIG. 16A). CnB1$^{f/f}$ lines lacking the Ela-CreERT2 insertion served as controls, and they also received tamoxifen.

CnB1$^{\Delta/\Delta}$ genotyping. Genomic DNA was prepared from freshly isolated mouse pancreas and liver tissue, as described[77]. Briefly, the tissue was minced on ice and homogenized in sodium chloride Tris-EDTA (STE) buffer containing proteinase K. The homogenates were incubated at 55° C. for 3 hr with intermittent vortexing. After inactivation of proteinase K, the homogenates were centrifuged at 4° C., and the supernatants containing genomic DNA were precipitated with isopropanol. The precipitated genomic DNA was pelleted at 4° C., washed with 70% ethanol, air-dried, and dissolved in 200 μL of 1×Tris-EDTA buffer for PCR reaction. A schematic of the location and size of the expected amplicons are provided in FIG. 17. Primer sequences were as follows:

TABLE 2

Primer sequences.

| Target amplicon | Forward primer | | Reverse primer | | Expected size (bp) |
|---|---|---|---|---|---|
| 5'loxp site | TCTAGGTAATTA GGGCAGGTGC | SEQ ID NO: 1 | GCTTCTTGAAT CTCTTTCCTAG | SEQ ID NO: 2 | 575 |
| 3'loxp site | GACAGCTATACA GAGAAACCCTG | SEQ ID NO: 3 | AGCCTCCACAT ACACAGATAC | SEQ ID NO: 4 | 290 |
| Cre | GCCTGCATTACC GGTCGA | SEQ ID NO: 5 | TATCCTGGCAG CGATCGC | SEQ ID NO: 6 | 440 |

TABLE 2-continued

Primer sequences.

| Target amplicon | Forward primer | | Reverse primer | | Expected size (bp) |
|---|---|---|---|---|---|
| ERT2 | GCGATCCACGAA ATGAAATG | SEQ ID NO: 7 | GCAGGTTCATC ATGCGGAAC | SEQ ID NO: 8 | 501 |
| CnB1 (floxed out) | CAATGCAGTCCG CTGTAGTTC | SEQ ID NO: 9 | AGCCTCCACAT ACACAGATAC | SEQ ID NO: 10 | 168 |

Figure 17A:
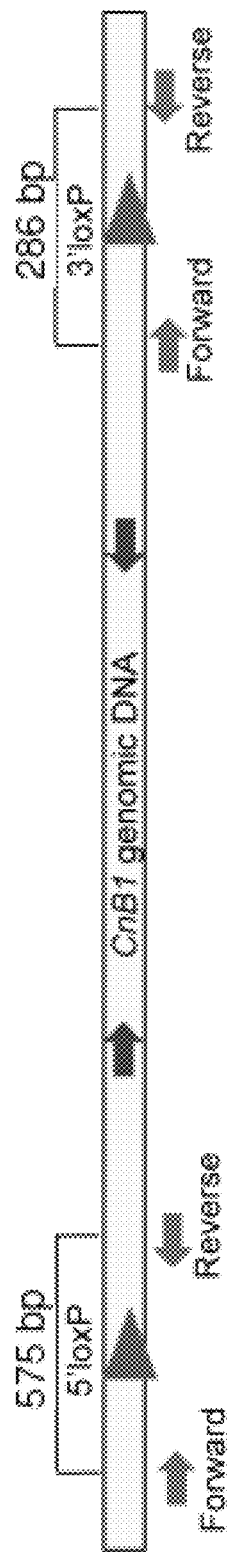
Figure 17B:
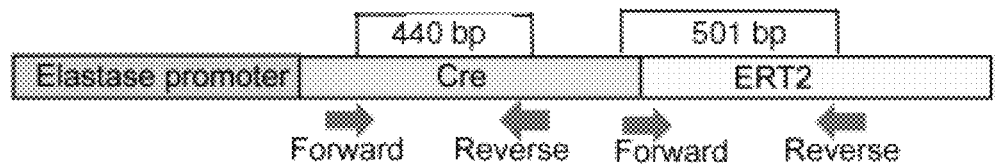
Figure 17C:
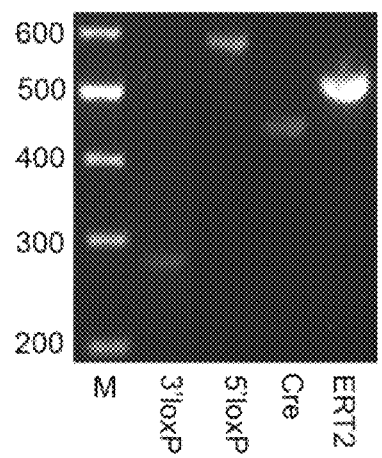
Figure 17D:
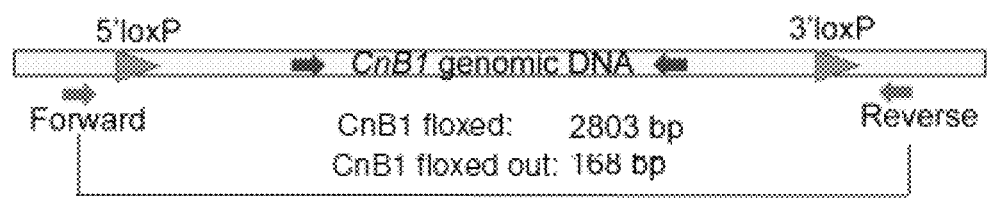
Figure 17E:
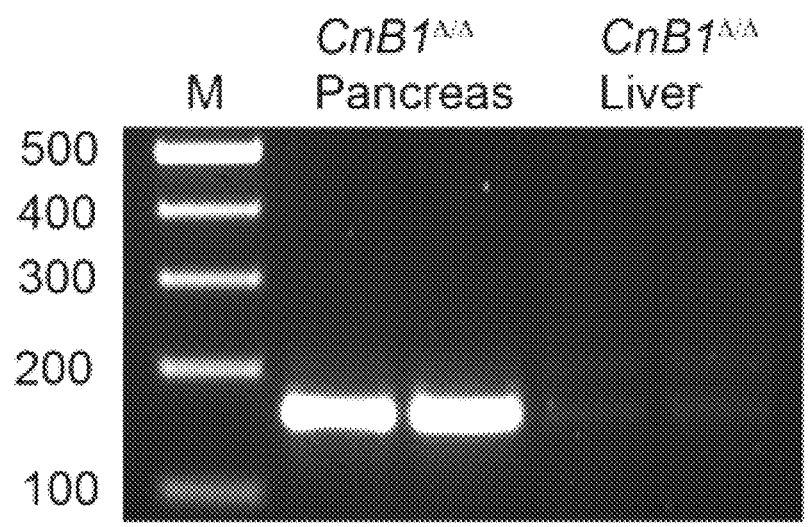
Figure 17F:
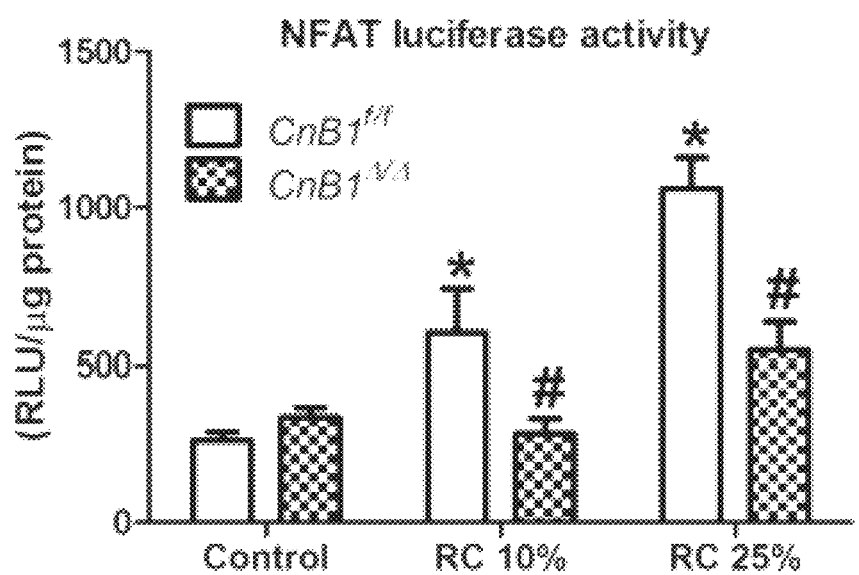

A 168 bp fragment was amplified, as expected, from CnB1$^{\Delta/\Delta}$ pancreatic tissue and was negligible in liver tissue (FIGS. 17D-17E). A 168 bp fragment was also amplified from pancreatic tissue of CnB1$^{f/f}$ mice infused with AAV6-Ela-iCre. The PCR annealing temperature was 61° C., and the template amount was 100 pg of total genomic DNA. The PCR products were separated on a 2% agarose gel and imaged. The DNA band at 168 bp was cut out, purified, and sequenced. All sequences were aligned to the NCBI database and manually verified to confirm CnB1 deletion and that each component (e.g. elastase promoter, Cre, ERT2) was in frame.

NFAT-luciferase activity assay. Isolated pancreatic acinar cells were infected with NFAT-luciferase adenovirus as previously described[16]. Briefly, cells were incubated with NFAT-luciferase adenovirus (titer, $2\times10^9$ IFUs) for 30 min, and they were then exposed to radiocontrast for about 6 hr. After the stimulation, cells were collected, washed with phosphate-buffered saline (PBS) once, lysed with 1× lysis buffer (Promega #E397A, Madison, Wis.), and centrifuged at 12,000 g for 5 min at 4° C. Luminescence was measured from the supernatant using the Luciferase Assay System (Promega #E1483) in a Synergy H1 plate reader (BioTek, Winooski, Vt.), and total protein, determined by the BCA method (Thermo Scientific, Rockford, Ill.), was used to normalize the data.

Adenovirus-associated virus (AAV) 6 constructs. AAV6 plasmids were generated by cloning a pEla-iCre or pCMV-ZsGreen into a pAAV-MCS plasmid (Cell Biolab #VPK-410; San Diego, Calif.) as previously described[19,39]. Once cloned, the AAV6 plasmid was transfected into HEK293 cells along with two helper plasmids: (1) pAAV-RepCap (Applied Viromics; cat #0912-06; Fremont, Calif.), which is a packaging plasmid that carries the serotype 6 rep and cap genes; and (2) pHelper (Applied Viromics; cat #0913; Fremont, Calif.), which is a plasmid that carries the helper genes. Cells were collected 72 hr after transfection and suspended in lysis buffer containing 50 mM Tris, 150 mM NaCl and 2 mM MgCl2.

Purification of the AAV6 for in vivo administration. The AAV6 were purified as previously described[21,39]. Briefly, transfected HEK293 cells were freeze/thawed three times to release the AAV6 virus. Cell lysates were treated with benzonase (0.05 units) at 37° C. for 30 min, followed by 1% sodium deoxycholate at 37° C. for 30 min. Lysates were spun at 2500×g for 10 min, and the supernatant was collected. AAV6 was precipitated using a 1:4 mixture of 40% polyethylene glycol (PEG-800) and 2.5 M sodium chloride for 2 hr at 0° C. The solution was spun at 2500×g for 30 min to collect the PEG pellet. The pellet was re-suspended in HEPES buffer (50 mM), treated with an equal volume of 100% chloroform, spun at 2500×g for 10 min, and air-dried for 30 min. Two phase partitioning was performed using 50% ammonium sulfate and 40% PEG-800 and spun at 2500×g for 15 min. The ammonium sulfate phase was collected and dialyzed using a 10 kDa molecular weight cutoff Slide-A-Lyser Dialysis Cassette (Thermo Scientific #66810) for 4 hr. Dialysis was repeated a second time for 16 hr. The AAVs were concentrated using a 50 kDa centrifugal filter unit (Millipore #UFC905024, Billerica, Mass.) and stored at −80° C. The QuickTiter AAV Quantitation Kit (Cell Biolabs #VPK-145, San Diego, Calif.) was used to measure viral concentrations.

Pancreatic ductal infusion of the AAV6 into CnB1$^{f/f}$ mice. The surgical procedure for retrograde pancreatic ductal infusion of the AAV6 was as previously described[73]. Briefly, 100 μl of purified AAV6 (titer $2\times10^{12}$ PFU) was infused into the biliopancreatic duct at a rate of 10 μl/min for 10 min using a P33 peristaltic syringe pump (Harvard Apparatus, Holliston, Mass.). Surgical anesthesia was achieved by inhaling isoflurane and oxygen. A single injection of the analgesic buprenorphine (0.075 mg/kg) was given immediately after the surgery. Mice recovered on a heating pad for 30 min and were housed for 4-6 weeks with free access to food and water before induction of PEP. To verify the efficacy of the AAV6 infusion, Lox-Stop-Lox tdTomato Red reporter mice were used. One hundred microliters of purified AAV6 Ela-iCre (titer $2\times10^{12}$ PFU) was infused into the pancreatic duct as described above. Five weeks after the surgery, pancreas tissue, along with the abdominal organs en bloc were imaged using a fluorescence dissecting microscope and also sectioned. Induction of post-ERCP pancreatitis. PEP was induced as previously described[73]. Briefly, 100 μl iohexol (Omnipaque, GE Healthcare, Princeton, N.J.) was infused retrograde into the biliopancreatic duct at a rate of 20 μl/min for 5 min. Mice from the ductal manipulation (DM) group received retrograde infusion of 50 μl normal saline into pancreatic ductal at a lower rate of 10 μl/min for 5 min. Mice were euthanized 24 hr after PEP induction by $CO_2$ inhalation and cervical dislocation. Mice from the sham group received laparotomy only.

Serum amylase measurement. Blood was collected by retro-orbital bleed 6 h after PEP induction. Serum was prepared by centrifuging at 1,500×g for 10 min at 4° C. Serum amylase was measured using a Phadebas Kit (Amersham Pharmacia, Rochester, N.Y.) according to the manufacturer's instruction.

Figure 18A:
Figure 18B:
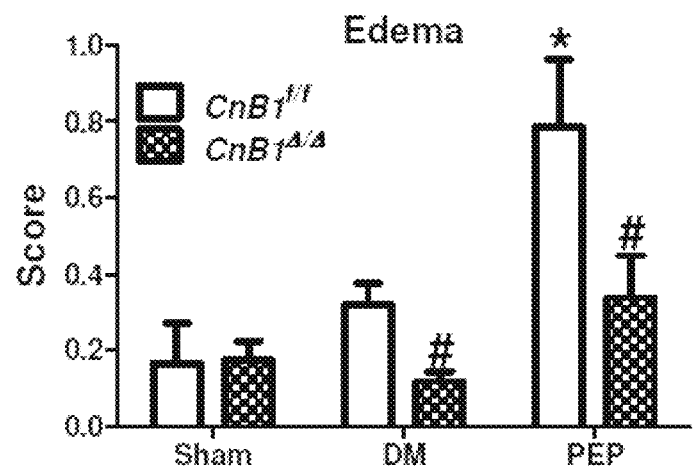
Figure 18C:
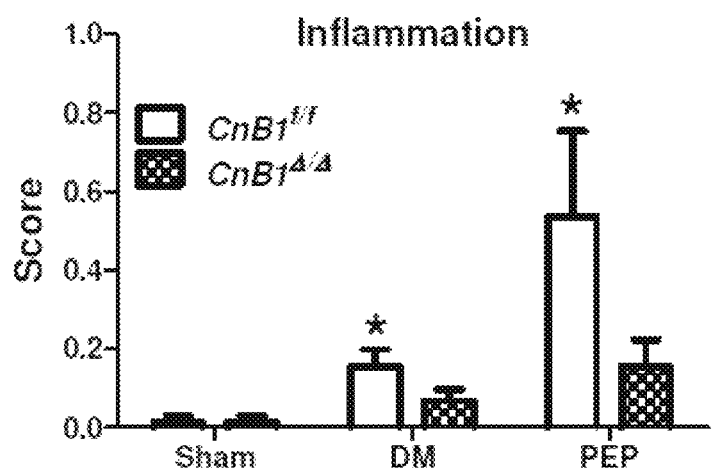
Figure 18D:
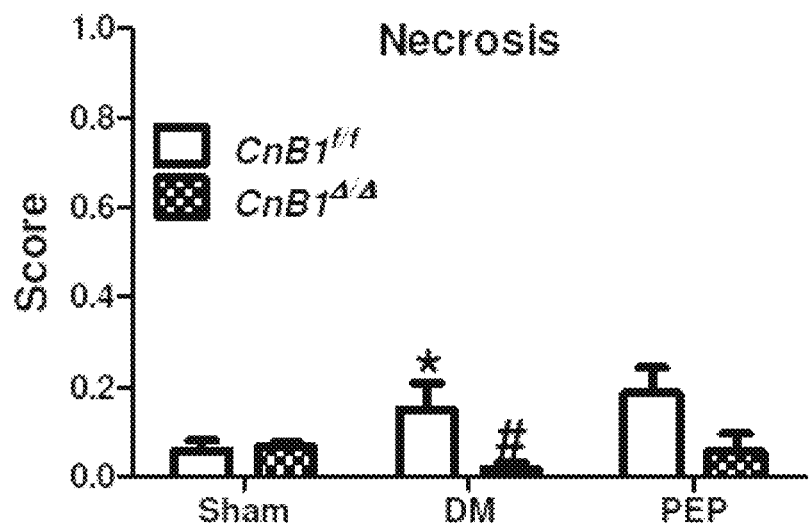
Figure 18E:
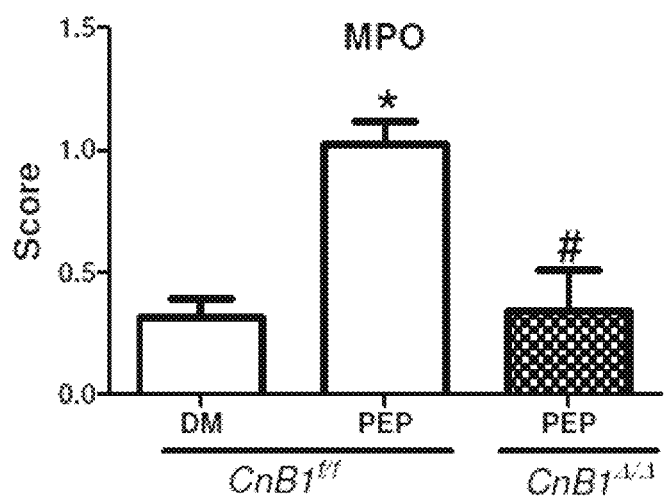
Figure 19A:
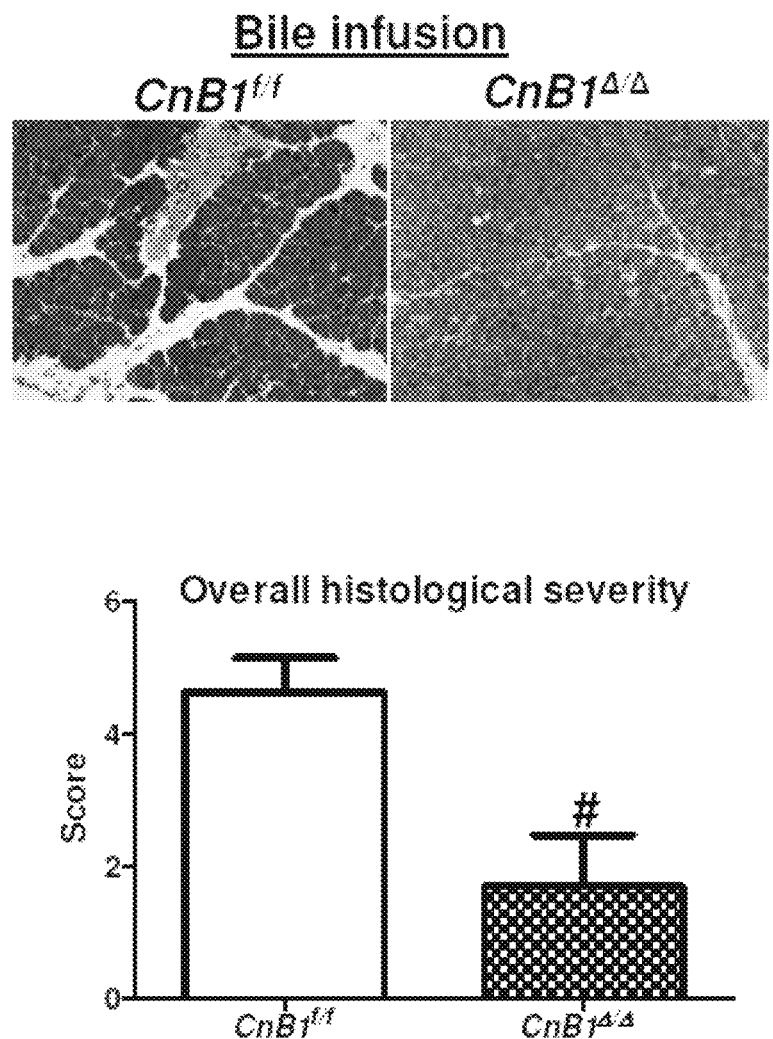
Figure 19B:
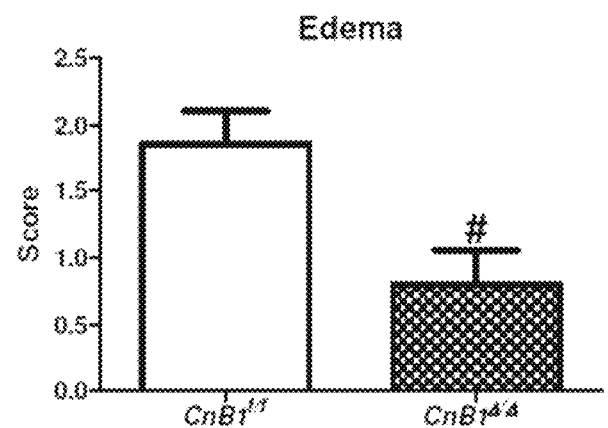
Figure 19C:
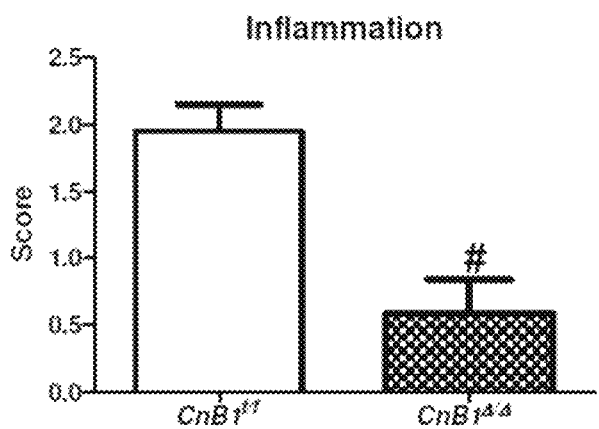
Figure 19D:
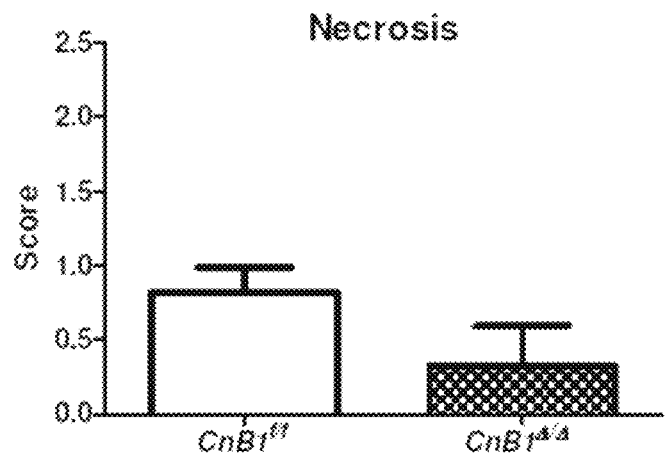

Pancreatic histopathology and image analysis. The pancreas, duodenum, and spleen were placed en bloc in a cassette in order to maintain anatomical orientation (FIG. 18A). The tissues were fixed in 4% paraformaldehyde at room temperature for 24 hr. Paraffin-embedded sections were stained with hematoxylin and eosin (HE). Ten systematically selected fields at 200× magnification were graded in a blinded fashion from the head of the pancreas, which was identified by its juxtaposition to the duodenum. The grading score gave equal weight (from 0 to 3) for edema, inflammatory infiltration, and necrosis, as described[5]. Edema indices were further delineated objectively by performing intensity thresholding using ImageJ software (NIH, Bethesda, Md.). At least 5 images from each slide were selected for the analysis. Each image was setup to the same color threshold. Labelled areas within the parenchyma were marked as edema, and their surface area was calculated as a percentage of the total parenchymal area.

Immunohistochemistry. Immunohistochemistry (IHC) for myeloperoxidase (MPO) was performed from paraffin-embedded tissue sections using a Leica Bond-Max Fully Automated IHC and ISH Staining System (Leica, Buffalo Grove, Ill.) in a semi-automated manner. All of the products for the IHC for MPO were purchased from Leica, including the primary antibody. The slides were loaded on the Bond system, and the program was set as follows: Deparafinized using Bond Dewax Solution (AR9222), dehydrated with alcohol, incubated with MPO (PA0491) primary antibody for 15 min, incubated with Bond polymer refine detection kit (DS9800) containing horseradish peroxidase (HRP)-linkers, Hydrogen peroxide block to quench endogenous peroxidase activity, Biotin-free system. 3,3'-diaminobenzidine tetrahydrochloride hydrate (DAB), and hematoxylin counterstaining. The slides were automatically washed using either Bond Wash Solution (AR9590) or distilled water before moving to the next step. After systematic optimization of the antibody using positive and negative control tissues, the ideal conditions for MPO were found to be MPO BRTU (Bond Ready to Use) solution, with no pretreatment needed, a 15 min antibody incubation time, with 8 min post primary and 8 min DAB incubation times. Five systematically selected fields at 50× magnification were graded in a blinded fashion from the head of the pancreas. A score from 0 to 3 was used to grade the extent of brown color in each field.

Statistical analysis. Data were expressed as mean±SEM. Statistical analysis was performed using GraphPad Prism 6 (La Jolla, Calif.). Comparisons were performed using an unpaired T-test. A P-value ≤0.05 was considered significant.

7.2. Results

To delete Cn selectively in acinar cells, a mouse line containing foxed alleles for the critical regulatory subunit B1 (CnB1) was crossed with a tamoxifen-inducible Cre line driven by a full-length acinar-specific rat pancreatic elastase promoter[75] (FIG. 16A and FIG. 17). Even in a mild model of PEP induced by low-pressure intraductal infusion of normal saline, which was termed duct manipulation (DM), there was a near complete reduction in histological damage among the acinar cell-specific CnB1 deficient mice (CnB1$^{\Delta/\Delta}$; FIG. 16B). Furthermore, in a more severe model of injury which mimics PEP by infusing radiocontrast at higher pressure (by doubling the rate and volume), the CnB1$^{\Delta/\Delta}$ mice also had a marked reduction in histological damage by 75% down to the level of the sham-operated negative control arm. Each parameter of the overall histological score was diminished, including edema, inflammatory infiltrate (additionally examined by MPO staining), and necrosis (FIG. 16C and FIG. 18). These findings indicate that acinar cell Cn mediates PEP in vivo. In addition to the mild and moderate models of PEP, acinar cell-specific Cn deletion also protected against a disparate model of acute pancreatitis induced by infusion of the bile acid taurocholate (FIG. 19). The findings showed the broad importance of acinar cell Cn in mediating pancreatic injury.

Figure 21A:
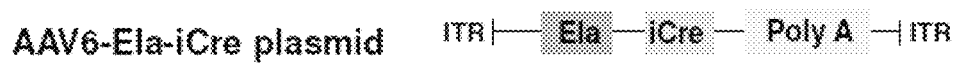
Figure 21B:
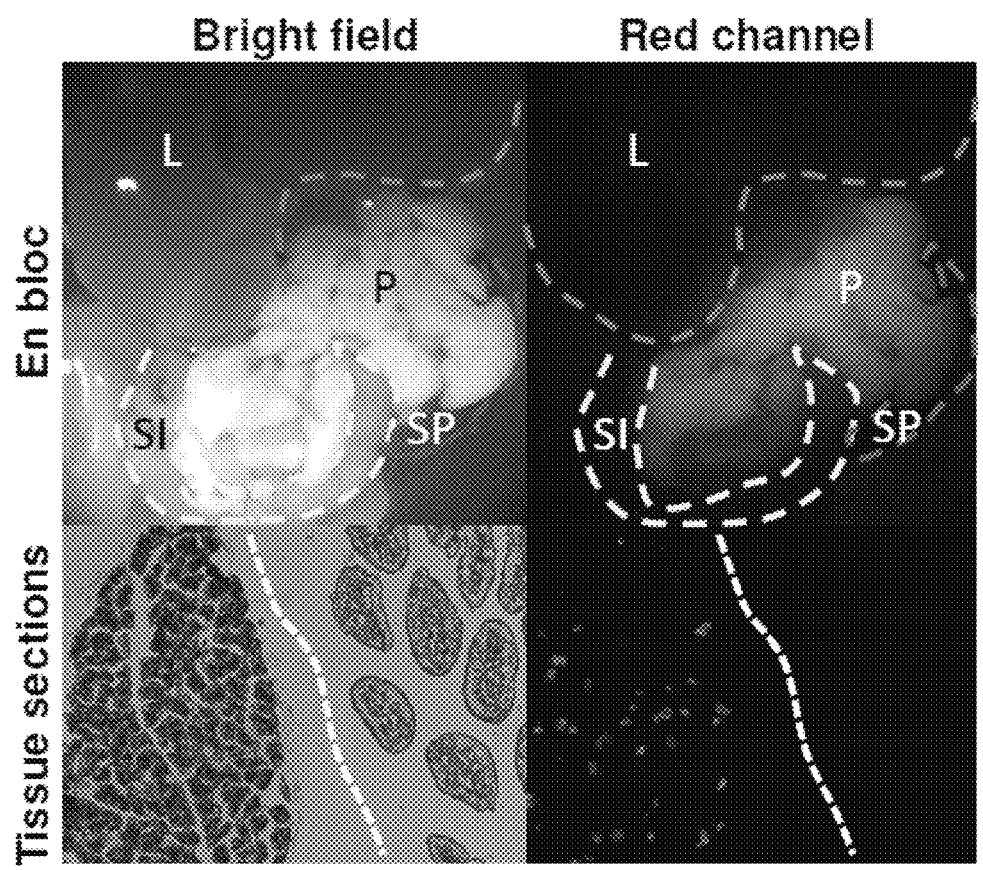
Figure 21C:
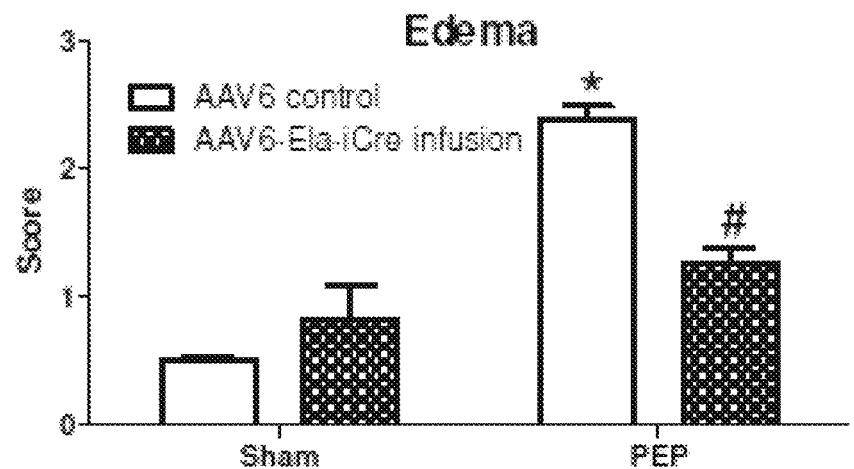
Figure 21D:
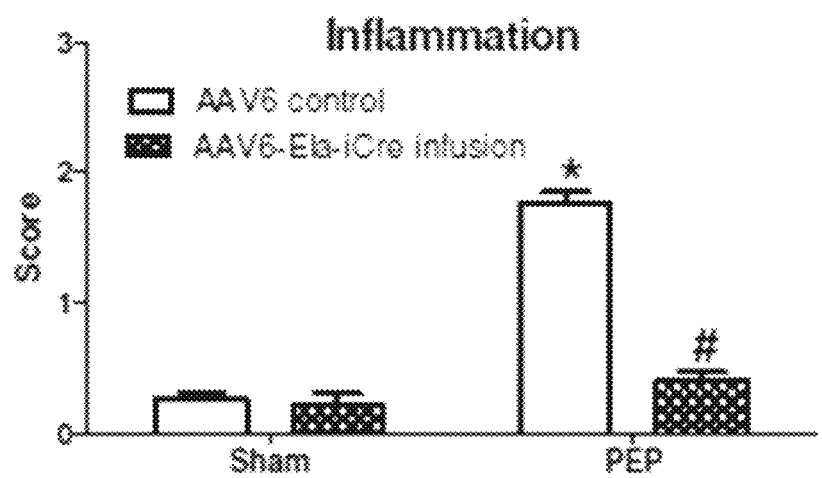
Figure 21E:
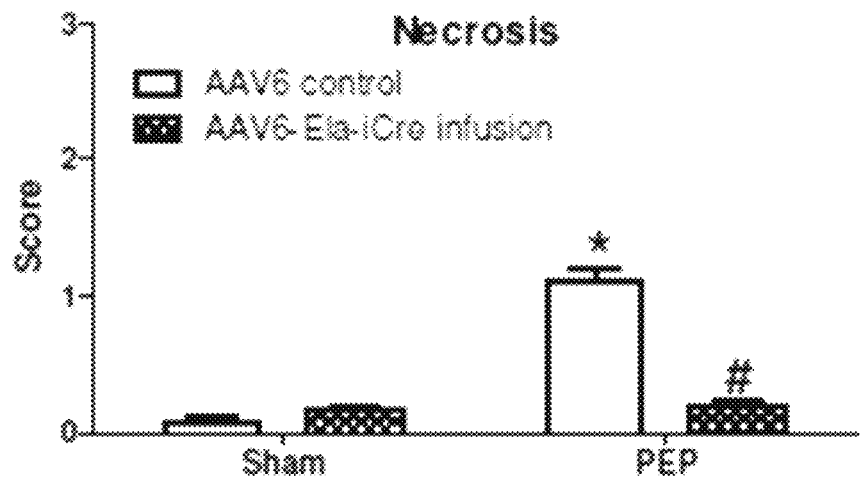
Figure 21F:
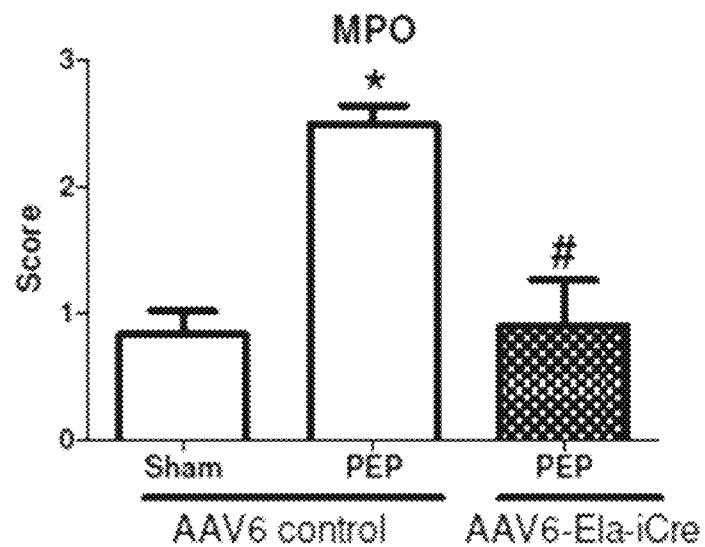

The breeding strategy for acinar cell Cn knockouts was complemented by generating an adeno-associated virus serotype 6 vector (AAV6) vector which houses an enhanced version of Cre (iCre)[78] that is driven by a shorter, independently constructed rat pancreatic elastase promoter[79] (FIG. 20A and FIG. 21A). Among serotypes, AAV6, along with AAV8, offer the highest infection efficiency into acinar cells[39,80]. As proof of principle for targeting acinar cells, the AAV6-Ela-iCre induced acinar cell fluorescence in Lox-Stop-Lox tdTomato Red reporter mice (FIG. 21B). Intraductal infusion of AAV6-Ela-iCre into the pancreas of CnB1$^{f/f}$ mice resulted in acinar cell-specific deletion of CnB1, and upon recovery from the intraductal procedure, pancreatic injury induced by PEP was reduced by 90% down to control levels (FIGS. 20B-20C and FIGS. 21C-21F).

Figure 23A:
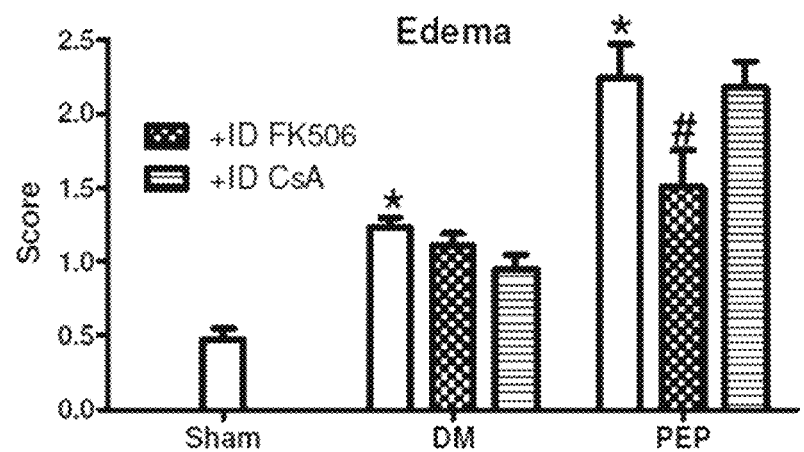
Figure 23B:
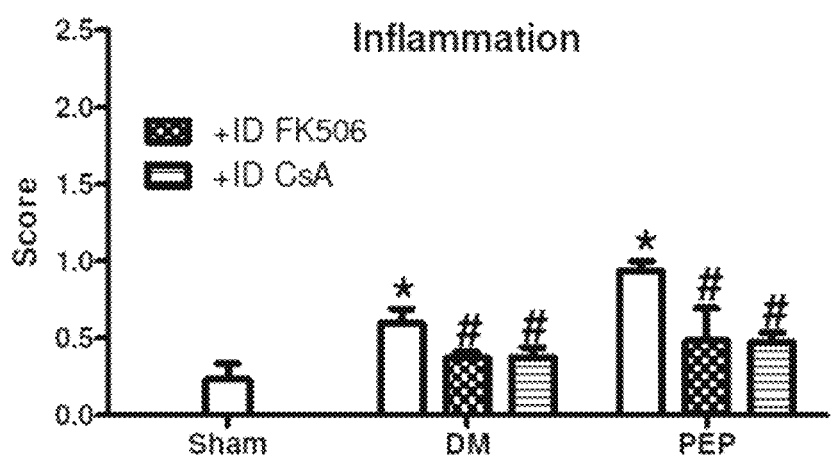
Figure 23C:
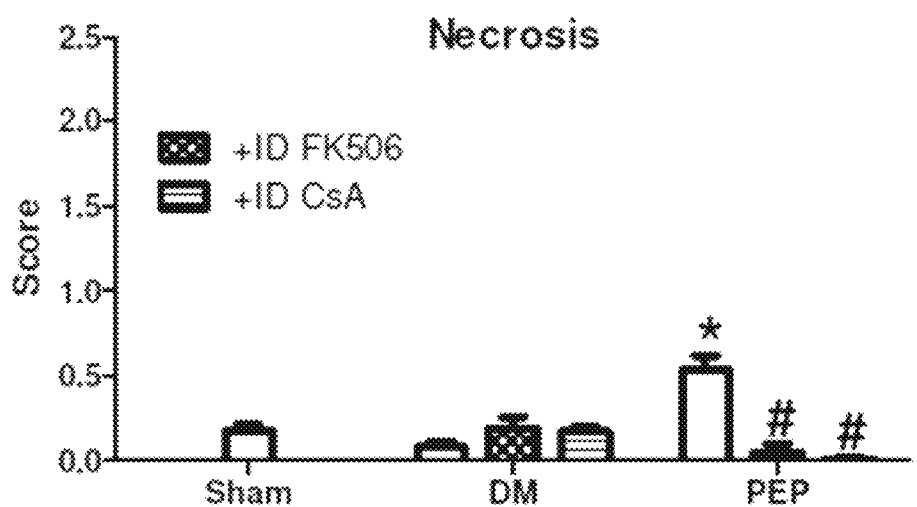
Figure 23D:
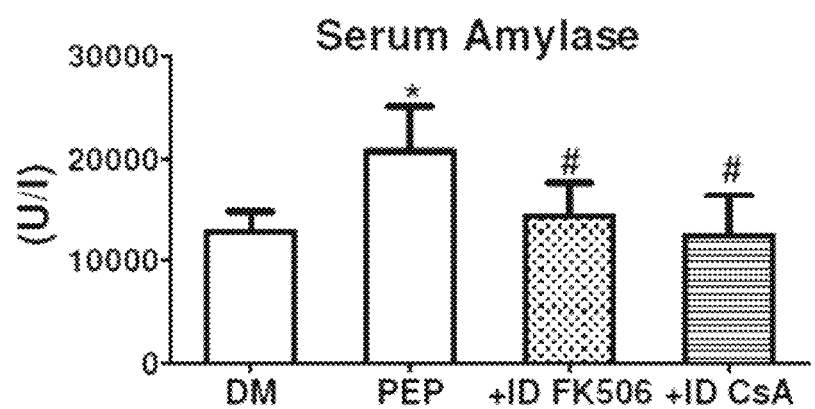

Systemic inhibition of Cn with administration of multiple doses of Cn inhibitors before and after PEP induction was previously shown to protect against PEP[73]. However, the current findings, with the two genetic Cn deletion models, that acinar cell Cn in vivo is necessary for PEP prompted us to interrogate whether selectively targeting acinar cell Cn activity by giving a single, acute dose of Cn inhibitor, along with the radiocontrast infusion, could mitigate PEP. This unique compartmentalized method of delivery of a small amount of drug would additionally obviate the toxicity profile of the inhibitors. FK506 (1 μM) and CsA (10 μM) each were easily dissolved in the ready-to-use iohexol formulation. Although intraductal FK506 or CsA therapy did not affect the mild histological damage seen with DM, the intervention reduced the severity of the moderate model of PEP by 61% and 37% down to sham levels, respectively (FIGS. 22A-22B and FIGS. 23A-23C). The serum amylase elevations seen with PEP 6 hr after infusion were also reduced (FIG. 23D).

7.3. Discussion

In summary, using two complementary genetic approaches to delete acinar cell Cn in vivo and in two severity models of PEP in mice, as well as a bile infusion model of pancreatitis, we show that PEP and pancreatitis can be largely prevented by acinar cell Cn deletion. The translational corollary to these significant findings is that intraductal delivery of Cn inhibitors, to target acinar cell Cn in vivo, was also shown to reduce PEP. These novel findings reconcile the paradox that chronic and systemic administration of Cn inhibitors could predispose to pancreatitis and pancreatic fibrosis[81,82] while acute and targeted delivery to the pancreas protects against pancreatitis. This work provides the impetus for launching clinical trials to test the efficacy of a novel ERCP infusion formulation containing Cn inhibitors to prevent PEP.

8. REFERENCES

1. Chutkan R K, et al. (2006) ERCP core curriculum. Gastrointest Endosc 63(3):361-376.
2. Mazen Jamal M, Yoon E J, Saadi A, Sy T Y, & Hashemzadeh M (2007) Trends in the utilization of endoscopic retrograde cholangiopancreatography (ERCP) in the United States. Am J Gastroenterol 102(5):966-975.
3. Frank C D & Adler D G (2006) Post-ERCP pancreatitis and its prevention. Nat Clin Pract Gastroenterol Hepatol 3(12):680-688.
4. Andriulli A, et al. (2007) Incidence rates of post-ERCP complications a systematic survey of prospective studies. Am J Gastroenterol 102(8):1781-1788.
5. Fazel A, Quadri A, Catalano M F, Meyerson S M, & Geenen J E (2003) Does a pancreatic duct stent prevent post-ERCP pancreatitis? A prospective randomized study. Gastrointest Endosc 57(3):291-294.
6. Sofuni A, et al. (2007) Prophylaxis of post-endoscopic retrograde cholangiopancreatography pancreatitis by an endoscopic pancreatic spontaneous dislodgement stent. Clin Gastroenterol Hepatol 5(11):1339-1346.
7. Smithline A, et al. (1993) Effect of prophylactic main pancreatic duct stenting on the incidence of biliary endoscopic sphincterotomy-induced pancreatitis in high-risk patients. Gastrointest Endosc 39(5):652-657.

8. Elmunzer B J, et al. (2012) A randomized trial of rectal indomethacin to prevent post-ERCP pancreatitis. N Engl J Med 366(15):1414-1422.
9. Tarnasky P R, et al. (1998) Pancreatic stenting prevents pancreatitis after biliary sphincterotomy in patients with sphincter of Oddi dysfunction. Gastroenterology 115(6): 1518-1524.
10. Wilkins B J, Dai Y-S, Bueno O F, et al. Calcineurin/NFAT Coupling Participates in Pathological, but not Physiological, Cardiac Hypertrophy. Circ Res 2004; 94:110-118.
11. O'Keefe S S J, Tamura J J, Kincaid R R L, et al. FK-506- and CsA-sensitive activation of the interleukin-2 promoter by calcineurin. Nature 1992; 357:692-694.
12. Ji B, Gaiser S, Chen X, et al. Intracellular trypsin induces pancreatic acinar cell death but not NF-kappaB activation. J Biol Chem 2009; 284:17488-98.
13. Bueno O F, Brandt E B, Rothenberg M E, et al. Defective T cell development and function in calcineurin Abeta-deficient mice. PNAS 2002; 99:9398-9403.
14. Perides G, van Acker G J, Laukkarinen J M, et al. Experimental acute biliary pancreatitis induced by retrograde infusion of bile acids into the mouse pancreatic duct. Nat Protoc 2010; 5:335-41.
15. Gurda G T, Guo L, Lee S H, et al. Cholecystokinin activates pancreatic calcineurin-NFAT signaling in vitro and in vivo. Mol Biol Cell 2008; 19:198-206.
16. Muili K A, Wang D, Orabi A I, et al. Bile acids induce pancreatic acinar cell injury and pancreatitis by activating calcineurin. J Biol Chem 2013; 288:570-80.
17. Logsdon C D, Moessner J, Williams J A, et al. Glucocorticoids increase amylase mRNA levels, secretory organelles, and secretion in pancreatic acinar AR42J cells. J Cell Biol 1985; 100:1200-8.
18. Guo P, El-Gohary Y, Prasadan K, et al. Rapid and simplified purification of recombinant adeno-associated virus. J Virol Methods 2012; 183:139-46.
19. Guo P, Xiao X, El-Gohary Y, et al. Specific transduction and labeling of pancreatic ducts by targeted recombinant viral infusion into mouse pancreatic ducts. Lab Invest 2013; 93:1241-53.
20. Guo P, Xiao X, El-Gohary Y, et al. A simplified purification method for AAV variant by polyethylene glycol aqueous two-phase partitioning. Bioengineered 2013; 4:103-6.
21. Xiao X, Guo P, Prasadan K, et al. Pancreatic cell tracing, lineage tagging and targeted genetic manipulations in multiple cell types using pancreatic ductal infusion of adeno-associated viral vectors and/or cell-tagging dyes. Nat Protoc 2014; 9:2719-24.
22. Noble M D, Romac J, Vigna S R, et al. A pH-sensitive, neurogenic pathway mediates disease severity in a model of post-ERCP pancreatitis. Gut 2008; 57:1566-71.
23. Mishkin D, Carpenter S, Croffie J, et al. ASGE Technology Status Evaluation Report: radiographic contrast media used in ERCP. Gastrointest Endosc 2005; 62:480-4.
24. Pandol S. The Exocrine Pancreas. San Rafael, C A: Morgan & Claypool Life Sciences, 2010.
25. Petersen O H, Sutton R. Ca2+ signalling and pancreatitis: effects of alcohol, bile and coffee. Trends Pharmacol Sci 2006; 27:113-20.
26. Husain S Z, Prasad P, Grant W M, et al. The ryanodine receptor mediates early zymogen activation in pancreatitis. Proc Natl Acad Sci USA 2005; 102:14386-91.
27. Husain S Z, Orabi A I, Muili K A, et al. Ryanodine receptors contribute to bile acid-induced pathological calcium signaling and pancreatitis in mice. Am J Physiol Gastrointest Liver Physiol 2012; 302:G1423-33.
28. Zhang H, Neuhofer P, Song L, et al. IL-6 trans-signaling promotes pancreatitis-associated lung injury and lethality. J Clin Invest 2013; 123:1019-31.
29. Neuhofer P, Liang S, Einwachter H, et al. Deletion of IkappaBalpha Activates RelA to Reduce Acute Pancreatitis in Mice Through Up-regulation of Spi2A. Gastroenterology 2013; 144:192-201.
30. Huang H, Liu Y, Daniluk J, et al. Activation of Nuclear Factor-kappaB in Acinar Cells Increases the Severity of Pancreatitis in Mice. Gastroenterology 2012.
31. Lawrence T. The nuclear factor NF-kappaB pathway in inflammation. Cold Spring Harb Perspect Biol 2009; 1:a001651.
32. Brown K, Gerstberger S, Carlson L, et al. Control of I kappa B-alpha proteolysis by site-specific, signal-induced phosphorylation. Science 1995; 267:1485-8.
33. George S, Kulkarni A A, Stevens G, et al. Role of osmolality of contrast media in the development of post-ERCP pancreatitis: a metanalysis. Dig Dis Sci 2004; 49:503-8.
34. Investigators A. Acetylcysteine for prevention of renal outcomes in patients undergoing coronary and peripheral vascular angiography: main results from the randomized Acetylcysteine for Contrast-induced nephropathy Trial (ACT). Circulation 2011; 124:1250-9.
35. Michael A, Faga T, Pisani A, et al. Molecular mechanisms of renal cellular nephrotoxicity due to radiocontrast media. Biomed Res Int 2014; 2014:249810.
36. Durgampudi C, Noel P, Patel K, et al. Acute lipotoxicity regulates severity of biliary acute pancreatitis without affecting its initiation. Am J Pathol 2014; 184:1773-84.
37. Navina S, Acharya C, DeLany J P, et al. Lipotoxicity causes multisystem organ failure and exacerbates acute pancreatitis in obesity. Sci Transl Med 2011; 3:107ra110.
38. Shah A U, Sarwar A, Orabi A I, et al. Protease Activation during in vivo Pancreatitis is Dependent upon Calcineurin Activation. Am J Physiol Gastrointest Liver Physiol 2009.
39. Orabi A I, Sah S, Javed T A, et al. Dynamic Imaging of Pancreatic Nuclear Factor kappaB (NF-kappaB) Activation in Live Mice Using Adeno-associated Virus (AAV) Infusion and Bioluminescence. The Journal of biological chemistry 2015; 290:11309-20.
40. Giurisato E, Gamberucci A, Ulivieri C, et al. The KSR2-calcineurin complex regulates STIM1-ORAI1 dynamics and store-operated calcium entry (SOCE). Mol Biol Cell 2014; 25:1769-81.
41. Ruben D S, Scorpio D G, Gabrielson K L, et al. Refinement of canine pancreatitis model: inducing pancreatitis by using endoscopic retrograde cholangiopancreatography. Comp Med 2009; 59:78-82.
42. Pfau P R, Mosley R G, Said A, et al. Comparison of the effect of non-ionic and ionic contrast agents on pancreatic histology in a canine model. JOP 2006; 7:27-33.
43. Haciahmetoglu T, Ertekin C, Dolay K, et al. The effects of contrast agent and intraductal pressure changes on the development of pancreatitis in an ERCP model in rats. Langenbecks Arch Surg 2008; 393:367-72.
44. McCullough P A, Khambatta S, Jazrawi A. Minimizing the renal toxicity of iodinated contrast. Circulation 2011; 124:1210-1.
45. Andreucci M, Faga T, Russo D, et al. Differential activation of signaling pathways by lowosmolar and iso-osmolar radiocontrast agents in human renal tubular cells. J Cell Biochem 2014; 115:281-9.

46. Xu X, Wu T, Ding X, et al. The role of nuclear factor-kappaB in rats of radiocontrastmedia-induced nephropathy. J Biochem Mol Toxicol 2008; 22:416-21.
47. Voll R E, Jimi E, Phillips R J, et al. NF-kappa B activation by the pre-T cell receptor serves as a selective survival signal in T lymphocyte development. Immunity 2000; 13:677-89.
48. Sah R P, Dawra R K, Saluja A K. New insights into the pathogenesis of pancreatitis. Curr Opin Gastroenterol 2013; 29:523-30.
49. Saluja A K, Bhagat L, Lee H S, et al. Secretagogue-induced digestive enzyme activation and cell injury in rat pancreatic acini. Am J Physiol 1999; 276:G835-42.
50. Raraty M, Ward J, Erdemli G, et al. Calcium-dependent enzyme activation and vacuole formation in the apical granular region of pancreatic acinar cells. Proc Natl Acad Sci USA 2000; 97:13126-31.
51. Kruger B, Albrecht E, Lerch M M. The role of intracellular calcium signaling in premature protease activation and the onset of pancreatitis. Am J Pathol 2000; 157:43-50.
52. Voronina S G, Barrow S L, Gerasimenko O V, et al. Effects of secretagogues and bile acids on mitochondrial membrane potential of pancreatic acinar cells: comparison of different modes of evaluating DeltaPsim. J Biol Chem 2004; 279:27327-38.
53. Muili K A, Jin S, Orabi A I, et al. Pancreatic acinar cell NF-kappaB activation due to bile acid exposure is dependent on calcineurin. J Biol Chem 2013.
54. Timmerman L A, Clipstone N A, Ho S N, et al. Rapid shuttling of NF-AT in discrimination of Ca2+ signals and immunosuppression. Nature 1996; 383:837-40.
55. Yang D, Jia R, Ding G. Selective inhibition of the reverse mode of Na(+)/Ca(2+) exchanger attenuates contrast-induced cell injury. Am J Nephrol 2013; 37:264-73.
56. Wang Y X, Jia Y F, Chen K M, et al. Radiographic contrast media induced nephropathy: experimental observations and the protective effect of calcium channel blockers. Br J Radiol 2001; 74:1103-8.
57. Muallem S, Beeker T, Pandol S J. Role of Na+/Ca2+ exchange and the plasma membrane Ca2+ pump in hormone-mediated Ca2+ efflux from pancreatic acini. J Membr Biol 1988; 102:153-62.
58. Husain S Z, Grant W M, Gorelick F S, et al. Caerulein-induced intracellular pancreatic zymogen activation is dependent on calcineurin. Am J Physiol Gastrointest Liver Physiol 2007; 292:G1594-9.
59. Muili K A, Ahmad M, Orabi A I, et al. Pharmacological and genetic inhibition of calcineurin protects against carbachol-induced pathological zymogen activation and acinar cell injury. Am J Physiol Gastrointest Liver Physiol 2012; 302:G898-905.
60. Muili K, and Husain, Sohail. Calcineurin. The Pancreapedia: Exocrine Pancreas Knowledge Base 2011; 1.
61. Hogan P G, Li H. Calcineurin. Current Biology 2005; 15:R442-R443.
62. Li H, Rao A, Hogan P G. Interaction of calcineurin with substrates and targeting proteins. Trends Cell Biol 2011; 21:91-103.
63. Gukovskaya A S, Hosseini S, Satoh A, et al. Ethanol differentially regulates NF-kappaB activation in pancreatic acinar cells through calcium and protein kinase C pathways. Am J Physiol Gastrointest Liver Physiol 2004; 286:G204-13.
64. Darrouzet E, Lindenthal S, Marcellin D, et al. The sodium/iodide symporter: state of the art of its molecular characterization. Biochim Biophys Acta 2014; 1838:244-53.
65. Sendeski M M. Pathophysiology of renal tissue damage by iodinated contrast media. Clin Exp Pharmacol Physiol 2011; 38:292-9.
66. Kapturczak M M H, Meier-Kriesche H H U, Kaplan B B. Pharmacology of calcineurin antagonists. Transplantation proceedings 2004; 36:25S-32S.
67. Wildi S, Kleeff J, Mayerle J, et al. Suppression of transforming growth factor {beta} signalling aborts caerulein induced pancreatitis and eliminates restricted stimulation at high caerulein concentrations. Gut 2007; 56:685-92.
68. Orabi A I, Luo Y, Ahmad M U, et al. IP3 receptor type 2 deficiency is associated with a secretory defect in the pancreatic acinar cell and an accumulation of zymogen granules. PLoS One 2012; 7:e48465.
69. Orabi A I, Muili K A, Wang D, et al. Preparation of pancreatic acinar cells for the purpose of calcium imaging, cell injury measurements, and adenoviral infection. J Vis Exp 2013.
70. Maranki J, Yeaton P. Prevention of post-ERCP pancreatitis. Curr Gastroenterol Rep 2013; 15:352. Elmunzer B J, Scheiman J M, Lehman G A, Chak A, Mosler P, Higgins P D, et al. A randomized trial of rectal indomethacin to prevent post-ERCP pancreatitis. N Engl J Med 2012; 366:1414-22.
71. Freeman M L, Kozarek R A. Take 2 Indomethacin (Suppositories) and Call Me in the Morning? The Role of Nonsteroidal Anti-inflammatory Drugs in Protection Against Post-Endoscopic Retrograde Cholangiopancreatography Pancreatitis. Gastroenterology 2016; 150:805-8.
72. Jin S, Orabi A I, Le T, Javed T A, Sah S, Eisses J F, et al. Exposure to Radiocontrast Agents Induces Pancreatic Inflammation by Activation of Nuclear Factor-kB, Calcium Signaling, and Calcineurin. Gastroenterology 2015.
73. Heit J J, Apelqvist A A, Gu X, Winslow M M, Neilson J R, Crabtree G R, et al. p Calcineurin/NFAT signalling regulates pancreatic [beta]-cell growth and function. Nature 2006; 443:345-9.
74. Ji B, Song J, Tsou L, Bi Y, Gaiser S, Mortensen R, et al. Robust acinar cell transgene expression of CreErT via BAC recombineering. Genesis 2008; 46:390-5.
75. Madisen L, Zwingman T A, Sunkin S M, Oh S W, Zariwala H A, Gu H, et al. A robust and high-throughput Cre reporting and characterization system for the whole mouse brain. Nat Neurosci 2010; 13:133-40.
76. Strauss W M. Preparation of Genomic DNA from Mammalian Tissue. Current Protocols in Molecular Biology, 2001.
77. Sztal T E, Zhao M, Williams C, Oorschot V, Parslow A C, Giousoh A, et al. Zebrafish models for nemaline myopathy reveal a spectrum of nemaline bodies contributing to reduced muscle function. Acta Neuropathol 2015; 130:389-406.
78. Swift G H, Craik C S, Stary S J, Quinto C, Lahaie R G, Rutter W J, et al. Structure of the two related elastase genes expressed in the rat pancreas. J Biol Chem 1984; 259:14271-8.
79. Wang Z, Zhu T, Rehman K K, Bertera S, Zhang J, Chen C, et al. Widespread and stable pancreatic gene transfer by adeno-associated virus vectors via different routes. Diabetes 2006; 55:875-84.

80. Echigo Y, Inoue K, Kogire M, Doi R, Higashide S, Sumi S, et al. Effects of cyclosporine and tacrolimus (FK 506) on acute pancreatitis in mice. Arch Surg 1995; 130:64-8.
81. Vaquero E, Molero X, Tian X, Salas A, Malagelada J R. Myofibroblast proliferation, fibrosis, and defective pancreatic repair induced by cyclosporin in rats. Gut 1999; 45:269-77.
82. Yang Y R, Follo M Y, Cocco L, & Suh P G (2013) The physiological roles of primary phospholipase C. Adv Biol Regul 53(3):232-241.
83. Williams J A (2010) Regulation of acinar cell function in the pancreas. Curr Opin Gastroenterol 26(5):478-483.
84. U.S. Pat. No. 8,560,053.
85. U.S. Pat. No. 7,160,535.
86. U.S. Pat. No. 8,192,721.
87. International Patent Application Publication No. WO1996034645.
88. Chinese Patent Application No. 101297975.
89. U.S. Pat. No. 7,947,285.
90. United States Patent Application Publication No. 20030133906.
91. United States Patent Application Publication No. 20090042969.
92. U.S. Pat. No. 7,833,279.
93. United States Patent Application Publication No. 20130123934.
94. International Patent Application Publication No. WO2005004857.
95. Chinese Patent Application No. CN101627987.
96. U.S. Pat. No. 8,318,657.
97. United States Patent Application Publication No. 20120171168.
98. International Patent Application Publication No. WO2009137827.
99. International Patent Application Publication No. WO2009049022.
100. Bang et al., Pharmacological approach to acute pancreatitis. 2008, World J. Gastroenterol. 14(19):2968-2976.
101. Kamaldeen et al., Bile Acids Induce Pancreatic Acinar Cell Injury and Pancreatitis by Activating Calcineurin. 2013, J. Biol. Chem. 288:570-580.
102. Nagashio and Otsuki, Action of Antiproteases on Fibrosis in Experimental Chronic Pancreatitis 2007, J. Pancreas: 8(4 Suppl):495-500.
103. Talukdar and Tandon, 2007, Pancreatic stellate cells: New target in the treatment of chronic pancreatitis. J. Gastroenterol. Hepatol. 23:34-41.
104. Chinese Patent Application No. 102144978.
105. U.S. Pat. No. 7,060,733.
106. Virlos et al. (2003), Action of Antiproteases on Fibrosis in Experimental Chronic Pancreatitis Scandanavia J. Gastroenterol. 38:1262-1267.
107. Demols et al. (2000) N-acetylcysteine decreases severity of acute pancreatitis in mice. Pancreas 20(2):161-169.
108. Du et al., N-Acetylcysteine Improves Pancreatic Microcirculation and Alleviates the Severity of Acute Necrotizing Pancreatitis (2013) Gut Liver 7(3):357-362.
109. Ramudo and Manso, N-acetylcysteine in acute pancreatitis. (2010) World J Gastrointest Pharmacol Ther 1(1):21-26.
110. International Patent Application Publication No. WO2008021550.
111. International Patent Application Publication No. WO2008057534.
112. International Patent Application Publication No. WO2009088860.
113. European Patent Application Publication No. 2574333.
114. Canadian Patent Application No. 2603084.
115. Chinese Patent Application No. 103432099.
116. Nieto et al., Acute pancreatitis during immunosuppression with tacrolimus following an allogeneic umbilical cord blood transplantation. (2000) Bone Marrow Transpl. 26:109-11
117. Im et al., Diabetic ketoacidosis associated with acute pancreatitis in a heart transplant recipient treated with tacrolimus. (2013) Exp. Clin. Transplant 11(1):72-74.
118. Liu et al., Anti-inflammatory effects of tacrolimus in a rat model of acute pancreatitis. (2010) Med. Chem. 6(1): 37-43.
119. Lee et al., Cyclosporin a, but not FK506, induces osmotic lysis of pancreas zymogen granules, intra-acinar enzyme release, and lysosome instability by activating K+ channel. (2012) Pancreas 41(4):596-604.
120. Mayer et al., Single doses of FK506 and OKT3 reduce severity in early experimental acute pancreatitis. (2000) Eur. J. Surgery 166(9):734-741.
121. Rehman et al., N-acetylcysteine effect on serum creatinine and cystatin C levels in CKD patients (2008) Clin. J. Am. Soc. Nephrol. 3(6):1610-1614.

Various references are cited herein, the contents of which are hereby incorporated by reference in their entireties.

What is claimed:

1. A radiocontrast medium comprising (i) an iodinated radiocontrast agent; (ii) a calcineurin inhibitor; and (iii) an antioxidant, in amounts effective in radioimaging in a subject with reduced risk of post-imaging pancreatitis relative to the radiocontrast agent administered without the calcineurin inhibitor and the antioxidant.

2. The radiocontrast medium of claim 1, where the iodinated radiocontrast agent is a water-soluble non-ionic radiocontrast agent.

3. The radiocontrast medium of claim 1, where the calcineurin inhibitor is cyclosporine.

4. The radiocontrast medium of claim 1, where the antioxidant is N-acetylcysteine.

5. The radiocontrast medium of claim 1, where the calcineurin inhibitor is FK506.

6. A method of radioimaging a pancreas, gallbladder, and/or biliary tree in a subject, comprising a) introducing, into the pancreas, gallbladder and/or biliary tree of the subject, a radiocontrast medium comprising effective amounts of (i) an iodinated radiocontrast agent; (ii) a calcineurin inhibitor; and (iii) an antioxidant; and b) performing imaging of the pancreas, gallbladder, and/or biliary tree.

7. The method of claim 6, where the iodinated radiocontrast agent is a water-soluble non-ionic radiocontrast agent.

8. The method of claim 6, where the calcineurin inhibitor is cyclosporine.

9. The method of claim 6, where the antioxidant is N-acetylcysteine.

10. The method of claim 6, where the calcineurin inhibitor is FK506.

11. A method of reducing the risk of post-imaging pancreatitis in a subject in need of such treatment comprising using, as an agent for imaging the pancreas, gallbladder, and/or biliary tree of the subject, a radiocontrast medium comprising (i) an iodinated radiocontrast agent; (ii) a calcineurin inhibitor; and (iii) an antioxidant in amounts such that the risk of post-imaging pancreatitis in the subject is reduced.

12. The method of claim 11, where the iodinated radiocontrast agent is a water-soluble non-ionic radiocontrast agent.

13. The method of claim 11, where the calcineurin inhibitor is cyclosporine.

14. The method of claim 11, where the calcineurin inhibitor is FK506.

15. The method of claim 11, where the antioxidant is N-acetylcysteine.

* * * * *

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Forward primer - 5'loxp site

<400> SEQUENCE: 1
tctaggtaat tagggcaggt gc                                                  22

<210> SEQ ID NO 2
<211> LENGTH: 22
<212> TYPE: DNA
<213> ORGANISM: Artificial Sequence
<220> FEATURE:
<223> OTHER INFORMATION: Reverse primer - 5'loxp site
```

-continued

```
<400> SEQUENCE: 2
gcttcttgaa tctctttcct ag                                              22

<210> SEQ ID NO 3
<211> LENGTH: 23
<212> TYPE: DNA
<213> ORGANISM: Artificial Sequence
<220> FEATURE:
<223> OTHER INFORMATION: Forward primer - 3'loxp site

<400> SEQUENCE: 3
gacagctata cagagaaacc ctg                                             23

<210> SEQ ID NO 4
<211> LENGTH: 21
<212> TYPE: DNA
<213> ORGANISM: Artificial Sequence
<220> FEATURE:
<223> OTHER INFORMATION: Reverse primer - 3'loxp site

<400> SEQUENCE: 4
agcctccaca tacacagata c                                               21

<210> SEQ ID NO 5
<211> LENGTH: 18
<212> TYPE: DNA
<213> ORGANISM: Artificial Sequence
<220> FEATURE:
<223> OTHER INFORMATION: Forward primer - Cre

<400> SEQUENCE: 5
gcctgcatta ccggtcga                                                   18

<210> SEQ ID NO 6
<211> LENGTH: 18
<212> TYPE: DNA
<213> ORGANISM: Artificial Sequence
<220> FEATURE:
<223> OTHER INFORMATION: Reverse primer - Cre

<400> SEQUENCE: 6
tatcctggca gcgatcgc                                                   18

<210> SEQ ID NO 7
<211> LENGTH: 20
<212> TYPE: DNA
<213> ORGANISM: Artificial Sequence
<220> FEATURE:
<223> OTHER INFORMATION: Forward primer - ERT2

<400> SEQUENCE: 7
gcgatccacg aaatgaaatg                                                 20

<210> SEQ ID NO 8
<211> LENGTH: 20
<212> TYPE: DNA
<213> ORGANISM: Artificial Sequence
<220> FEATURE:
<223> OTHER INFORMATION: Reverse primer - ERT2

<400> SEQUENCE: 8
gcaggttcat catgcggaac                                                 20

<210> SEQ ID NO 9
```

```
<211> LENGTH: 21
<212> TYPE: DNA
<213> ORGANISM: Artificial Sequence
<220> FEATURE:
<223> OTHER INFORMATION: Forward primer - CnB1

<400> SEQUENCE: 9
caatgcagtc cgctgtagtt c                                          21

<210> SEQ ID NO 10
<211> LENGTH: 21
<212> TYPE: DNA
<213> ORGANISM: Artificial Sequence
<220> FEATURE:
<223> OTHER INFORMATION: Reverse primer - CnB1

<400> SEQUENCE: 10
agcctccaca tacacagata c                                          21
```